United States Patent
Scherman et al.

(10) Patent No.: US 11,697,715 B2
(45) Date of Patent: Jul. 11, 2023

(54) CUCURBITURIL-BASED HYDROGELS

(71) Applicants: Oren Scherman, Cambridge (GB); Ji Liu, Cambridge (GB)

(72) Inventors: Oren Scherman, Cambridge (GB); Ji Liu, Cambridge (GB)

( * ) Notice: Subject to any disclaimer, the term of this patent is extended or adjusted under 35 U.S.C. 154(b) by 0 days.

(21) Appl. No.: 17/861,772

(22) Filed: Jul. 11, 2022

(65) Prior Publication Data

US 2022/0411591 A1    Dec. 29, 2022

Related U.S. Application Data

(62) Division of application No. 16/340,835, filed as application No. PCT/EP2017/076227 on Oct. 13, 2017, now Pat. No. 11,479,644.

(30) Foreign Application Priority Data

Oct. 14, 2016  (GB) ..................... 1617469

(51) Int. Cl.
| | |
|---|---|
| *C08G 83/00* | (2006.01) |
| *C08G 73/06* | (2006.01) |
| *C08J 3/075* | (2006.01) |
| *C08J 3/24* | (2006.01) |
| *A61K 47/58* | (2017.01) |
| *A61L 24/04* | (2006.01) |
| *A61L 24/00* | (2006.01) |

(52) U.S. Cl.
CPC ............ *C08G 83/008* (2013.01); *A61K 47/58* (2017.08); *A61L 24/043* (2013.01); *C08G 73/06* (2013.01); *C08G 83/007* (2013.01); *C08J 3/075* (2013.01); *C08J 3/246* (2013.01); *A61L 24/0031* (2013.01); *C08J 2379/04* (2013.01)

(58) Field of Classification Search
CPC ...... C08G 83/008; C08G 73/06; A61K 47/58; A61L 24/043; A61L 24/0031; C08J 3/075; C08J 3/246; C08J 2379/04
See application file for complete search history.

(56) References Cited

U.S. PATENT DOCUMENTS

| | | | |
|---|---|---|---|
| 2006/0201862 A1* | 9/2006 | Kim .................. | C08K 3/36 210/502.1 |
| 2015/0110772 A1* | 4/2015 | Scherman ........... | C08B 37/0015 514/772.3 |
| 2016/0340467 A1 | 11/2016 | Cheesman et al. | |

FOREIGN PATENT DOCUMENTS

| | | |
|---|---|---|
| CN | 104245801 A | 12/2014 |
| WO | 2013124654 A1 | 8/2013 |

OTHER PUBLICATIONS

Lagona, J. et al. The Cucurbit[n]uril Family. Angew. Chem. Int. Ed. 2005, 44, 4844-4870. (Year: 2005).*

(Continued)

*Primary Examiner* — Michael M Dollinger
*Assistant Examiner* — Christina H. W. Rosebach
(74) *Attorney, Agent, or Firm* — Cantor Colburn LLP

(57) ABSTRACT

The invention provides a polymerizable composition and a hydrogel obtained or obtainable from the polymerizable composition. The polymerizable composition comprises cucurbituril and a first monomer having a guest for the cucurbituril, wherein the total monomer concentration, $C_{mon}$, within the polymerizable composition is at least 0.5 M. The composition may be an aqueous composition.

6 Claims, 32 Drawing Sheets

(56) References Cited

OTHER PUBLICATIONS

Song, Q. et al. Supramolecular Microgels Fabricated from Supramonomers. ACS Macro Lett. 2016, 5, 1084-1088. (Year: 2016).*
Nau, W.M. et al. Deep Inside Cucurbiturils: Physical Properties and Volumes of their Inner Cavity Determine the Hydrophobic Driving Force for Host-Guest Complexation. Isr. J. Chem. 2011, 51, 559-577. (Year: 2011).*
Zou, H. et al. Cucurbit[8]uril-Based Polymers and Polymer Materials. Small 2018, 14, 1802234. (Year: 2018).*
Xu, et al., "Supramolecular Hydrogels Fabricated from Supramonomers: A Novel Wound Dressing Material" ACS Applied Materials & Internfaces 2017, vol. 9 (11368-11372).
Lee, J.W.; Samal, S.; Selvapalam, N.; Kim, H.J.; Kim, K. Cucurbituril Homologues and Derivatives: New Opportunities in Supramolecular Chemistry. Acc. Chem. Res. 2003, 36, 621-630 (Year: 2003).
W.M. Nau; M. Florea; K. I. Assaf. Deep Inside Cucurbiturils: Physical Properties and Volumes of their Inner Cavity Determine the Hydrophobic Driving Force for Host-Guest Complexation. Isr. J. Chem. 2011, 51, 559-577.
Xiaohe Ren et al., "Surface-Bound Cucurbit[8]uril Catenanes on Magnetic Nanoparticles Exhibiting Molecular Recognition", Chemistry an Asian Journal, vol. 11, (2016) pp. 2382-2386.
Written Opinion for International Application No. PCT/EP2017/076227, International Filing Date Oct. 13, 2017, dated Jan. 25, 2018, 6 pages.
CN103242538_scifinder abstract. (Year: 2013).
Jason Lagana, Pritam Mukhopadhyay, Sriparna Chakrabarti, and Lyle Isaacs. The Cucurbit[n]uril Family. Angew. Chem. Int. Ed.2005, 44, 4844-4870 (Year: 2005).

Machine translation of CN 103242538A by Gu et al. (Year: 2013).
Pham, H.Q. and Marks, M.J. (2004). Epoxy Resins. In Encyclopedia of Polymer Science and Technology, (Ed.). https://doi.org/10.1002/0471440264.pst119 (Year: 2004).
Qiao Song, Yongfeng Gao, Jiang-Fei Xu, Bo Qin, Michael J. Serpe, and Xi Zhang. Supramolecular Microgels Fabricated from Supramonomers.ACS Macro Lett. 2016, 5, 1084-1088. (Year: 2016).
Epichlorohydrin. By Chemicalbook. Accessed on Mar. 9, 2021 at https://www.chemicalbook.com/Chemical ProductProperty_EN_CB8381781 .htm#:-:text=wel 1 %20as %20alcohols. -, Chemical %20 Properties ,miscible%20with%20most%20organic%20solvents. (Year: 2017).
Hua Zou, Jing Liu, Ying Li, Xiaoyan Li, and Xia Wang. Cucurbit[8]uril-Based Polymers and Polymer Materials. Small 2018, 14,1802234 (Year: 2018).
Eric A. Appel et al., "Ultrahigh-Water-Content Supramolecular Hydrogels Exhibiting Multistimuli Responsiveness", Journal of the American Chemical Society, vol. 134, (2012), pp. 11767-11773.
Eric A. Appel et al., Supramolecular Cross-Linked Networks via Host-Guest Complexation with Cucurbit[8]uril, Journal of American Chemical Society, vol. 132, (2010), pp. 14251-14260.
International Search Report for International Application No. PCT/EP2017/076227, International Filing Date Oct. 13, 2017, dated Jan. 25, 2018, 4 pages.
Qiao Song et al., "Supramolecular Microgels Fabricated from Supramonomers", ACS Macro Letters, No. 5, (2016), pp. 1084-1088.
Rabbab Oun et al., "A cisplatin slow-release hydrogel drug delivery system based on a formulation of the macrocycle cucurbit[7]uril, gelatin and polyvinyl alcohol", Journal of Inorganic Biochemistry, vol. 134, (2014), pp. 100-105.

* cited by examiner

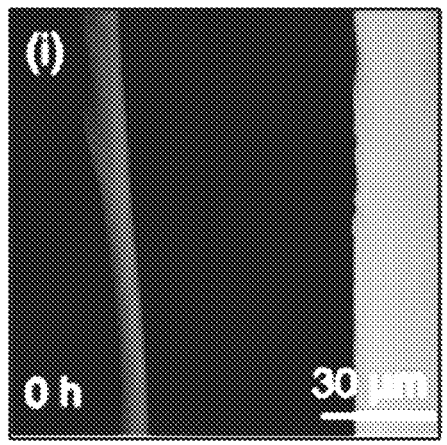
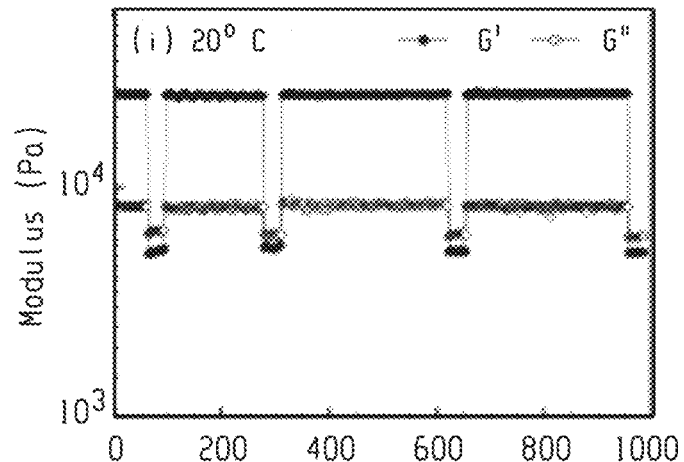
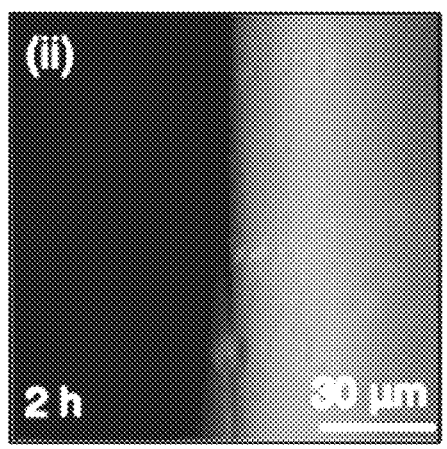
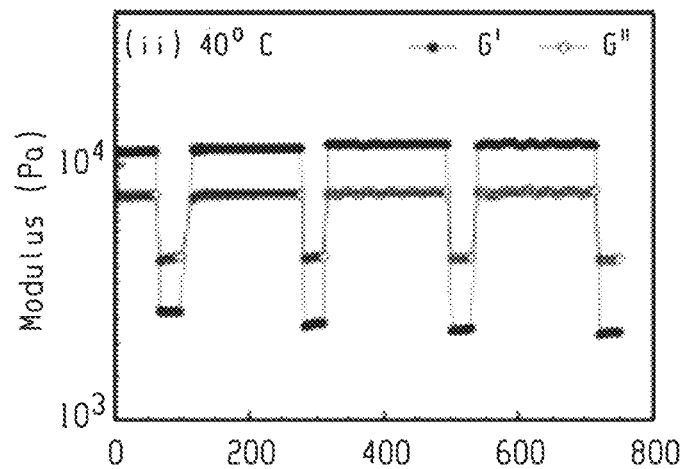
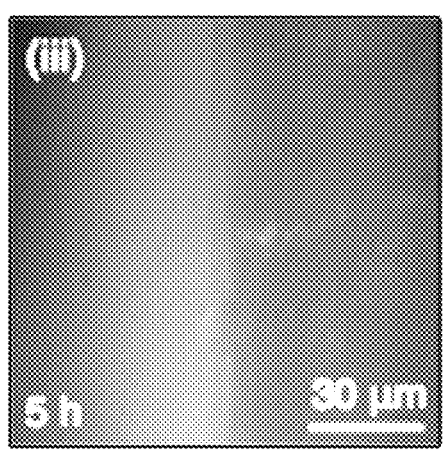
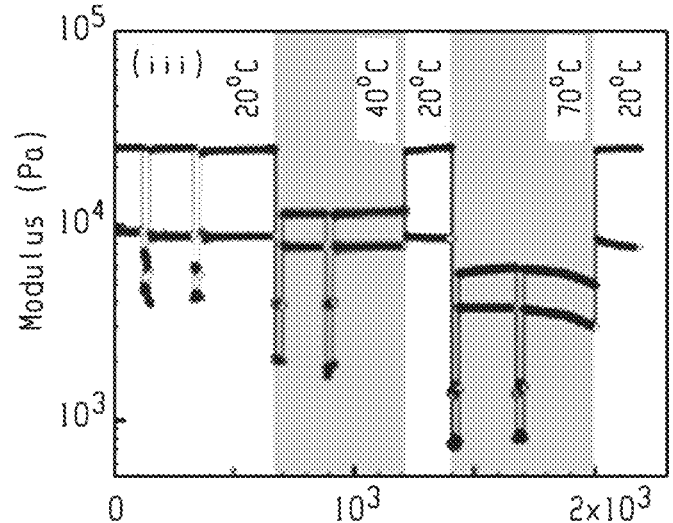
Fig. 3c
Fig. 3d original sample compression recovery

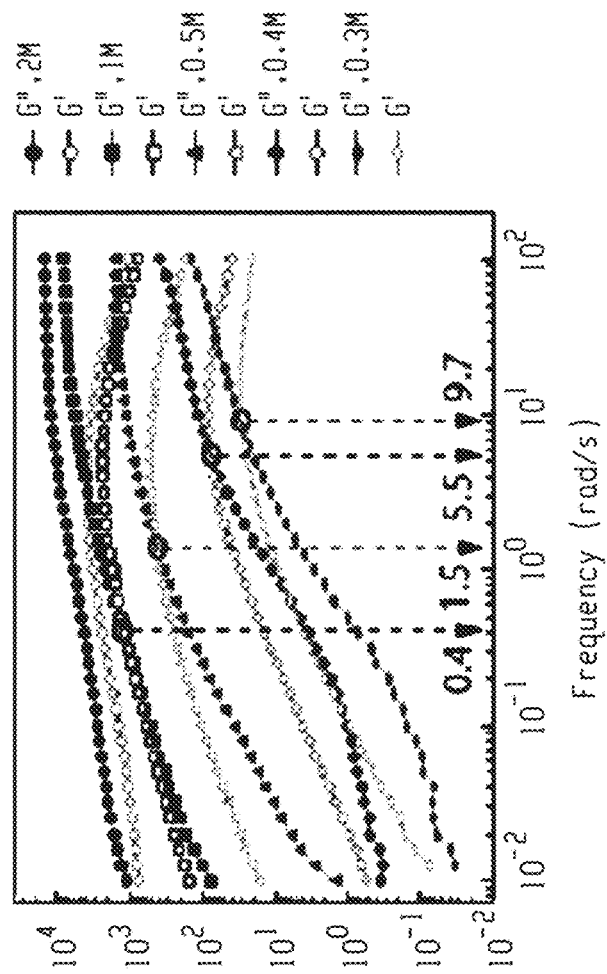
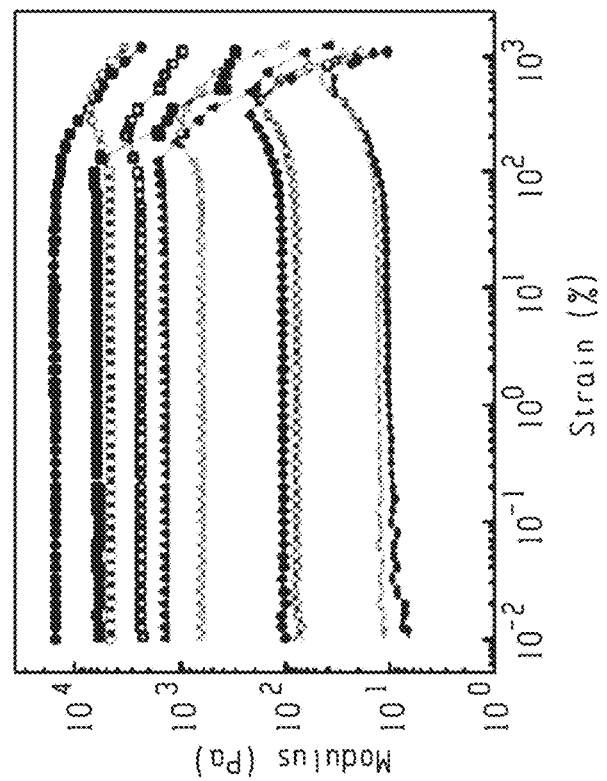
Fig. 9b
Fig. 9a

CUCURBITURIL-BASED HYDROGELS

CROSS REFERENCE TO RELATED APPLICATIONS

This application is a divisional of U.S. patent application Ser. No. 16/340,835, filed on Apr. 10, 2019, which claims priority to PCT/EP2017/076227, filed on Oct. 13, 2017, and Great Britain Patent Application No. 1708589.5 filed on May 30, 2017 and Great Britain Patent Application No. 1617469.0 filed on Oct. 14, 2016, all of which are incorporated by reference in their entireties herein.

RELATED APPLICATIONS

The present case is related to GB 1617469.0 filed on 14 Oct. 2016 and GB 1708589.5 filed on 30 May 2017, the contents of both of which are hereby incorporated by reference in their entirety.

FIELD OF THE INVENTION

This invention relates to hydrogels based on cucurbituril cross-linked supramolecular networks, and methods for the preparation of such hydrogels from a polymerizable composition comprising cucurbituril and a polymerizable monomer having a guest for the cucurbituril.

BACKGROUND

Some of the present inventors have previously described supramolecular hydrogels that are based on the supramolecular complexation of the cucurbituril CB[8] with a polymer having guest functionality for CB[8].

Appel et al. (*J. Am. Chem. Soc.* 2010, 132, 14251) describe hydrogels formed from the complexation of a composition comprising CB[8] and a low molecular weight polymer having guests for CB[8]. The supramolecular hydrogel has intra- and intermolecular non-covalent cross-links between polymers based on a ternary complex of CB[8] with two guests. The rheological properties of the hydrogels were studied.

In later work reported in WO 2013/124654, some of the inventors described the formation of hydrogels from the complexation of a composition comprising CB[8] and a high molecular weight polymer having guests for CB[8]. This work also described hydrogels holding components for delivery. Such hydrogels were formed from complexation of a composition comprising CB[8] and a low or a high molecular weight polymer having guests for CB[8]. The component for delivery could be contained in the composition, to be incorporated during complexation, or the component could be added later. This work was also reported in Appel et al. (*J. Am. Chem. Soc.*, 2012, 134, 11767).

US 2012/0103615 describes earlier work by some of the inventors in developing viscosifying polymers, for example for a wellbore fluid. These viscosifying polymers are based on the complexation of a polymerizable composition comprising a cucurbituril, such as CB[8], and guest groups provided on polymer chains. The systems here are very similar to those described in Appel et al. and WO 2013/124654.

The hydrogels previously reported by the inventors are useful, but their uses are limited by their relatively weak mechanical performance. In order to obtain improved mechanical characteristics, a higher degree of crosslinking is desirable. However, the use of increasing amounts of CB[8] is impeded by the limited solubility of this cucurbituril in compositions also comprising the polymers for the hydrogel network. The hydrogel systems described in the art add CB[8] into a highly-viscous composition comprising polymers with guests for CB[8]. Such mixtures are not ideal, as they limit the types of structure than can be prepared, and there can be issues in manipulating the mixtures when used on a larger scale.

For example, in Appel et al. (2010) the rheological properties of the hydrogel materials were analysed by dynamic oscillatory rheology at 10% strain, the loss modulus (G") is observed to dominate the storage modulus (G') at higher frequencies. Thus, the loss modulus is dominant at frequencies of 20 rad/s or more. At lower frequencies the storage module is dominant. G' and G" are therefore not linear and are not parallel in the oscillatory rheology.

The hydrogels reported in WO 2013/124654 generally have storage and loss moduli that are less than 1,000 Pa, as measured across the range 0.1 to 100 rad/s in a dynamic frequency sweep experiment, and less than 1,000 Pa in the range 0.1 to 10% strain in an amplitude sweep experiment.

Hydrogels having improved mechanical properties are therefore desirable.

Most synthetic hydrogels are brittle and therefore poor candidates for mimicking biomaterials, regardless of their soft and wet nature, similar to that of biological tissues.

However, recent work on alternative supramolecular hydrogel systems has shown that it is possible to produce very tough materials for use as structural biomaterials, such as cartilage, by introducing sacrificial bonds, which can effectively improve the mechanical strength as well as the toughness, damping and fatigue resistance. However, designing soft materials with high toughness and extreme stretchability is still a challenge.

The present work provides alternative hydrogels that differ from those described in earlier work, both in the methods for the preparation of the hydrogel and the structure and characteristics of the hydrogel product.

SUMMARY OF THE INVENTION

Generally the present invention provides a supramolecular hydrogel obtained or obtainable from an aqueous polymerizable composition comprising a cucurbituril and a first monomer having a guest for the cucurbituril. An example cucurbituril for use in the invention is cucurbit[8]uril (CB[8]), which is suitable for preparing supramolecular hydrogels based on ternary host-guest complexes.

The present inventors have found that these hydrogels have excellent mechanical physio-chemical properties, and these properties are improved compared with the cucurbituril hydrogels described previously by some of the inventors.

The supramolecular hydrogel is obtained or obtainable from an aqueous polymerizable composition comprising the cucurbituril and the first monomer having a guest for the cucurbituril. The hydrogels are therefore prepared by in-situ polymerization. Preparing polymers in the presence of the cucurbituril host and its guests permits the formation of hydrogels having a high degree of chain entanglement, a property that is not obtainable from the previously reported methods for preparing cucurbituril hydrogels. Such entanglement may be achieved without the need for a highly concentrated polymerizable composition. However, to obtain the desirable physical properties of the hydrogel it also necessary to use a polymerizable composition where the concertation of monomers is not too dilute. Thus, the total monomer concentration, $C_{mon}$, is typically at least 0.5 M. The chain entanglement contributes to the beneficial properties of the material. The host-guest complex that provides the supramolecular crosslinks in the hydrogel product may also be pre-formed in the polymerizable composition.

Using a polymerizable composition to prepare a hydrogel allows the use of the cucurbituril host and the cucurbituril guest at higher effective concentrations than previously reported. This therefore permits the formation of hydrogels having a higher degree of dynamic crosslinking. The formation of the supramolecular bonding is not affected by the issues seen from previous hydrogel preparations, where the supramolecular bonds are formed between polymers. In these prior art methods, a high level of non-covalent crosslinking is prevented by, amongst others, polymer chain entanglement, limited solubility of guest-functionalised polymers, low cucurbituril solubility in the polymer mixture, and the high viscosity of the starting polymer mixture.

Furthermore, preparing the hydrogel from a polymerizable composition provides many options for variation in the hydrogel, as the cucurbituril host and the first monomer, together with its guest, are easily changed, and a great variety of alternative hosts and guests can be used, providing the possibility of modifying the properties of the product hydrogel. Additional reagents, such as additional polymerizable co-monomers, may be added into the polymerizable composition, providing further options for modifying the hydrogel. Modification of the prior art hydrogels is limited by the fact that the polymers are pre-constructed, and the options for variation are therefore somewhat limited.

The hydrogels of the invention may be prepared with a high water content, such as in the range 80 to 95 wt % water. These hydrogels nevertheless have great stretchability (for example, stretched up to 45 times their original length, such as 100 times their original length), and have very high fracture energies (for example, up to 2,100 J m$^2$). The hydrogels also have a high contractile stress (for example, up to 0.5 MPa), and they are capable of lifting objects having considerably greater mass than the hydrogel (for example, 500 times greater mass, such as 2,000 times greater mass). The hydrogels of the invention have high storage and loss moduli across a wide range of strain and frequency values (for example, 1,000 Pa or more, such as 10,000 Pa or more).

In a first aspect of the invention there is provided a polymerizable composition comprising a cucurbituril and a first monomer having a guest for the cucurbituril. The polymerizable composition may be an aqueous polymerizable composition. The total monomer concentration, $C_{mon}$, within the polymerizable composition may be at least 0.5 M.

In a second aspect of the invention there is provided a hydrogel obtained or obtainable from an aqueous polymerizable composition comprising a cucurbituril and a first monomer having a guest for the cucurbituril.

A hydrogel of the invention contains a supramolecular network of polymers. The polymers are interconnected or intraconnected by non-covalent bonds, and optionally the polymers are also interconnected or intraconnected by covalent bonds. The network may be based on ternary or binary non-covalent complexes of cucurbituril with guest molecules provided on the polymers.

In a third aspect of the invention there is provided a method of preparing a hydrogel, the method comprising polymerizing an aqueous polymerizable composition comprising a cucurbituril and a first monomer having a guest for the cucurbituril. The polymerization may be performed under mild and ambient temperatures.

A polymerizable composition may comprise one or more, such as one, co-monomers for co-polymerization with the first monomer. A co-monomer does not need to possess a guest for a cucurbituril, but optionally it may do so. Typically a co-monomer does not contain functionality for forming a host-guest complex with a cucurbituril. However a co-monomer having functionality for forming a host-guest complex with a cucurbituril may be present. The monomers present in the polymerizable composition may be at least partially soluble in water. The monomers may be hydrophilic monomers.

The composition may contain a second polymerizable co-monomer. The second polymerizable co-monomer differs from the first monomer. The second polymerizable co-monomer may not possess a guest for a cucurbituril.

The cucurbituril may be a cucurbituril having the ability to form a ternary complex. The cucurbituril may be a CB[8], including variants and derivatives thereof.

The supramolecular hydrogel may contain a ternary complex of the cucurbituril with two guests. Typically the guests in the ternary complex are the same. However, in other embodiments, the guests in the ternary complex may be different.

In one embodiment, the hydrogel holds a component for delivery, such as a drug. Here, the component for delivery may be provided in the polymerizable composition prior to polymerization. During the polymerization procedure the component is incorporated into the hydrogel network.

In a further aspect of the invention there is provided an adhesive comprising a hydrogel of the invention.

In yet a further aspect of the invention there is provided a biomaterial, such as a tissue, bone or cartilage biomaterial, comprising the hydrogel of the invention.

The present invention also provides the hydrogel for use in a method of treatment.

In a further aspect of the present case there is provided a polymer that is obtained or obtainable from the polymerization of a polymerizable composition of the invention.

In another aspect of the invention there is provided a method for the preparation of a polymer, the method comprising the step of polymerizing a polymerizable composition of the invention, such as the composition of the first aspect of the invention.

These and other aspects and embodiments of the invention are described in further detail below.

SUMMARY OF THE FIGURES

FIG. 1b shows the uniaxial tensile behaviour of a hydrogel prepared from a polymerizable composition having a total monomer concentration of 2 M under different deformation rates ranging from 50 (bottom) to 1,000 mm/min (top). Note that all of the samples reach the maximum strain of the tensile machine without fracture;

FIG. 3c show fluorescence microscopic images of two supramolecular polymer networks, one chemically-labelled with RITC (red), the other with FITC (green). Two polymer gel films (5 cm (width)×5 mm (length)×50 mm (thickness)) were brought together (contact surface: 5 mm×50 mm) with a gap of ca. 50 mm (black area, i), self-healing at room temperature for 2 h (ii) and 5 h (iii). The appearance of the light yellow area confirms the self-healing at the contacting region and FIG. 3d shows the continuous step-strain measurements of a hydrogel sample at 20° C. (i), 40° C. (ii) and over a series step heating and cooling between 20° C., and 40° C. and 70° C. (high-amplitude oscillatory parameters: strain, γ=500%, angular frequency, ω=10 rad s$^{-1}$; and low-amplitude oscillatory parameters: γ=0.5%, angular frequency, ω=10 rad s$^{-1}$). In all experiments the virgin hydrogel is a non-covalent hydrogel prepared from a polymerizable composition having a total monomer concentration of 2 M.

FIG. 9a shows the change in Modulus (Pa) for G' and G" for hydrogels prepared with different total monomer concentrations with change in strain (%) in a dynamic room-temperature amplitude sweep (from 0.1 to 1000% strain, 10 rad s$^{-1}$); FIG. 9b shows the change in Modulus (Pa) for G' and G" for hydrogels prepared with different total monomer concentrations with change in frequency (rad/s) in a frequency sweep (from 0.1 to 100 s$^{-1}$)

DETAILED DESCRIPTION OF THE INVENTION

Figure 1A:
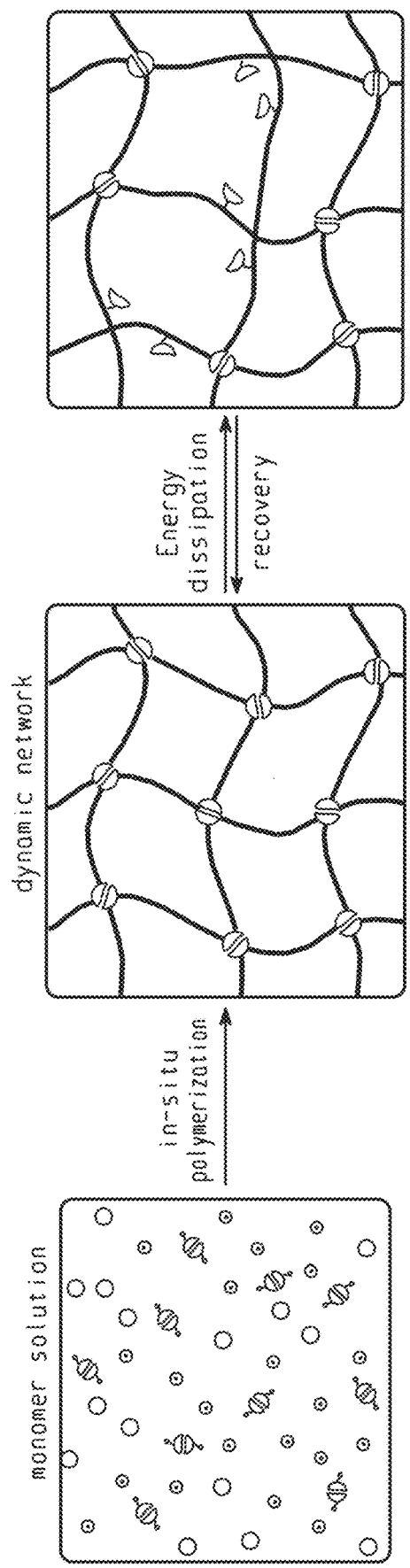
FIG. 1a is a schematic drawing of an in situ polymerization reaction for the preparation of a supramolecular polymer network.

In one of the inventor's earlier work, cucurbituril-based supramolecular hydrogels were formed by supramolecular complexation of polymers having suitable guest functionality for a cucurbituril host. Thus, a polymer was only exposed to the cucurbituril host after the polymer had been prepared. Examples of these methods are set out in Appel et al. (2010 and 2012) and WO 2013/124654.

In the present work, a polymerizable composition is provided where the cucurbituril host is present together with the monomers for preparing the polymer. The monomers possess the guest functionality for forming complexes with the cucurbituril host. Thus, host-guest complexation may be permitted before and during polymerization of the monomers, thereby forming a supramolecular hydrogel. The method therefore differs from those previously described by Appel et al. (2010 and 2012) and WO 2013/124654.

It has been found that the hydrogels prepared by the methods of the present invention have altered rheological properties compared to those hydrogels prepared by complexation of polymers.

The inventors understand that the previous methods for preparing hydrogels were hindered by the limited solubility of the cucurbituril host molecules in the polymer mixture for preparing the hydrogel. This solubility limitation prevented the formation of hydrogels having a very high degree of cross-linking. The limited solubility of the cucurbituril is also believed to be responsible for the formation of inhomogeneities within the prior art hydrogel structures.

The present inventors believe that the toughness of the present supramolecular hydrogels is attributable to the synergistic contribution of two mechanisms: crack bridging (that is a crack tip that impedes the crack growth) by polymer chain entanglement, and energy dissipation by disassociation of the supramolecular cucurbituril-mediated host-guest complexation. The disassociation of the supramolecular crosslinks within the hydrogel is an internal damage to the hydrogel structure, and this damage is subsequently healed by reformation of the host-guest complexes.

For this reason, the hydrogels of the invention, which are extremely tough and have extremely stretchable properties, may be used as model systems to explore mechanisms of deformation and energy dissipation, and the hydrogels may be used in in applications needing tough and stretchable materials, such as biomaterials and wearable electronic devices. The hydrogels of the invention also offer an alternative to the cucurbituril hydrogels known to date, which have a relatively weaker mechanical performance.

The hydrogels of the present case have improved tensile toughness, and the ability to readily alter the components within the polymerizable composition offers the opportunity to modify, such as enhance, the properties of the material, such as to improve the high water uptake, without sacrificing strength and resilience. The presence of dynamic physical bonding within the hydrogel promotes processability and self-healing.

The hydrogels of the present case may be prepared by polymerization of the polymerizable composition in situ. The hydrogel is formed in the shape of the container in which the polymerizable composition is held. Hydrogels having a desired shape may there be prepared by simple choice of polymerization vessel.

The inventors have found that the properties of the hydrogel may be further modified by the incorporation of supplementary covalent bonding into the hydrogel structure. Thus, a crosslinker (a crosslinking monomer, referred to as a fourth monomer herein) may be additionally present in the polymerizable composition. Such hydrogels are referred to as hydrogel dual networks, as they contain both non-covalent and covalent connections between polymer molecules.

In earlier work on hydrogels in WO 2013/124654, one of the present inventors contemplated the formation of covalent bonds within a hydrogel structure. However, the worked examples there describe the formation of covalent bonding at the expense of non-covalent bonding in the supramolecular complex. The inventor initially prepared a supramolecular hydrogel having inter- and intra-molecular crosslinks formed by a ternary complex of CB[8] with two anthracene guests, each of which was connected to a polymer molecule. The hydrogel was irradiated, resulting in an intermolecular cyclisation of the anthracene groups within the complex, thereby forming covalent connections through the complex.

In contrast, the hydrogels of the present case retain the dynamic non-covalent connections, which are associated with fracture resistance, energy dissipation and fatigue resistance, and also the permanent covalent connections which maintain the shape of the network and impart elasticity to the material.

Song et al. have recently described the preparation of a microgel product prepared from an aqueous mixture of N-isopropyl acrylamide, and CB[8] in a ternary complex with two Phe-Gly-Gly groups that are each covalently connected to an acrylate moiety.

Polymerization of the mixture provides microgels dispersed in an aqueous phase.

The work of Song et al. is distinguishable from the work in the present case. Typically, the hydrogels of the present case are prepared from polymerizable compositions where the total monomer concentration, $C_{mon}$, is high, such as at least 0.5 M. In contrast, Song et al. describe the use of an aqueous composition where the monomers are present at a total concentration of 21 mM. The hydrogels produced by the methods of the invention have high mechanical strength and a high degree of chain entanglement, and such are not available where the hydrogel is prepared from a polymerizable composition having a low total monomer concentration, such as below 0.5 M.

The microgels described by Song et al. are small, and have a diameter of from 400 to 900 nm (depending upon the temperature). In contrast, the hydrogels of the present invention may be prepared on a macroscale, for example with μm and mm dimensions.

Song et al. do not disclose the rheological properties of the microgels. Thus, there are no reported storage or loss moduli values, no reported stress studies, and no reported tan (δ) values. There is also no suggestion that the microgels could or would be useful for biomaterial applications, or for use as adhesives. Song et al. do no show or suggest that the microgels have self-healing properties.

A hydrogel dual network may also be formed in one step from the polymerizable composition, with the inclusion of an appropriate crosslinking agent within the composition. In earlier reported work, such as WO 2013/124654, it was necessary to first prepare polymers having suitable guest functionality, then form a supramolecular hydrogel using those polymers, and then finally to generate the covalent crosslinks within that hydrogel.

The hydrogel dual network has increased tensile strength, toughness and elasticity compared with conventional covalently cross-linked materials. The behaviour of the hydrogels are similar to those of structural proteins, which exploit similar mechanisms of action, mainly through force-induced unfolding and reversible re-folding of the modular domains, to achieve desirable mechanical properties and functions. The dual network hydrogels are highly stretchable and tough, and show highly efficient energy dissipation, and can be fully self-repaired upon relaxation through the reformation of the host-guest ternary complexes. This combination of both dynamic CB[n] host-guest interaction and covalent crosslinks within one material allows for the construction of biomimetic supramolecular materials, for myriad applications, including artificial muscles, cartilage replacement and tissue engineering, sensors, drug-delivery systems, wearable electronic devices, micro-actuators and matrices for bioseparation.

The hydrogel dual network compares favourably with the structural protein titin, which the present inventors had in mind as a representative biological material suitable for absorbing energy. The skeletal muscle protein titin (3 MDa, 1 mm long) dominates the mechanical strength and toughness of muscles. The ability of titin to absorb energy, by force-induced rupture of secondary intramolecular interactions, has been previously revealed by single molecule force spectroscopy studies. The unfolding of titin unfolding is followed by refolding-induced shape recovery, making it an intriguing model for the design of artificial adaptive materials.

The hydrogel dual networks described herein, consisting of permanent as well as temporary non-covalent interactions, closely mimics titin's topological architecture. In this respect the hydrogels provide an improvement over the biomimetic systems described to date. For example, Guan et al. reported a biomimetic system incorporating supramolecular quadruple hydrogen bonding moieties, 2-ureido-4[1 H]-pyrimidone (UPy), as modular units, mimicking immunoglobulin (Ig)-like domains. UPy-based materials, however, are difficult to incorporate into aqueous systems unless segmented amphiphilic UPy-tethered polymers are used. The as-formed fibres in an aqueous solution are able to cross-link and generate transient supramolecular networks.

Song et al. do not describe a hydrogel having a dual network. Polymer chains in the microgels described by this group are linked only via a supramolecular non-covalent complex.

WO 2015/103125 describes the use of cucurbituril to form polymer films. Here, the cucurbituril is covalently connected to polymerizable functionality, such as an alkenyl group, for co-polymerization with an organic monomer also containing an alkenyl group.

The cucurbituril-containing monomer is used only to form covalent connections, and there is no disclosure of a non-covalent complex formed between cucurbituril and guest molecules provided by the polymerizable organic monomers. Further, the polymerizable compositions described in WO 2015/103125 contain organic solvents, and there is no suggestion that a polymer could be prepared in water to give a hydrogel product.

Similarly, CN 104086691 describes the use of a cucurbituril provided with polymerizable functionality. This polymerizable monomer was obtained from the reaction of monofunctional CB-OH with 4-benzyl chloride. Subsequent reaction of the CB-containing monomer with a comonomer provided a polymer product. The cucurbituril is used to host an imidazolium-containing compound, however this compound is not a polymerizable monomer, and it is not contained within the backbone of the polymer formed from the polymerisation of the modified cucurbituril with 4-vinylbenzyl chloride. In the present case, polymer molecules are non-covalently linked via cucurbituril-based host-guest complexes. Such are not present in the polymer products of CN 104086691.

CN 105061783 broadly describes polymerizable compositions comprising a host, such as cyclodextrin or cucurbituril, together with the polymerizable monomers 1-vinylimidazole and hydroxypropyl acrylate. The composition is polymerized to give a polymer product.

The authors of CN 105061783 refer to their product as a self-healing gel. The connections formed by the cyclodextrin or cucurbituril compounds in the polymerizable composition and the gel product are not clearly described, and no analytical data is provided.

The polymers of the present case are non-covalently connected via a cucurbituril-based host-guest complex. Here, guest molecules on the polymer are held in the cavity of the cucurbituril host in a supramolecular complex, thereby forming non-covalent links between polymer chains. The guest-bearing portions of the polymer are derived from polymerizable monomers that are provided with suitable guests in a precursor polymerizable composition. A host-guest complex is not explicitly described in CN 105061783. Moreover, it is believed that the monomers described in CN 105061783 are incapable of forming a host-guest complex, as they do not possess suitable functionality. It is suggested that the polymer product contains non-covalent binding between the cucurbituril and the imidazole group provided by the monomer. However, where such binding is present, this can only be binding between the cucurbituril portals and the imidazole group. This is not a complex in the meaning of the present case, where the cucurbituril hosts one or more guests in its cavity.

Without wishing to be bound by theory, the present inventors believe that the imidazolyl group provided by the 1-vinylimidazole monomer cannot extend into the cavity of the cucurbituril as it is connected directly to the vinyl polymerizable group that forms the backbone of the polymer product. In the present case, the inventors exemplify the use of the idazolium-containing polymerizable monomer 1-benzyl-3-vinylimidazolium together with CB[8]. Here, the benzyl group is located in the cavity of the cucurbituril host, whilst the imidazolium group is located at the portals (see FIG. 5)

In the present case, the presence of a host-guest complex is seen from the analysis of the NMR spectrum of a supramolecular polymer product. The presence of a host-guest complex may be confirmed by other methods, such as UV-vis spectroscopy, as is known to the skilled person.

The polymerizable composition in CN 105061783 is apparently prepared and used without solvent. In contrast, in the preferred embodiments of the present case, the polymerizable composition is an aqueous composition for use in the preparation of a hydrogel product.

A recent publication from Xu et al., which was published after the priority date of the present case, describes supramolecular hydrogels prepared from CB[8] and polymerizable monomers. This work is from the same groups as Song et al. described above. Here, an aqueous polymerizable composition is prepared from CB[8] complexed with FGG-EA and acrylamide (AAm). The polymerisation of this composition yields a supramolecular hydrogel. The authors show that increasing the amount of acrylamide in the composition, therefore increasing the total monomer concentration in the composition, improves the storage and loss moduli, as well as the complex shear modulus. As expected, the hydrogel may be broken by the introduction of a competitive binder, here memantine, to disrupt the CB[8] supramolecular complex.

The work of Xu et al. is therefore supportive of the earlier work described and claimed in the present case.

Polymerizable Composition

The present invention provides a polymerizable composition comprising a cucurbituril and a first polymerizable monomer, where the first polymerizable monomer has guest functionality suitable for participating in a host-guest complex with the cucurbituril. The polymerizable composition may be an aqueous composition, and the aqueous composition may be used to prepare the hydrogel of the invention. In other aspects the polymerizable composition may be used to prepare a polymer. Here it is not necessary for the composition to be an aqueous composition. Typically, the total monomer concertation in the polymerizable composition is at least 0.5 M.

The first monomer provides a guest for the formation of host-guest complexes in the supramolecular network. The amount of guests present in the polymerizable composition, and therefore the amount of first monomer present, together with the amount of cucurbituril host, will therefore dictate the level of crosslinking in the network. Typically the first monomer is provided together with other polymerizable monomers that do not participate in the formation of host-guest complexes.

As discussed in further detail below, a third monomer may be provided in the polymerizable composition, and this monomer may also have guest functionality suitable for participating in a host-guest complex with the cucurbituril. The third monomer differs to the first monomer.

The cucurbituril may be in a complex with one or two guests of the first polymerizable monomer and/or a third monomer, where present. Thus, the polymerizable composition may contain ternary host-guest complexes or binary host-guest complexes, where the guests are provided by the monomer in the polymerizable composition.

At least some of the cucurbituril is in complex with a monomer guest or guests provided within the polymerizable composition. For example, at least 5%, such as at least 10%, such as at least 20%, such as at least 25%, such as at least 50%, such as at least, 75%, such as at least 95%, of the cucurbituril is in complex with a guest or guests provided within the polymerizable composition. Substantially all of the cucurbituril in the polymerizable composition may be in a guest-host complex.

The polymerizable composition may comprise one or more further polymerizable monomers, as discussed in further detail below. Each of these further polymerizable monomers differs from the first polymerizable monomer.

A second monomer may be present in the polymerizable composition, for polymerization with the first monomer. The second monomer differs from the first monomer. A second monomer does not have guest functionality suitable for participating in a host-guest complex with the cucurbituril. Typically the second monomer is provided as a structural element for the product polymer, which polymer forms the basis of the extended network in the hydrogel product.

Typically the second monomer is present in the polymerizable composition. The second monomer may also be present in excess of the first monomer. The hydrogels of the present invention have excellent rheological properties even when the amount of first monomer is relatively low compared with the amount of second monomer. Thus, it is not essential for the amount of crosslinking to be very high.

The second monomer may be present at an equimolar amount or more with respect to the mole amount of the first monomer.

The second monomer may be present in a mole amount that is 2 times or more, 5 times or more, 10 times or more, or 15 times or more than the mole amount of the first monomer.

The first monomer should also be present at a level to provide sufficient non-covalent crosslinking within the hydrogel to provide the desirable physical characteristics of toughness and strechability. Thus, the second monomer may be present in a mole amount that is at most 25 times, at most 30 times, at most 50 times, or at most 100 times more than the mole amount of the first monomer.

In the worked examples, a second monomer is used at 95 mole equiv. to 5 mole equiv. of a first monomer, thus the second monomer is present in a mole amount that is 19 times the mole amount of the first monomer.

A third monomer may be provided in the polymerizable composition, where the third monomer differs from the first monomer, and also from the second monomer, where present. The third monomer has guest functionality suitable for participating in a host-guest complex with the cucurbituril. The guest functionality may the same as the guest functionality of the first monomer, or it may be different. In the former case, where the guest functionality is the same, the remaining part of the third monomer differs from the first monomer. Here, the guests of the first and third monomers may form ternary complexes together, and may also form separate complexes. A hydrogel formed from a composition containing such monomers may therefore have a mixture of complexes.

Where the third monomer has different guest functionality to the first monomer, the first and third monomers may be used together to form ternary complexes, for example, where the guests in the complex are different (referred to as a 1:1:1 complex of the guests with the cucurbituril host). Suitable mixed guest pairings as described in the cucurbituril guest section below. Additionally or alternatively, the monomer guests of the first and third monomers may form separate complexes, where the guests in each complex are the same (a 2:1 complex of the guests with the host), and the hydrogel formed from a composition containing such monomers may therefore have a mixture of complexes.

Where a third monomer is present, it may be present in a mole amount that is more than or less than, or the same as the mole amount of the first monomer.

Typically the third monomer is present only when there is a second monomer present in the polymerizable composition. Here, the second monomer may be present at an equimolar amount or more with respect to the mole amount of the third monomer.

The second monomer may be present in a mole amount that is 2 times or more, 5 times or more, 10 times or more, 15 times or more than the mole amount of the third monomer.

The third monomer should also be present at a level to provide sufficient crosslinking within the hydrogel to provide the desirable physical characteristics of toughness and strechability. Thus, the second monomer may be present in a mole amount that is at most 20 times, at most 25 times, at most 30 times, at most 50 times, or at most 100 times or more than the mole amount of the third monomer.

Alternatively, the second monomer may be present at an equimolar amount or more with respect to the combined mole amount of the first monomer and the third monomer (where such are both present in the polymerizable composition).

The second monomer may be present in a mole amount that is 2 times or more, 5 times or more, 10 times or more, 15 times or more than the combined mole amount of the first monomer and the third monomer.

The first and third monomer should also be present at a level to provide sufficient crosslinking within the hydrogel to provide the desirable physical characteristics of toughness and strechability. Thus, the second monomer may be present in a mole amount that is at most 20 times, at most 25 times, at most 30 times, at most 50 times, or at most 100 times than the combined total mole amount of the first monomer and the third monomer.

A fourth monomer may be provided in the polymerizable composition, where the fourth monomer is a crosslinking monomer (also referred to as a crosslinker). For example, the monomer is a polyfunctional monomer, such as a bifunctional monomer. The fourth monomer may be used to provide additional covalent crosslinks between polymers, in addition to the non-covalent crosslinks provided by the cucurbituril complex (provided by the first monomer, and the third monomer, where present).

Where a crosslinker is present, the crosslinker is typically provided at a relatively low mole amount with respect to the mole amount of first monomer and the second monomer, where present, such as with respect to the amount of first monomer. The inventors have found that hydrogels having excellent fracture resistance and fatigue resistance are obtainable in systems where the level of covalent crosslinking is relatively low. Thus, the non-covalent crosslinks in the hydrogel may be in excess of the covalent crosslinks, and therefore the amount of first monomer is typically in excess of the fourth monomer.

The first monomer may be present at an equimolar amount or more with respect to the mole amount of the fourth crosslinking monomer.

The first monomer may be present in a mole amount that is at least 2 times, at least 5 times, or at least 10 times the mole amount of the fourth monomer.

The fourth monomer should be present at an amount to provide covalent crosslinking within the hydrogel at a level that will give the desirable physical characteristics of fracture resistance and fatigue resistance. Thus, the first monomer may be present in a mole amount that is at most 20 times, at most 25 times, at most 50 times, at most 100 times or at most 150 times the mole amount of the fourth monomer.

In the worked examples, a crosslinking monomer is used at 0.05 mole equiv. to 5 mole equiv. of a first monomer, thus the first monomer is present in a mole amount that is 100 times the mole amount of the crosslinking monomer.

In the present case, the inventors have prepared a hydrogel having only non-covalent cross-links, and also a hydrogel having both non-covalent and covalent cross-links (the latter referred to as a dual network). The addition of covalent cross-links to the hydrogel provides structural integrity to the hydrogel, and also imparts a degree of elasticity to the hydrogel. The fourth monomer is therefore provided when the hydrogel product is required to have both non-covalent and covalent cross links.

The additional covalent bonding provides useful additional characteristics to the hydrogel and complements the benefits that are available to those hydrogels having non-covalent bonding.

The non-covalent supramolecular host-guest interactions are believed to perform several mechanical functions simultaneously. For example, the non-covalent interactions enhance the fracture resistance of the material through sacrificial bond rupture, thereby toughening the network. The presence of the supramolecular complex all enhances energy dissipation by generating high internal friction. In the dynamic system, ruptured bonds are capable of re-forming, thereby healing the material after damage. In this way fatigue resistance is enhanced.

Optionally, the cucurbituril is a group within a fifth polymerizable monomer. Here, the cucurbituril is covalently bonded, either directly or indirectly to the polymerizable functionality of the fifth monomer. In preferred embodiments, the cucurbituril is not a group within a polymerizable monomer. Thus, preferably a fifth polymerizable monomer is not present in the polymerizable composition.

Other polymerizable monomers may be provided in the composition. For example, monomers comprising detectable labels may also be provided in the polymerizable composition. In this way, the hydrogel may incorporate labels, for example for detection and analysis of the hydrogel product.

The type of label is not particularly limited, and may include fluorescent or luminescent labels, for example. In the worked examples of the present case, fluorescent monomers are used in the polymerizable composition to provide a fluorescent hydrogel. The inventors have used the fluorescent labelling to following the formation of dynamic links between contacting hydrogels, leading to the unification of contacting hydrogel pieces.

The polymerizable composition may comprise additional components intended to control the polymerization reaction, and/or to modify the properties of the product hydrogel.

The polymerizable composition may also include a catalyst or polymerization initiator to control or initiate the polymerization reaction.

The polymerizable composition may be prepared by simple admixing of the components, for example in water. The order of addition may be controlled in order to control the later polymerization of the composition.

Within the polymerizable composition the cucurbituril is typically in a non-covalent complex with the guest of the first monomer. This may be a binary complex or a ternary complex. Here, when the polymerization reaction proceeds, the first monomer reacts whilst in complex with the cucurbituril, and a first monomer compound may also be non-covalently linked to another first monomer compound through the complex. The complex may continue to provide a connection between the growing polymer chains that extend from the first monomer compounds, and ultimately the complex is present in the final hydrogel product providing the non-covalent connection between the formed polymers.

An aqueous polymerizable composition typically has a total monomer concentration, $C_{mon}$, of at least 0.2 M, at least 0.3 M, at least 0.5 M, at least 1.0 M, at least 1.5 M, at least 2.0 M. The inventors have found that the mechanical properties of the hydrogel are most useful when the total monomer concentration is relatively high, for example where the concentration is at least 1.0 M, and most preferably at least 2.0 M. At these higher concentrations, the chain entanglement in the resulting hydrogel is higher, and this provided a beneficial contribution to the mechanical strength of the hydrogel.

The aqueous polymerizable composition typically has a total monomer concentration, $C_{mon}$, of at most 5.0 M, at most 10.0 M or at most 20 M.

The total monomer concentration may be an amount in a range with the lower and upper amounts selected from the values given above. For example, the total monomer concentration may be in the range 0.5 to 5.0 M.

The total monomer concentration refers to the total mole amount of polymerizable monomers, such as sum of the first to fifth monomer amounts, present in the polymerizable composition.

The cucurbituril and the first monomer, where present with other polymerizable monomers, need not be present in high quantities. The hydrogels of the present invention retain their stretching and healing properties when the level of dynamic cross-linking (the amount of non-covalent bonding provided by the cucurbituril complex) is relatively low. It follows that the third monomer, where present, also need not be present in high quantities.

An aqueous polymerizable composition typically has a cucurbituril concentration of at least 0.005 M, at least 0.01 M, at least 0.02 M, at least 0.05 M, at least 0.1 M.

An aqueous polymerizable composition typically has a cucurbituril concentration of at most 0.5 M, at most 1.0 M, or at most 2.0 M.

The concentration of cucurbituril may be present in a range with the lower and upper amounts selected from the values given above. For example, the cucurbituril may be present at a concentration in the range 0.01 to 0.5 M.

Where the cucurbituril is intended to form a ternary supramolecular complex, it is typically present at around half the mole amount of the first monomer, and the third monomer, where present. Here, cucurbituril may be present in an amount of at least 0.25 mole %, at least 0.5 mole %, at least 1.0 mole %, at least 2.5 mole % with respect to the total monomer amount. The cucurbituril may be present in an amount of at most 5.0 mole %, at most 7.5 mole %, at most 10 mole %, at most 12.5 mole %, or at most 25 mole % with respect to the total monomer amount.

The cucurbituril may be present in an amount in a range with the lower and upper amounts selected from the values given above. For example, the cucurbituril may be present in an amount in the range 0.5 to 5 mole %.

Where the cucurbituril is intended to form a binary supramolecular complex, it is typically present at around the same mole amount as the first monomer, and the third monomer, where present. Here, the cucurbituril may be present in an amount of at least 0.5 mole %, at least 1 mole %, at least 2 mole %, at least 5 mole % with respect to the total monomer amount. The cucurbituril may be present in an amount of at most 10 mole %, at most 15 mole %, at most 20 mole %, at most 25 mole %, or at most 50 mole % with respect to the total monomer amount.

The cucurbituril may be present in an amount in a range with the lower and upper amounts selected from the values given above. For example, the cucurbituril may be present in an amount in the range 1 to 10 mole %.

The polymerizable composition may further comprise a catalyst or a polymerization initiator.

The catalyst or a polymerization initiator may be present in an amount of at least 0.01 mole %, at least 0.05 mole %, at least 0.1 mole %, at least 0.5 mole % with respect to the total monomer amount, $C_{mon}$.

The catalyst or a polymerization initiator may be present in an amount of at most 1 mole %, at most 2 mole % or at most 5 mole % with respect to the total monomer amount, $C_{mon}$.

The catalyst or a polymerization initiator may be present in an amount in a range with the lower and upper amounts selected from the values given above. For example, the catalyst or a polymerization initiator may be present in an amount in the range 0.01 to 1 mole %.

Monomers

The polymerizable composition contains one or more monomers, which monomers are suitable for reaction in a polymerization reaction to form a polymer product.

In a preferred embodiment, the composition comprises two or more monomers. The first monomer, having guest functionality, is intended to provide non-covalent cross-links in the hydrogel product. The first monomer is typically present together with a second monomer, which is intended to provide the structural backbone to the hydrogel material.

Optionally a fourth monomer may be present, which monomer is a crosslinker, which is intended to provide covalent cross-links in the product.

The monomers are not particularity limited, so long as the monomer contains suitable functionality for participating in a polymerization reaction. The monomers may be suitable for polymerizing under step growth or chain growth conditions. The monomers may be suitable for polymerizing under radical, cation or anion (addition) polymerization conditions. The monomers are typically suitable for use in polymerization reactions under aqueous conditions.

The monomers may be suitable for participating in a radical polymerization reaction. In the worked examples of the present case, radical polymerization is used to prepare a hydrogel product.

In one embodiment, the monomers for use in the polymerizable composition include a carbon-carbon double or triple bond, and most preferably a carbon-carbon double bond.

A carbon-carbon double or triple bond may be present at a terminal of the monomer, thus a monomer, such as the first or second monomer, may have a vinyl (ethylene) group, such as an allyl group, or an acetylenyl (ethynyl) group, such as a propargyl group. The carbon-carbon double or triple bond may be available for reaction in a polymerization reaction.

Other functionalities may be used in place of carbon-carbon double or triple bond, such as acid and amine functionalities for the formation of polyamides, amongst others.

Typically the alternative functionalities for use in the present case are those where polymerization may be achieved in water, to give a hydrogel product. Examples include Michael addition reactions between monomers with thiol and alkene, such as vinyl, functionalities; esterification and amidation reactions monomers with acid functionality, or an activated form of the acid such as an anhydride, and alcohol or amine functionality; ring opening reactions using monomers having epoxy groups and alcohol, amine or carboxy functionality; Schiff-base reactions between monomers having aldehyde and hydroxy or carboxy functionality; and Click reactions, for example between monomers having azide and alkyne functionality.

Where there are two or more different monomers in the polymerizable composition, the monomers have functionality to react with one another in a polymerization reaction. The different monomers may have the same functionality (for example, vinyl functionality) or may have different functionality (for example, amino functionality on one monomer, carboxyl functionality on another monomer).

The first monomer is typically a vinyl monomer, where the guest is a substituent to the vinyl group. Suitable guests are described in further detail below. In the worked examples of the present case, the first monomer is 1-benzyl-3-vinylimidazolium.

The monomers for use in the polymerizable composition, such as those for use as second monomers, may be acrylate-based or acrylamide-based monomers. Examples here include acrylate and acrylamide monomers, alkylacrylate monomers, such as methacrylate monomers, and alkylacrylamide, such as methacrylamide monomers, and (alkyl)acrylate monomers, such as (methyl) and (alkyl)acrylamide, such as (methyl)acrylamide monomers.

In one embodiment, acrylate-based monomers are less preferred, for example it is preferred that the first monomer and the third monomer, where present, are not an acrylate-based monomer, such as the first and the third monomer, where present, do not include an acrylate group (—OC(O)CHCH$_2$). Nevertheless, acrylate-based monomers may still find use in the present invention, and such may be used as the second monomer, for use in preparing hydrogels having desirable rheological properties. The worked examples in the present case show the use of acyclic acid and other acrylate-based monomers as a second monomer.

The monomers present in the polymerizable composition may be at least partially soluble in water. The monomers may be hydrophilic monomers.

A monomer may have a solubility in water of at least 1 g/L, such as at least 5 g/L, such as at least 10 g/L, and such as at least 15 g/L.

The water solubility information may be provided from a commercial supplier of the monomer, or may be determined by experimental methods, such as those known to those of skill in the art. Solubility may be determined at 25° C. The worked examples of the present case make use of methacrylate monomers, and the monomer methyl methacrylate has a solubility of about 15 g/L at 25° C.

Preferably, the first monomer is a vinyl monomer. As shown herein, a guest molecule may be connected to a vinyl group, and this monomer may participate in a polymerization reaction to form a supramolecular hydrogel.

The second monomer may be a vinyl monomer, and particularly a substituted vinyl monomer, such as those that are substituted with amido groups, such as acrylamide monomers, or ester groups, such as acrylate monomers, or heteroaryl groups, such as imidazolium monomers.

Preferably, the second monomer is an acrylamide-based monomer, such as acrylamide.

Additionally or alternatively, the second monomer is an (alkyl)acrylamide-based monomer, an (alkyl)acrylate-based monomer, such as an (alkyl)acrylate-based monomer, or an aryl vinyl monomer, such as a 1-vinyl-3-ethylimidazolium monomer.

Examples of (alkyl)acrylamide monomers include (alkyl) acrylamide, alkyl (alkyl)acrylamides such as dimethyl acrylamide (DMA), diethyl acrylamide, N-isopropyl acylamide (NIPAm) and N-tert-butyl acrylamide; and hydroxyalkyl acrylamides, such as N-hydroxyethyl acrylamide (HEAm), N-[tris(hydroxymethyl)methyl] acrylamide and 2-hydroxypropyl methacrylamide; sulfonylalkyl (alkyl)acrylamides such as 2-acrylamido-2-methyl-1-propanesulfonic acid; aminoalkyl (alkyl)acrylamides such as N-(3-aminopropyl) methacrylamide; An (alkyl)acrylamide monomer may be an acrylamide monomer.

Examples of (alkyl)acrylate monomers include acrylic acid, alkyl (alkyl)acrylates, such as 2-ethylhexyl methacrylate and ethyl methacrylate; aminoalkyl (alkyl)acrylates, such as 2-(dimethylamino)ethyl methacrylate (DMAEMA) and 2-(diisopropylamino)ethyl methacrylate; hydroxyalkyl (alkyl)acrylates such as 2-hydroxyethyl methacrylate; (hydroxy)heteroalkyl (alkyl)acrylates such as poly(ethylene glycol) methacrylate (PEGMA), ethylene glycol methyl ether methacrylate and 2-ethoxyethyl methacrylate; sulfonyl (hetero)alkyl (alkyl)acrylate such as 3-[2-(methacryloyloxy)ethyl](dimethyl)ammonio-1-propanesulfonate (MPS) and 3-sulfopropyl methacrylate.

An (alkyl)acrylate monomer may be an alkylacrylate monomer, such as a methacrylate monomer.

Examples of aryl vinyl monomers include heteroaryl vinyl monomers, such as imidazole monomers, such as 1-vinylimidazole and 1-vinyl-3-ethylimidazolium (ViEt).

The worked examples in the present case demonstrate the use of acrylamide (AAm), N-isopropylacrylamide (NIPAm), 2-(dimethylamino)ethyl methacrylate contains (DMAEMA), acrylic acid (AA), 1-vinyl-3-ethylimidazolium bromide (ViEt), 3-[2-(methacryloyloxy)ethyl](dimethyl)ammonio-1-propanesulfonate (MPS), poly(ethylene glycol) methacrylate (PEGMA), dimethylacrylamide (DMA) and N-hydroxyethyl acrylamide (HEAm) as second monomers in polymerizable compositions.

The polymerizable composition may contain multiple monomers having guest functionality for cucurbituril, such as the polymerizable composition may contain the first monomer together with the third monomer. Here, the guest functionality of each of the monomers may form non-covalent complexes with cucurbituril.

In other embodiments, the first monomer may be provided with a second monomer in the polymerizable composition, where the second monomer has functionality that is capable of forming a complex with cucurbituril in the absence of the first monomer, but does not do so when the first monomer is present. In this composition the binding affinity of the first monomer guest for cucurbituril is greater, such as very much greater, than the binding affinity of the second monomer functionality for cucurbituril.

Thus, complex formation may be predominately between cucurbituril and the first monomer guest.

The worked examples in the present case include a polymerizable composition containing 1-benzyl-3-vinylimidazolium as the first monomer, and 1-vinyl-3-ethylimidazolium (ViEt) as the second monomer. The benzyl-imidazolium moiety exhibits much stronger binding to cucurbituril than the ethylimidazolium group of the second monomer, therefore complex formation is predominantly, if not entirely, between cucurbituril and the first monomer.

In one embodiment, a monomer in the polymerizable composition is a salt. Thus, a monomer has an ionic group and a counter ion to that ionic group. The ionic group may not be present as part of the polymerizable functionality of the monomer. Thus, the ionic group is not intended to participate in the polymerization reaction. The ionic group that is present in the monomer may be present in the hydrogel product after polymerization, together with a suitable counter ion.

Preferably, the first monomer is a salt and most preferably the ionic group is provided on the guest of the first monomer. Where a third monomer is present, this may be a salt and it too may have the ionic group provided on the guest of the third monomer.

In the worked examples of the present case the fourth monomer used to provide covalent crosslinks in the hydrogel product is N,N-methylene bisacrylamide. The use of crosslinkers is routine in the art, and other bifunctional (or multifunctional) monomers may be used in place of N,N'-methylene bisacrylamide.

A guest of the first monomer is connected, such as covalently directly connected or covalently indirectly connected, to the polymerizable group, such as a vinyl group, which participates in the polymerization reaction. Suitable guests are described in further detail below.

It is preferred that the polymerizable composition contains a first monomer and a second monomer. As previously explained, the first monomer, together with cucurbituril, provides the non-covalent links in the hydrogel product. The inventors have found that strong hydrogels may be prepared where the level of non-covalent crosslinking is relatively low.

Therefore the amount of first monomer present in the polymerizable composition may also be relatively low. Accordingly, the amount of the second monomer, which provides the structural backbone to the hydrogel product, is relatively large.

A reference to total monomer amount is a reference to the combined total mole amount of all polymerizable monomers in the polymerizable composition, such as the total amount of the first monomer and the second monomer, optionally together with the third and fourth monomers, where present, and any other polymerizable monomers, where present.

The first monomer may be present in an amount of at least 0.5 mole %, at least 1 mole %, at least 2 mole %, at least 5 mole % with respect to the total monomer amount.

The first monomer may be present in an amount of at most 10 mole %, at most 15 mole %, at most 20 mole %, at most 25 mole %, or at most 50 mole % with respect to the total monomer amount.

The first monomer may be present in an amount in a range with the lower and upper amounts selected from the values given above. For example, the first monomer may be present in an amount in the range 1 to 10 mole %.

Preferably, the second monomer is present in the polymerizable composition. Typically the second monomer is present in large excess with respect to the first monomer.

The second monomer may be present in an amount of at least 50 mole %, at least 60 mole %, at least 70 mole %, at least 80 mole %, at least 90 mole %, at least 95 mole % with respect to the total monomer amount.

The second monomer may be present in an amount of at most 96 mole, at most 98 mole % or at most 99 mole % with respect to the total monomer amount.

The second monomer may be present in an amount in a range with the lower and upper amounts selected from the values given above. For example, the second monomer may be present in an amount in the range 90 to 99 mole %.

A third monomer, where present, will typically be present in an equimolar amount to the first monomer.

A guest of the third monomer is connected, such as covalently directly connected or covalently indirectly connected, to the polymerizable group, such as a vinyl group, which participates in the polymerization reaction. Suitable guests are described in further detail below.

The total mole amount of the first and third monomers may be selected from the values given above for the first monomer.

Thus, the total mole amount of the first and third monomers may be at least 0.5 mole %, at least 1 mole %, at least 2 mole %, at least 5 mole % with respect to the total monomer amount.

Thus, the total mole amount of the first and third monomers may be at most 10 mole %, at most 15 mole %, at most 20 mole %, at most 25 mole %, or at most 50 mole % with respect to the total monomer amount.

The first and third monomers may be present in an amount in a range with the lower and upper amounts selected from the values given above. For example, the first and third monomers may be present in a combined amount in the range 1 to 10 mole %.

The amount of cucurbituril present in the composition may be selected taking into account the total mole amount of monomers present in the composition having guests for forming complexes. Where the hydrogel will contain ternary complexes, the mole amount of cucurbituril present in the composition will be about 50% of the total mole amount of monomers present in the composition having guests for forming complexes, which may be the amount of first monomer present, or may be the total mole amount of the first and third monomers present.

Where the hydrogel contains binary complexes, the mole amount of cucurbituril present in the composition will be equimolar to the total mole amount of monomers present in the composition having guests for forming complexes, which may be the amount of first monomer present.

The first and/or third monomers may have one or more, such as two, guests for cucurbituril. Typically the first and the third monomer have only one guest.

A fourth monomer, where present, may be present at relatively low amounts. As previously explained, the fourth monomer provides covalent links in the hydrogel product.

The inventors have found that useful hydrogels may be prepared where the level of covalent crosslinking is relatively low. Therefore the amount of fourth monomer present in the polymerizable composition may also be relatively low. Again, amount of the second monomer, which provides the structural backbone to the hydrogel product, is relatively large.

The fourth monomer may be present at relatively low amounts within the polymerizable composition.

The fourth monomer may be present in an amount of at least 0.01 mole %, at least 0.05 mole %, at least 0.1 mole %, at least 0.5 mole % with respect to the total monomer amount.

The fourth monomer may be present in an amount of at most 1 mole %, at most 2 mole % or at most 5 mole % with respect to the total monomer amount.

The fourth monomer may be present in an amount in a range with the lower and upper amounts selected from the values given above. For example, the fourth monomer may be present in an amount in the range 0.01 to 1 mole %.

In some embodiments a fifth polymerizable monomer is present in the polymerizable composition, where the fifth monomer comprises a cucurbituril. The cucurbituril is connected, such as covalently directly connected or covalently indirectly connected, to a polymerizable group, such as a vinyl group, which may participate in the polymerization reaction. Typically the fifth monomer is used in an equimolar amount to the amount of the first monomer.

The total mole amount of the first and fifth monomers may be selected from the values given above for the first monomer.

Thus, the total mole amount of the first and fifth monomers may be at least 0.5 mole %, at least 1 mole %, at least 2 mole %, at least 5 mole % with respect to the total monomer amount.

Thus, the total mole amount of the first and fifth monomers may be at most 10 mole %, at most 15 mole %, at most 20 mole %, at most 25 mole %, or at most 50 mole % with respect to the total monomer amount.

The first and fifth monomers may be present in an amount in a range with the lower and upper amounts selected from the values given above. For example, the first and fifth monomers may be present in a combined amount in the range 1 to 10 mole %.

A monomer in the polymerizable composition may have a molecular weight of at least 50, at least 100, or at least 200.

A monomer in the polymerizable composition may have a molecular weight of at most 500, at most 1,000, of at most 1,500 or at most 2,000.

A reference to a monomer may also include a reference to an oligomer, such as might be formed from the reaction of a small number of monomers. An oligomer has at most 50 repeat monomer units, such as at most 20 repeat units, such as at most 10 repeat units, such as at most 5 repeat units, such as at most 2 repeat units (dimers). The present inventors realise that the advantages of the invention are obtainable where small molecular weight starting materials are used to together in a polymerization reaction together with a cucurbituril host.

In one embodiment, a reference to a monomer is a reference to a monomer only, and does not include oligomeric forms.

Complex

The hydrogel is a polymer network that is held together by a supramolecular handcuff.

The complex that forms this supramolecular handcuff is based on a cucurbituril hosting one guest (binary complex) or two guests (ternary complex). The cucurbituril forms a non-covalent bond to each guest. The present inventors have previously established that complexes of cucurbituril are readily formed and can be used to provide robust non-covalent linkages between polymer building blocks. A complex may be formed between the cucurbituril and the guest of the first monomer, and the formation of the complex is tolerant of many functionalities within the monomer.

The complex may be referred to as an inclusion complex, in recognition of the host holding one or more guests within its cavity. The complex as described herein may be distinguished from arrangements where a cucurbituril is non-covalently bound to another compound via the portals of the cucurbituril. Here, the other compound is not hosted by the cucurbituril, as the compound is not a guest within the cavity of the cucurbituril.

In methods of the present case the formation of a complex refers to the cavity of the cucurbituril receiving one or more guests, thereby to form a host-guest complex.

Figure 1B:
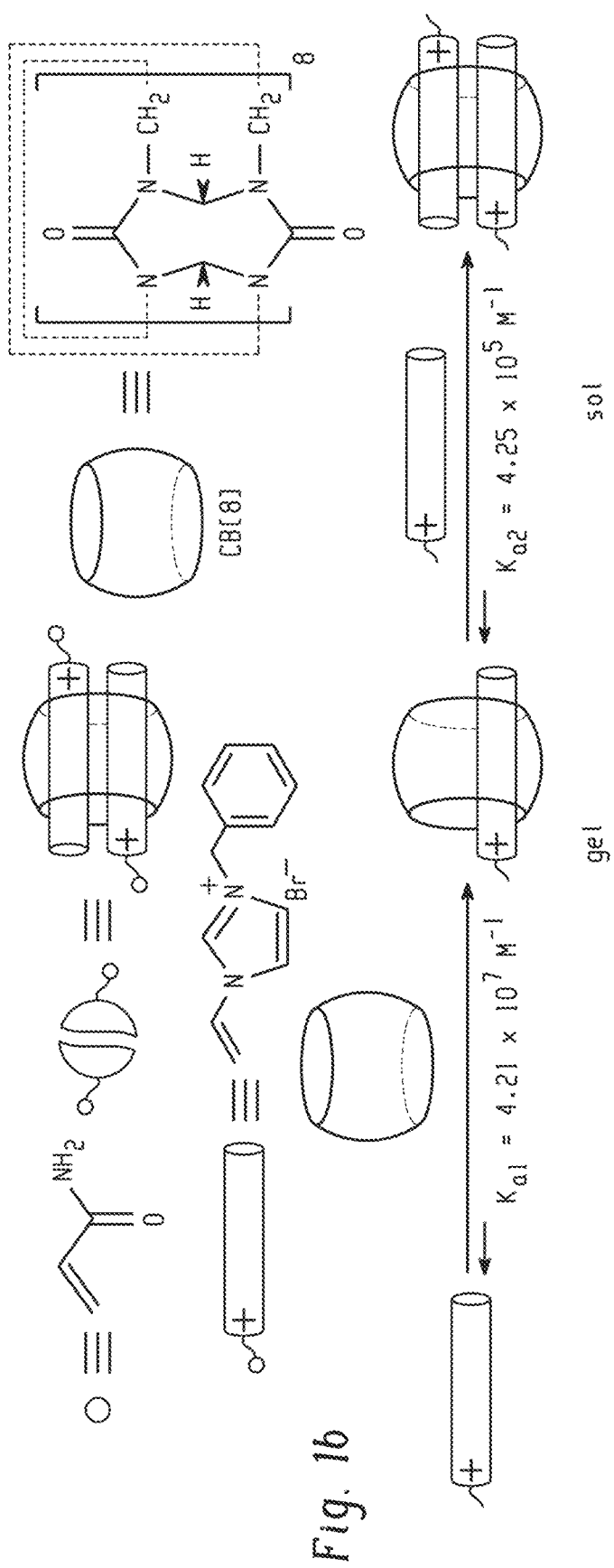
FIG. 1b is a schematic drawing of the stepwise formation of ternary host-guest complexation between CB[8] and guest molecules, following a 1:2 binding mode.

The formation of a host-guest complex is shown schematically in FIG. 1, where the cucurbituril is clearly shown holding one or more guests within the cavity.

In various embodiments of the invention, the polymer network is supplemented by the presence of covalent cross-links between polymers. Such cross-links are formed during the polymerization process when a crosslinker, such as a bifunctional monomer, is included in the polymerizable composition.

As noted above, the complex of cucurbituril with one or two guests is the non-covalent link that cross-links and/or interlinks the polymers to from a supramolecular network of material.

Where the complex comprises two guests within the cucurbituril cavity, the association constant, $K_a$, for that complex is at least $10^3$ $M^{-2}$, at least $10^4$ $M^{-2}$, at least $10^5$ $M^{-2}$, at least $10^6$ $M^{-2}$, at least $10^7$ $M^{-2}$, at least $10^8$ $M^{-2}$, at least $10^9$ $M^{-2}$, at least $10^{10}$ $M^{-2}$, at least $10^{11}$ $M^{-2}$, or at least $10^{12}$ $M^{-2}$.

Where a cucurbituril hosts two guest molecules, the guest molecules may be the same or they may be different. A cucurbituril that is capable of hosting two guest molecules may also be capable of forming a stable binary complex with a single guest. The formation of a ternary host-guest complex is believed to proceed via an intermediate binary complex. Within a hydrogel of the invention, there may be present a binary complex formed between a guest molecule and a cucurbituril. The binary complex may be regarded as a partially formed ternary complex that has not yet formed a non-covalent bond to another guest molecule.

In one embodiment, the hydrogel is a network having a plurality of complexes, wherein each complex comprises cucurbituril hosting one guest molecule.

Where the complex comprises one guest within the cucurbituril cavity, the association constant, $K_a$, for that complex is at least $10^3$ $M^{-1}$, of at least $10^4$ $M^{-1}$, of at least $10^5$ $M^{-1}$, of at least $10^6$ M$^{-1}$, of at least $10^7$ M$^{-1}$, of at least $10^8$ M$^{-1}$, of at least $10^9$ M$^{-1}$, of at least $10^{10}$ M$^{-1}$, of at least $10^{11}$ M$^{-1}$, or of at least $10^{12}$ M$^{-1}$.

In one embodiment, the guest is a compound capable of forming a complex which has an association constant in the range $10^4$ to $10^7$ M$^{-1}$.

In one embodiment the formation of the complex is reversible. The separation of a guest from the cucurbituril host, thereby to sever a link or crosslink with a polymer, may be referred to as decomplexation. In this way, the hydrogel may be regarded as a dynamic material. When the hydrogel is exposed to a stress, the complexes are believed to dissociate, and re-associate later in a healing process.

The decomplexation of the complex to separate the guest or guests may occur in response to an external stimulus, including, for example, a competitor guest compound, light, an oxidising or reducing agent, electrochemical potential, and temperature changes amongst others. The work described herein also looks at the ability of the hydrogel to respond to mechanical stresses, such as shear stress and axial stress, and the ability of the materials to respond and repair after it is stressed.

A competitive guest for use in the decomplexation of a CB[8]-based network is adamantane amine (ADA). The competitor guest may be used in excess to the amount (mole amount) of guests present on the polymers of the network. In one embodiment, the competitive guest has a higher association constant than a guest of the complex.

In other embodiments, decomplexation of the network, and therefore the hydrogel, is achieved by the oxidation or reduction of a guest in a complex. The change in oxidation state of a guest may be achieved using a chemical oxidising or reducing agent, or the application of an electrochemical potential. As described herein, a complex comprising a viologen, such as a methyl viologen, may be decomplexed by treatment with a reducing agent, such as a dithionite.

In one embodiment, the decomplexation reaction is reversible. Thus, a hydrogel may be converted to a low viscosity, decomplexed form, then returned to a high viscosity, hydrogel form, as appropriate, which may be the same or different to the original hydrogel.

Hydrogel

Hydrogels are three-dimensional cross-linked polymer networks that entrap and store large amounts of water. Given their similarity to soft biological tissues and variable mechanical properties, i.e. from soft and weak to hard and tough, they are increasingly important in a variety of biomedical and industrial applications.

The hydrogel of the invention is a three-dimensional cross-linked polymer network that holds water. In the present case, the network is obtainable or obtained from the complexation of cucurbituril hosts with suitable guest molecule functionality provided on the first monomer. Thus, the hydrogel comprises this network and entrapped water.

The hydrogel of the invention may be obtained or is obtainable from the aqueous polymerizable composition of the invention.

The hydrogel is formed from the polymerization of the polymerizable monomers in the polymerizable composition. The hydrogel formation may also include some degree of supramolecular (non-covalent) bonding between the cucurbituril host and the guest functionality provided on the monomers within the composition.

It is believed that when the cucurbituril host is mixed with the monomer in a polymerizable composition, the cucurbituril will form a complex with a guests of the polymerizable monomers, thereby serving to non-covalently link the monomers in the composition.

During polymerization, additional non-covalent links may be formed, and, given the reversible nature of the supramolecular complex, under the reaction conditions there may be some disassociation and re-association of hosts and guests.

In one embodiment, the water content of the hydrogel is at least 90 wt %, at least 95 wt %, at least 97 wt %, at least 98 wt %, at least 99 wt %, at least 99.5 wt %.

Where the water content is at such amounts, the present inventors have found that the hydrogels may be diluted, for example with a volume of water equivalent to the volume of the hydrogel, and the structure of the network remains in place. It is noted that a considerable dilution of the hydrogel may decrease the mechanical properties of the hydrogel.

In one embodiment, the total amount of polymer present in the hydrogel is at most 20 wt %, at most 10 wt %, at most 7.0 wt %, at most 5.0 wt %, at most 2.5 wt %, at most 2.0 wt %, at most 1.5 wt %, at most 1.0 wt %, at most 0.5 wt % or at most 0.4 wt %.

In one embodiment, the total amount of polymer present in the hydrogel is at least 0.05 wt %, at least 0.1 wt %, at least 0.2 wt %, at least 0.3 wt %.

In one embodiment, the total amount of polymer present in the hydrogel is in a range where the minimum and maximum amounts are selected from the embodiments above. For example, the total amount of polymer present is in the range 0.3 to 2.0 wt %.

The total amount of polymer may correspond to the total amount of polymerizable monomers contained in the polymerizable reaction, it being assumed that all the polymerizable monomers are consumed in the polymerization reaction.

During the preparation of the hydrogel, the concentration and amounts of monomers in the aqueous polymerizable composition may be selected so as to provide the desired weight amount of polymer in the hydrogel product.

The molecular weight of a polymer formed in the polymerization is not particularly limited. The worked examples of the present case demonstrate how the average molecular weight of the polymers in a hydrogel sample may be determined.

In one embodiment, the polymers in the hydrogel have a molecular weight, such as weight average $M_w$ or number average molecular weight $M_N$, of at least 50 kDa, at least 100 kDa, at least 500 kDa, at least 1.0 MDa, or at least 2.0 MDa.

In one embodiment, the polymers in the hydrogel have a molecular weight, such as weight average $M_w$ or number average molecular weight $M_N$, of at most 5.0 MDa, at most 10 MDa, at most 50 MDa or at most 100 MDa.

The polymers in the hydrogel may have an average molecular weight in a range with the lower and upper amounts selected from the values given above. For example, the hydrogel may have an average molecular weight in the range 500 kDa to 10 MDa.

Preferably, the molecular weight average refers to the weight average molecular weight, such as determined in the worked examples of the present case.

The hydrogel typically has the shape and the dimensions of the reaction vessel in which it is prepared. The hydrogels of the invention may be readily prepared on a macroscale, such as a μm, mm or cm scale.

The hydrogel may have a largest dimension of at least 1 μm, at least 5 μm, at least 10 μm, at least 20 μm, at least 50

μm, at least 100 μm, at least 500 μm, at least 1 mm, at least 5 mm, at least 1 cm, at least 100 cm.

Song et al. have described the preparation of microgels. These microgels have an average largest dimension in the range of around 400 to around 900 nm, which is dependent upon the temperature of the microgel sample.

In one embodiment, the hydrogel has a viscosity in a steady sheer measurement of at least 10, at least 100, at least 500, at least 1,000 or at least 10,000 Pa s.

In one embodiment, the hydrogel has a viscosity in a steady sheer measurement of at most 15,000, at most 20,000, at most 50,000 Pa s.

In one embodiment, the hydrogel has a viscosity in the range 100 to 15,000 Pa s, such as 1,000 to 15,000 Pa s.

Figures 9C, 9D:
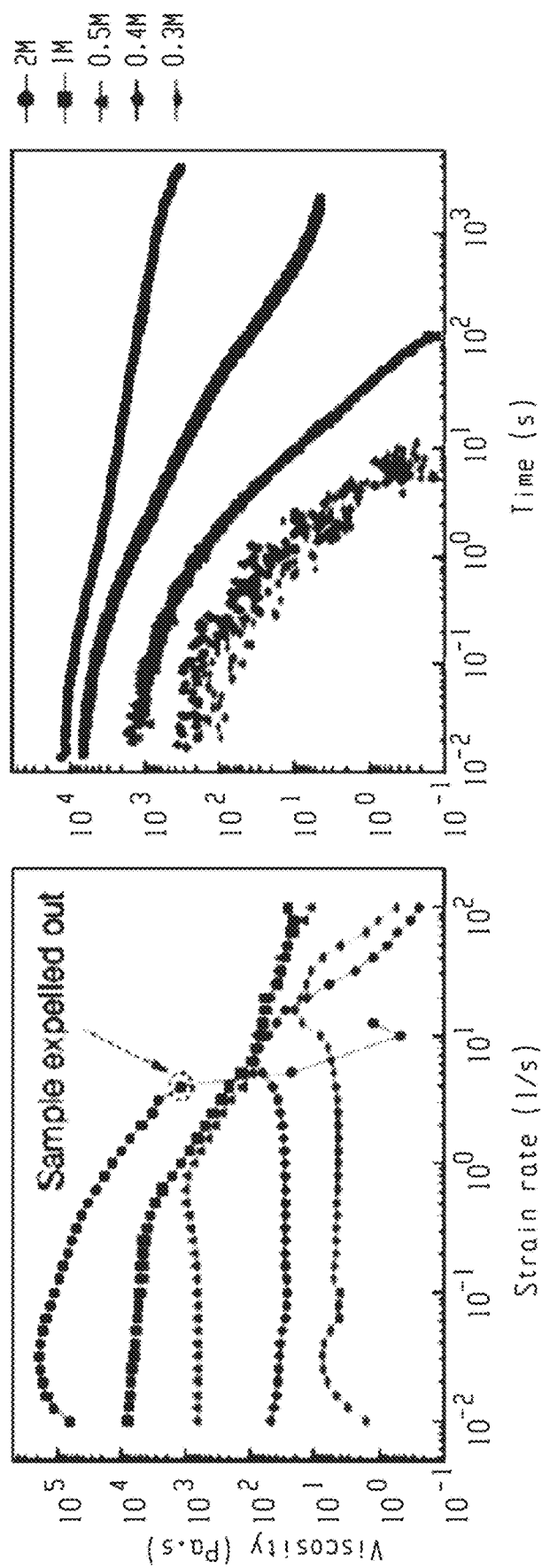
FIG. 9c shows the change in viscosity (Pa·s) with change in strain rate (1/s) for hydrogels prepared with different total monomer concentrations.
FIG. 9d shows the change in viscosity (Pa·s) with change in time (s) for hydrogels prepared with different total monomer concentrations, where the total monomer concentrations used were 0.3, 0.4, 0.5, 1.0 and 2.0 M and the stress relaxation function was G(t) as received from the step-strain experiments in the linear regime of deformation (γ=10% in 0.1 s, T=20° C.).
Figure 10A:
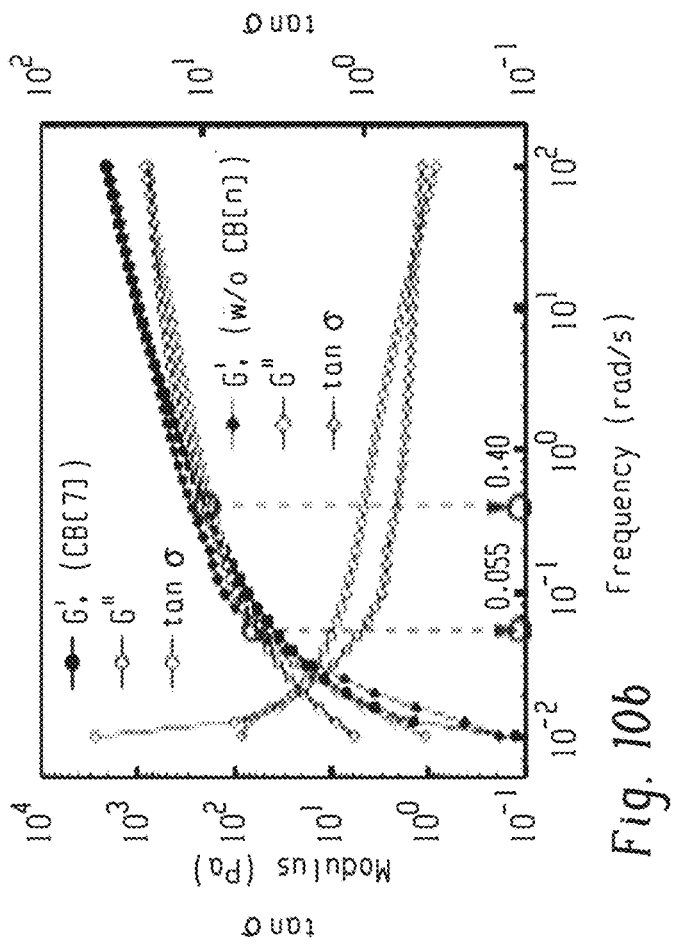
FIG. 10a shows the change in modulus (Pa) and tan (δ) for G' and G" with the change in strain (%) in a dynamic room-temperature amplitude sweep (from 0.1 to 1000% strain, 10 rad s$^{-1}$)
Figure 10B:
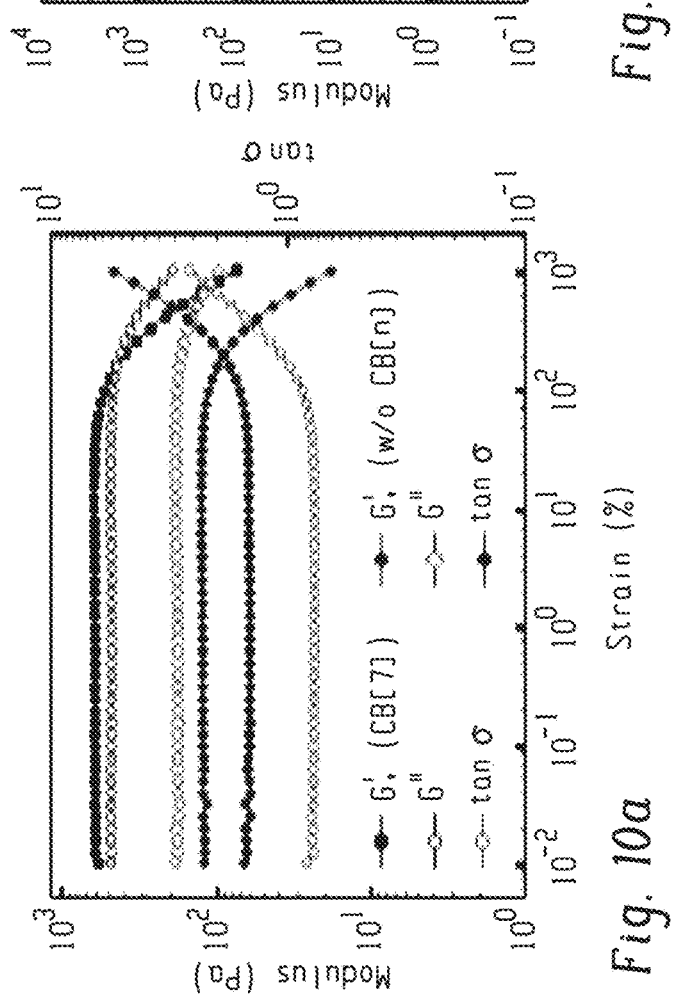
FIG. 10b shows the change in modulus (Pa) and tan (δ) for G' and G" with the change in frequency (rad/s) in a frequency sweep (from 0.01 to 100 rad s$^{-1}$, 0.5% strain.
Figure 10C:
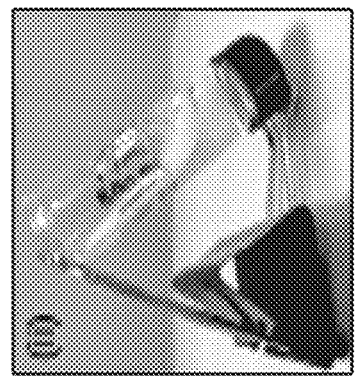
FIG. 10c is photographs of the controlled supramolecular hydrogel samples (flowing fluids) in the presence of CB[7] (c-i) and without CB[n]) (c-ii).
Figure 10C:
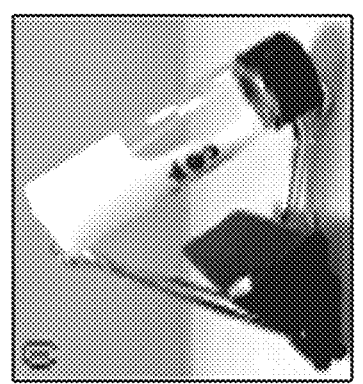

The viscosity value may be the value recorded at low shear rates, for example at a shear rate in the range 0.1 to 0.5 1/s, for example 0.1 to 0.3 1/s. The viscosity value may be the value recorded at 25° C. in a steady shear measurement. Such measurements are described in the worked examples of the present case, and exemplary results are set out in FIG. 9.

Figure 16:
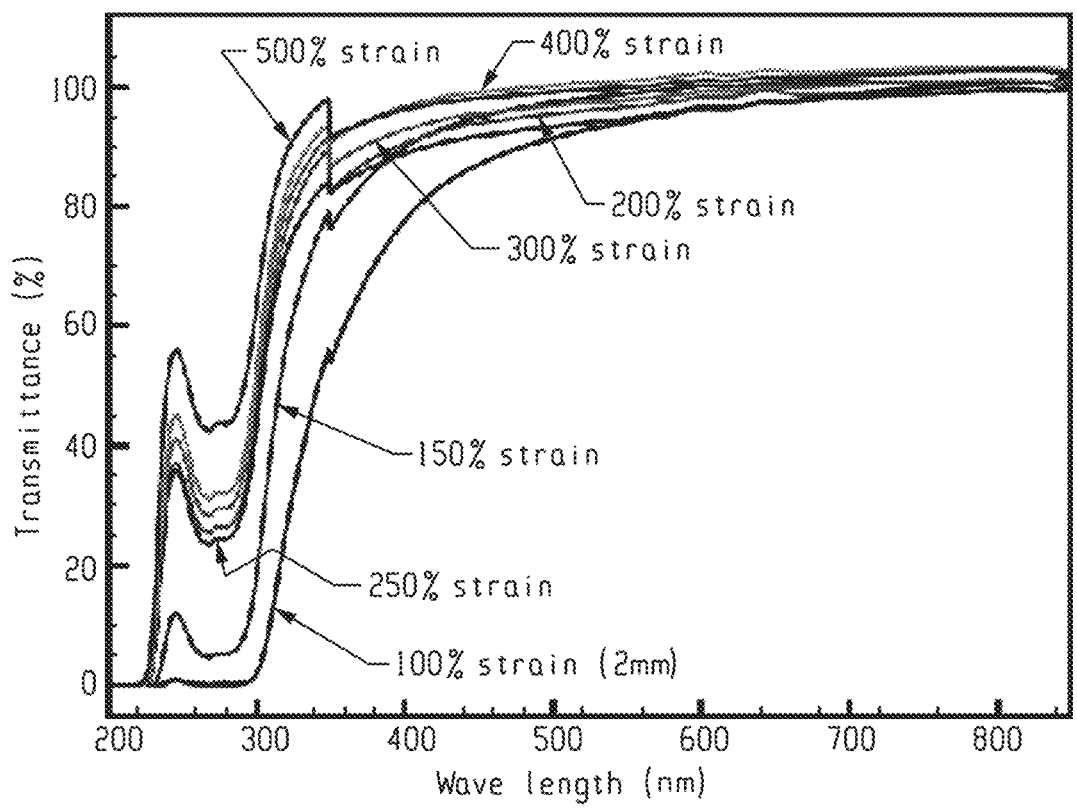
FIG. 16 is the UV/vis transmittance spectra of the dual networks during the stretching, and fully 100% transparency in the visible light range (400 to 700 nm).

It is noted that the hydrogels described in WO 2013/124654 have lower viscosity values at shear rates in the range 0.1 to 0.5 1/s (see, for example FIGS. 16(a) and (b) in WO 2013/124654).

The storage modulus value (G') of a hydrogel may be the value recorded at 25° C. from a strain amplitude sweep measurement and is the value taken at a strain value in the range 0.01 to 100%, for example in the range 0.1 to 10%. The angular frequency may be 10 or 60 rad/s, such as 10 rad/s.

In one embodiment, the hydrogel has a storage modulus, G', (from a strain amplitude sweep measurement) of at least 10 Pa, at least 100 Pa, at least 500 Pa, at least 1,000 Pa, at least 2,000 Pa, at least 5,000 Pa, or at least 10,000 Pa.

In one embodiment, the hydrogel has a storage modulus, G', (from a strain amplitude sweep measurement) of at most 20,000 at most 30,000 Pa, at most 50,000 Pa, at most 100,000 Pa or at most 500,000 Pa.

In one embodiment, the hydrogel has a storage modulus (from a strain amplitude sweep measurement) in a range where the minimum and maximum amounts are selected from the embodiments above. For example, the storage modulus is in the range 100 to 30,000 Pa, for example 1,000 to 30,000 Pa.

It is noted that the storage modulus values, G', (from a strain amplitude sweep measurement) reported in WO 2013/124654 are considerably lower than those recorded for the hydrogels of the present case. See, for example, FIG. 9 (a) of WO 2013/124654 where the reported storage modulus values are no more than 1,000 Pa across the strain range 0.1 to 10%.

The scale of storage modulus will dictate the intended use of the hydrogel. Materials having a high storage modulus, such as above 1,000 Pa in a strain amplitude sweep measurement across the strain range 0.1 to 10%, are well suited for use in biomaterial application, such as cartilage replacement. Here, the toughness and mechanical performance of the hydrogel is well matched to that of the original biomaterial. Materials having a lower storage modulus, such as 1,000 Pa or less in a strain amplitude sweep measurement across the strain range 0.1 to 10%, are not suited for these applications, although they may find use as a general material for the replacement of soft tissues. The hydrogels of the present have useful storage modulus values, such as high storage modulus values, making them suitable for use as biomaterials.

Alternatively, the storage modulus value of the hydrogel may be the value recorded at 25° C. from a frequency sweep measurement and is the value taken at a frequency value in the range 0.1 to 100 rad/s, for example in the range 0.1 to 10 rad/s, such as 0.1, 1.0 or 10 rad/s. The strain may be 0.5% or 1%.

Figure 24A:
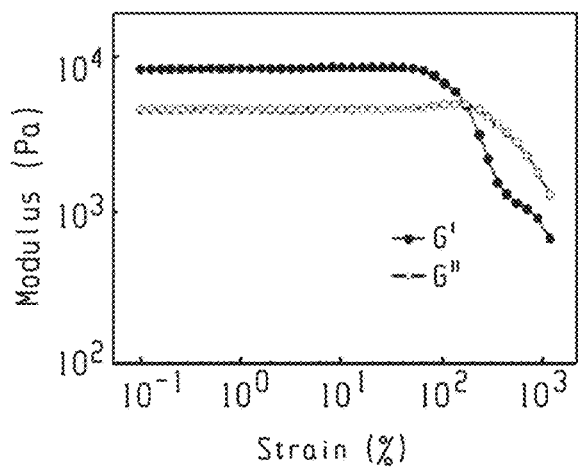
FIG. 24a shows the change in G' and G" (Modulus, Pa) for an AAm-based CB[8]hydrogel via dynamic room-temperature with amplitude sweep (from $10^{-1}$ to $10^3$% strain, 10 rad $s^{-1}$)
Figure 24B:
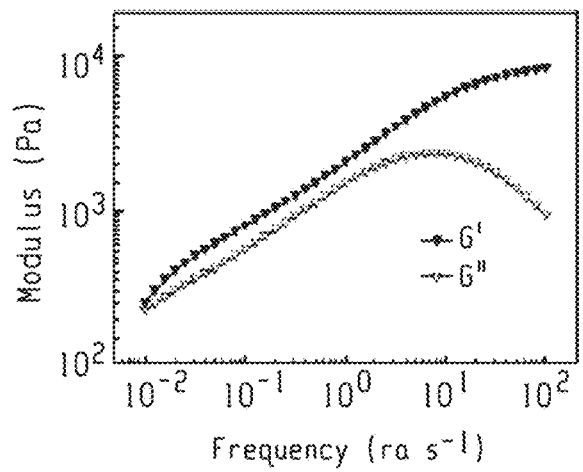
FIG. 24b with a frequency sweep (from $10^{-2}$ to $10^2$ rad $s^{-1}$, 1% strain).
Figure 25A:
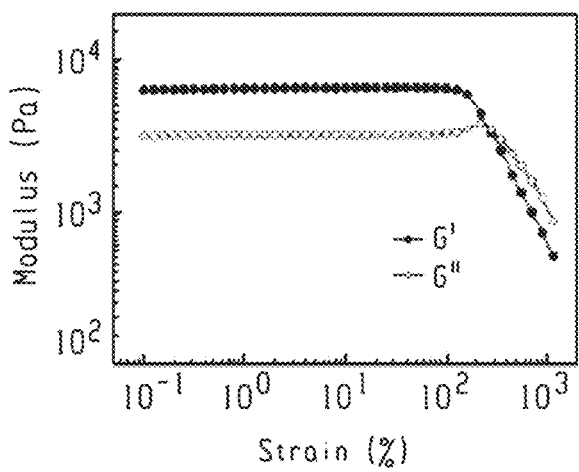
FIG. 25a shows the change in G' and G" (Modulus, Pa) for an N-isopropylacrylamide (NIPAm)-based CB[8] hydrogel via dynamic room-temperature amplitude sweep (from $10^{-1}$ to $10^3$% strain, 10 rad $s^{-1}$)
Figure 25B:
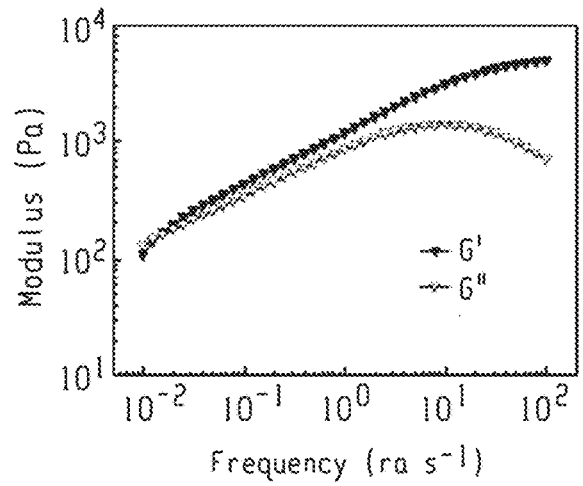
FIG. 25b with a frequency sweep (from $10^{-2}$ to $10^2$ rad $s^{-1}$, 1% strain).
Figure 26A:
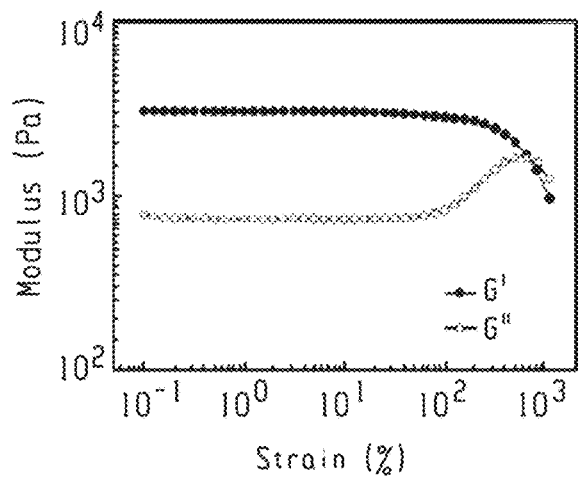
FIG. 26a shows the change in G' and G" (Modulus, Pa) for a 2-(dimethylamino)ethyl methacrylate-based CB[8] hydrogel via dynamic room-temperature amplitude sweep (from $10^{-1}$ to $10^3$% strain, 10 rad $s^{-1}$)
Figure 26B:
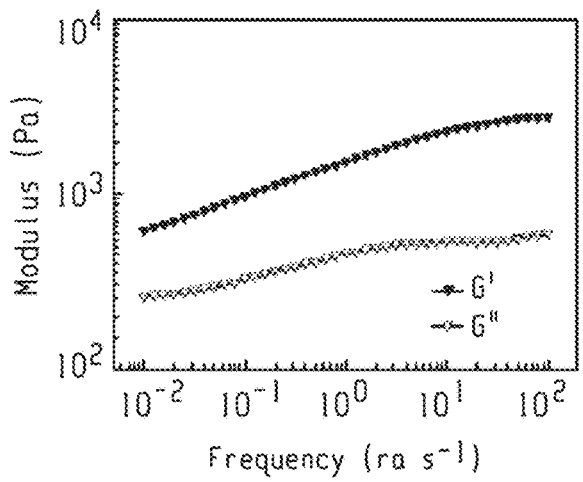
FIG. 26b a frequency sweep (from $10^{-2}$ to $10^2$ rad $s^{-1}$, 1% strain).
Figure 27A:
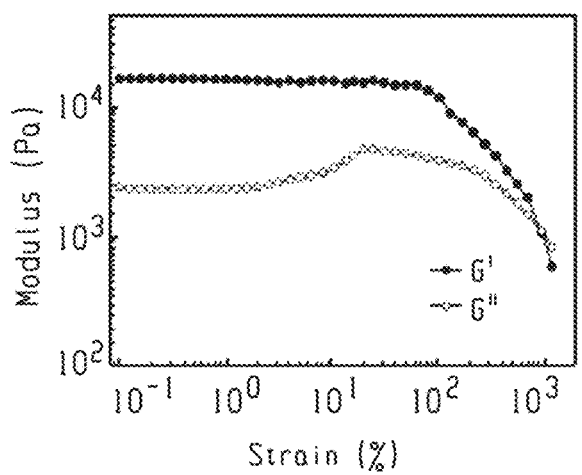
FIG. 27a shows the change in G' and G" (Modulus, Pa) for an acrylic acid (AA)-based CB[8] hydrogel via dynamic room-temperature with an amplitude sweep (from $10^{-1}$ to $10^3$% strain, 10 rad $s^{-1}$)
Figure 27B:
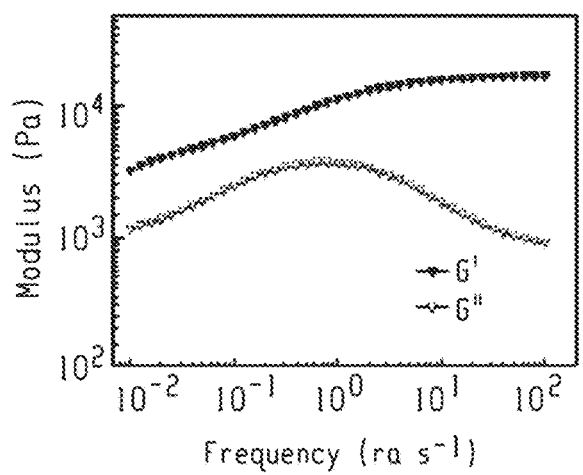
FIG. 27b with a frequency sweep (from $10^{-2}$ to $10^2$ rad $s^{-1}$, 1% strain).
Figure 28A:
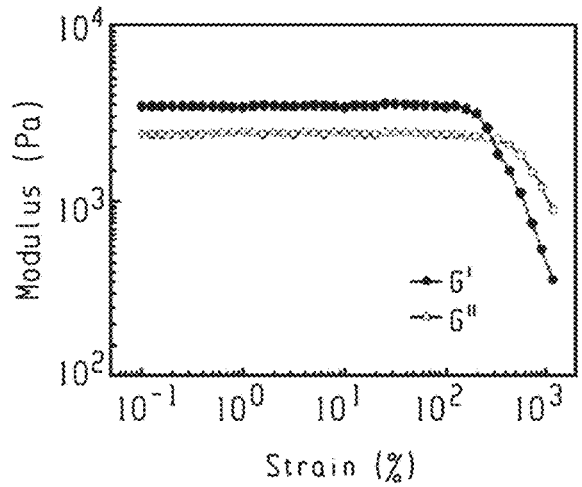
FIG. 28a shows the change in G' and G" (Modulus, Pa) for a 1-vinyl-3-ethylimidazolium bromide (ViEt)-based CB[8] hydrogel via dynamic room-temperature with an amplitude sweep (from $10^{-1}$ to $10^3$% strain, 10 rad $s^{-1}$)
Figure 28B:
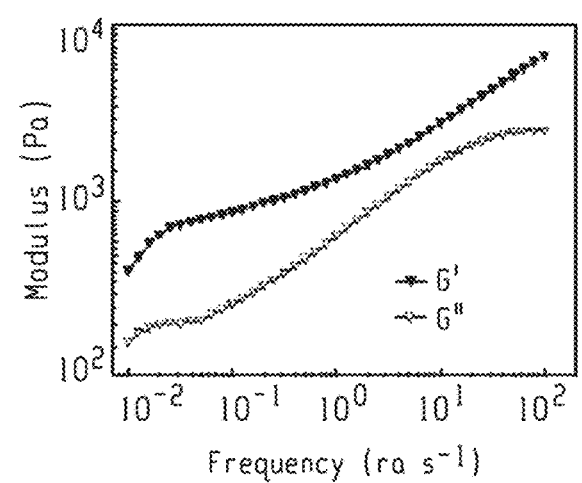
FIG. 28b with a frequency sweep (from $10^{-2}$ to $10^2$ rad $s^{-1}$, 1% strain).
Figure 29A:
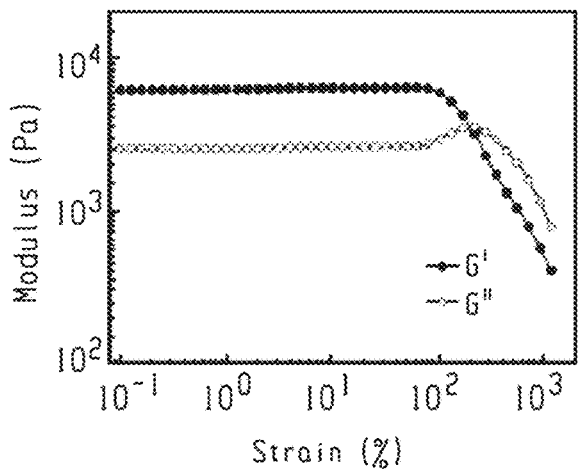
FIG. 29a shows the change in G' and G" (Modulus, Pa) for a 3-[2-(methacryloyloxy)ethyl](dimethyl)ammonio-1-propanesulfonate-based (MPS) CB[8] hydrogel via dynamic room-temperature with an amplitude sweep (from $10^{-1}$ to $10^3$% strain, 10 rad $s^{-1}$)
Figure 29B:
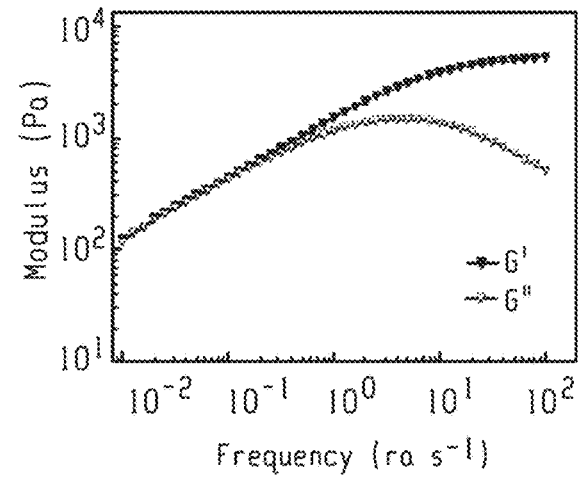
Figure 30A:
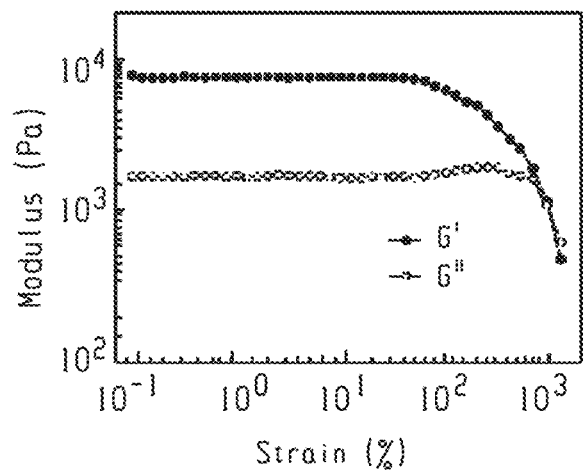
FIG. 30a shows the change in G' and G" (Modulus, Pa) for a poly(ethylene glycol) methacrylate-based (PEGMA) CB[8] hydrogel via dynamic room-temperature with an amplitude sweep (from $10^{-1}$ to $10^3$% strain, 10 rad $s^{-1}$)
Figure 30B:
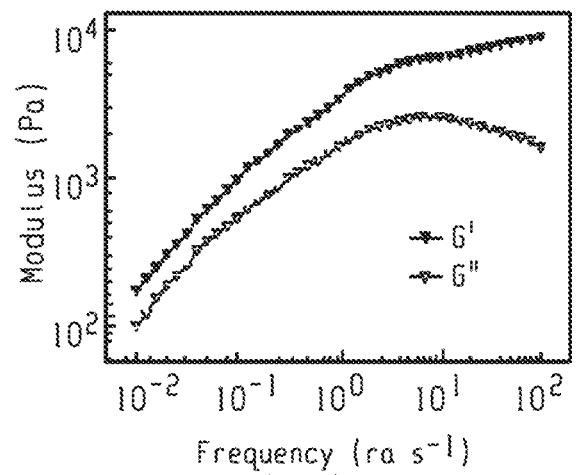
FIG. 30b with an frequency sweep (from $10^{-2}$ to $10^2$ rad $s^{-1}$, 1% strain).
Figure 31A:
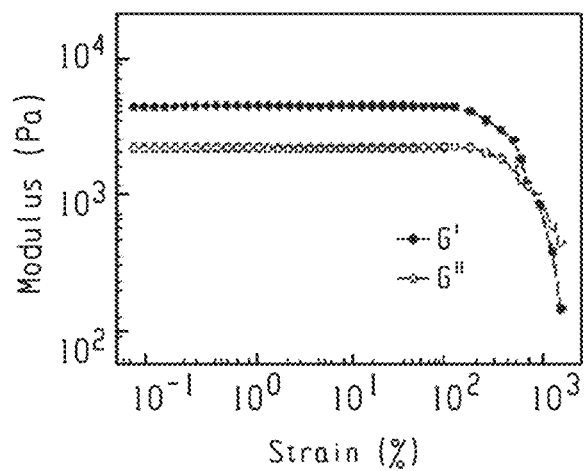
FIG. 31a shows the change in G' and G" (Modulus, Pa) for a dimethylacrylamide-based (DMA) CB[8] hydrogel via dynamic room-temperature with an amplitude sweep (from $10^{-1}$ to $10^1$% strain, 10 rad $s^{-1}$)
Figure 31B:
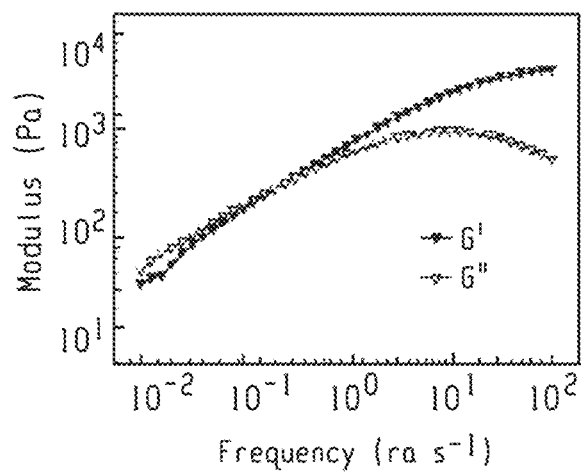
FIG. 31b with a frequency sweep (from $10^{-2}$ to $10^2$ rad $s^{-1}$, 1% strain).

In the worked examples of the present case, the frequency sweep experiments are typically performed at 0.5% or 1% strain. It is expected that the frequency sweep data recorded at these different strains will be similar, and may differ only owing to differences in sample manipulation and measurement conditions (and this has also been seen in identical hydrogels tested at different strains: see, for example, FIGS. 9 and 24, which show the frequency sweep date for the same hydrogel prepared in different batches, and tested at 0.5% or 1% strain).

In one embodiment, the hydrogel has a storage modulus (from a frequency sweep measurement) of at least 10 Pa, at least 100 Pa, at least 500 Pa, or at least 1,000 Pa.

In one embodiment, the hydrogel has a storage modulus (from a frequency sweep measurement) of at most 5,000 Pa, at most 10,000 Pa, at most 50,000 Pa, or at most 100,000 Pa.

In one embodiment, the hydrogel has a storage modulus (from a frequency sweep measurement) in a range where the minimum and maximum amounts are selected from the embodiments above. For example, the storage modulus is in the range 10 to 10,000 Pa, for example 100 to 10,000 Pa, such as 500 to 10,000 Pa.

It is noted that the storage modulus values, G', (from a frequency sweep measurement) reported in WO 2013/124654 are considerably lower than those recorded for the hydrogels of the present case. See, for example, FIG. 9(c) of WO 2013/124654 where the reported storage modulus values are no more than 1,000 Pa across the frequency range 0.1 to 10 rad/s.

The loss modulus value (G") of the hydrogel may be the value recorded at 25° C. from a strain amplitude sweep measurement and is the value taken at a strain value in the range 0.1 to 100%, for example in the range 0.1 to 10%, such as 0.1, 1.0 or 10%. In one embodiment, the hydrogel has a loss modulus (from a strain amplitude sweep measurement) of at least 10 Pa, at least 100 Pa, at least 500 Pa, at least 1,000 Pa or at least 2,000 Pa.

In one embodiment, the hydrogel has a loss modulus (from a strain amplitude sweep measurement) of at most 5,000 Pa, at most 10,000 Pa, at most 50,000 Pa, or at most 100,000 Pa.

In one embodiment, the hydrogel has a loss modulus (from a strain amplitude sweep measurement) in a range where the minimum and maximum amounts are selected from the embodiments above. For example, the loss modulus is in the range 100 to 10,000 Pa, for example 500 to 10,000 Pa, such as 1,000 to 10,000 Pa.

The loss modulus values reported in WO 2013/124654 for a strain amplitude sweep are considerably lower than those recorded for the hydrogels of the present case. See, for example, FIG. 9 (a) of WO 2013/124654 where the reported storage modulus values are no more than 1,000 Pa, and are closer to 100 Pa.

Loss modulus is typically used to describe the viscosity of a network system, and a higher loss modulus is indicative of a system that has a higher capacity to dissipate energy, and therefore the network may be regarded as having a certain toughness that is not shared with those material having a low loss modulus. The hydrogels of the present case have useful loss modulus values. The ability to dissipate energy is connected to the dissociation of the non-covalent complexes, which are alter able to reform as part of a dynamic self-healing process.

Alternatively, the loss modulus value of the hydrogel may be the value recorded at 25° C. from a frequency sweep measurement and is the value taken at a frequency value in the range 0.1 to 100 rad/s, for example in the range 0.1 to 10 rad/s, such as 0.1, 1.0 or 10 rad/s.

In one embodiment, the hydrogel has a loss modulus (from a frequency sweep measurement) of at least 1 Pa, at least 10 Pa, at least 100 Pa, at least 500 Pa, or at least 1,000 Pa.

In one embodiment, the hydrogel has a loss modulus (from a frequency sweep measurement) of at most 5,000 Pa, at most 10,000 Pa, or at most 50,000 Pa.

In one embodiment, the hydrogel has a loss modulus (from a frequency sweep measurement) in a range where the minimum and maximum amounts are selected from the embodiments above. For example, the loss modulus is in the range 1 to 5,000 Pa, for example 100 to 5,000 Pa, such as 1,000 to 5,000 Pa.

The loss modulus values reported in WO 2013/124654 for a frequency sweep are considerably lower than those recorded for the hydrogels of the present case. See, for example, FIG. 9 (c) of WO 2013/124654 where the reported storage modulus values are no more than 1,000 Pa, and are closer to 100 Pa.

In one embodiment, the storage modulus and/or the loss modulus value is substantially the same across the strain range 0.1 to 100%, 0.1 to 10% or 1 to 10%. The present inventors have found that the hydrogels of the invention have an extremely broad linear viscoelastic region, for example up to 100%. The hydrogels begin to show a deviation from linear viscoelasticity, for example at a strain value of 100% or more.

In one embodiment, the loss modulus is not greater than the storage modulus for any frequency value in the range 0.1 to 100 rad/s for a hydrogel analysed by frequency sweep measurement at 25° C. Thus, the storage modulus for the hydrogels is dominant.

In one embodiment, the loss modulus is not greater than the storage modulus for any strain value in the range 0.1 to 100% strain for a hydrogel analysed by strain amplitude sweep measurement at 25° C. Thus, the storage modulus for the hydrogels is dominant.

In one embodiment, the changes in storage and loss values with change in frequency (in a frequency sweep experiment) are substantially the same across the range 0.01 to 1 rad/s. Thus, the storage and loss moduli may be said to be parallel. The parallel nature of the modulus values is apparent in a frequency sweep experiment, where the frequency (as rad/s) and the modulus (as Pa) are both expressed on a logarithmic scale. Such is as shown in FIG. 9(b) of the present case.

In one embodiment, the changes in storage and loss values with change in strain (in a strain amplitude sweep experiment) are substantially the same across the range 0.01 to 100%. Thus, the storage and loss moduli may be said to be parallel. The parallel nature of the modulus values is apparent in a strain amplitude sweep experiment, where the strain (as %) and the modulus (as Pa) are both expressed on a logarithmic scale. Such is as shown in FIG. 9(a) of the present case.

Where a strain amplitude sweep measurement is recorded, the frequency may be set to 1 or 10 rad/s.

Where a frequency sweep measurement is recorded, the strain amplitude may be set at 1, 5 or 10% strain. The skilled person will choose a strain value that is appropriate for the material under investigation. The skilled person will understand that the strain values are selected such that the frequency sweeps are performed in the linear viscoelastic regions for the material.

The tan (δ) value may be the value recorded at 25° C. from a strain amplitude sweep measurement and is the value taken at a strain value in the range 0.1 to 10%. The angular frequency may be 10 or 60 rad/s.

In one embodiment, the hydrogel has a tan (δ) value (from a strain amplitude sweep measurement) of at least 0.1, at least 0.2 or at least 0.4.

In one embodiment, the hydrogel has a tan (δ) value (from a strain amplitude sweep measurement) of at most 0.5, at most 0.1, or at most 2.0.

In one embodiment, the hydrogel has a tan (δ) value (from a strain amplitude sweep measurement) in a range where the minimum and maximum amounts are selected from the embodiments above. For example, the tan (δ) value is in the range 0.1 to 0.5, for example 0.2 to 0.4.

In one embodiment, the tan (δ) value is substantially the same across the strain range 0.1 to 100%, 0.1 to 10% or 1 to 10%.

The inventors have found that the hydrogels of the invention are highly elastic and have recorded tan (δ) values of approx. 0.3, as measured from a frequency sweep measurement.

The hydrogels of the invention may be stretched without significant loss of optical transparency.

In one embodiment, a hydrogel at a strain of 150%, 200%, 300% or 500% has a transmittance of 80% or more, such as 90% or more, for example as measured at a wavelength of 400 nm, 450 nm, 500 nm, 550 nm or 600 nm. The transmittance value is with respect to the transmittance of the hydrogel at 100% strain.

In one embodiment, the hydrogel is a conductive hydrogel, such as an ionically conductive hydrogel. Here, the hydrogel polymer is an ionic polymer having a suitable counter ion. In the worked examples a hydrogel is shown to conduct under different strains. The hydrogel polymer is provided with positively-charged imidazolium guests with bromide counter ions.

The resistivity of a hydrogel may be at least 0.002 Ω·m, at least 0.005 Ω·m, at least 0.01 Ω·m, at least 0.05 Ω·m, at least 0.1 Ω·m, at least 0.5 Ω·m, for example as measured at a strain of 0, 1, 2.5 or 4.

The resistivity of a hydrogel may be at most 1 Ω·m, at most 2 Ω·m, at most 5 Ω·m, or at most 10 Ω·m, for example as measured at a strain of 0, 1, 2.5 or 4.

Strain may be expressed as the ratio between the stretched length of a sample in relation to its unstretched length (such as mm/mm).

The resistance of a hydrogel under strain (R), as measured with respect to the resistance when not under strain ($R_0$), may be at most 40, at most 50, or at most 100, for example as measured at a strain of 1, 2.5 or 4. The resistance is expressed as $R/R_0$.

The resistance of a hydrogel may be at least 1, at least 2, at least 5, or at least 10, for example as measured at a strain of 1, 2.5 or 4.

Resistivity and resistance may be determined at room temperature.

The hydrogels of the present invention have excellent reforming characteristics when deformed. Thus, the original viscosity properties of the original hydrogel may be re-obtained upon reassembly of the hydrogel following the perturbation.

The ability of the hydrogel to respond and reform in response to a stress may be determined from a continuous step strain experiment. A hydrogel sample may be subjected to strain over a number of cycles, for example at a constant temperature, such as 20° C. The hydrogels of the present case are capable of retaining their storage and loss modulus values over repeated strain cycles, followed by self-repair, without noticeable loss of modulus.

Figure 18A:
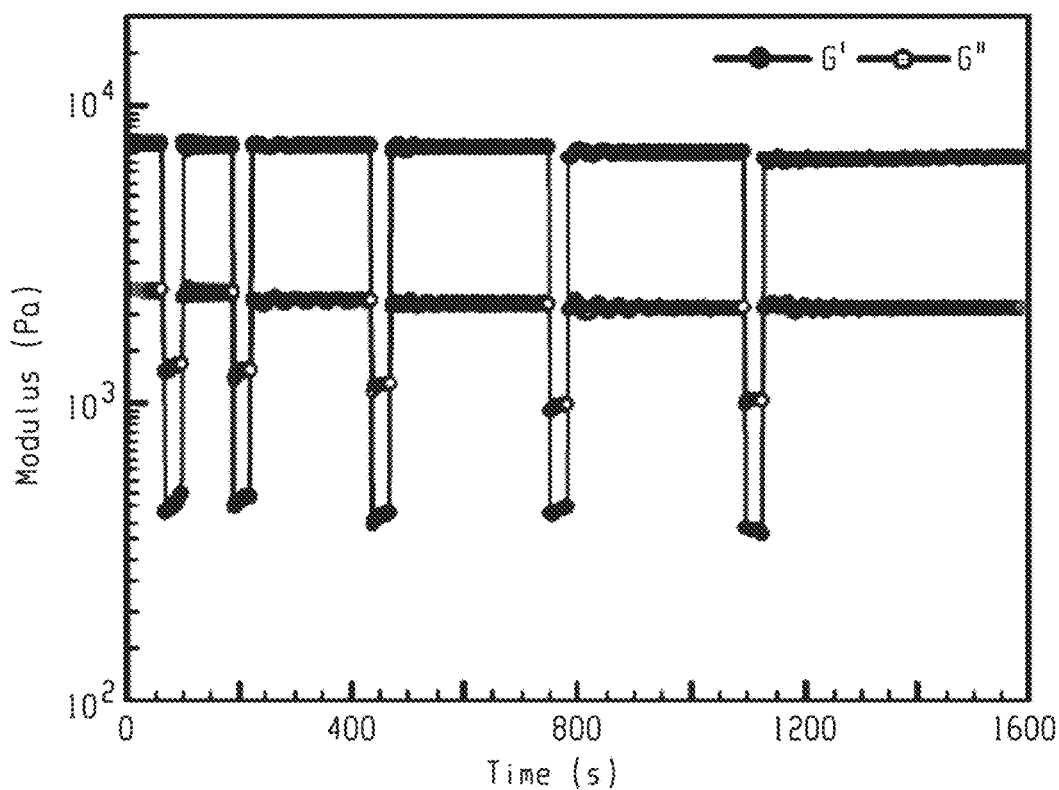
FIG. 18a shows the change in G' and G" (Pa) over time (s) in continuous step strain measurements of the dual networks at 20° C. and 70° C.
Figure 18B:
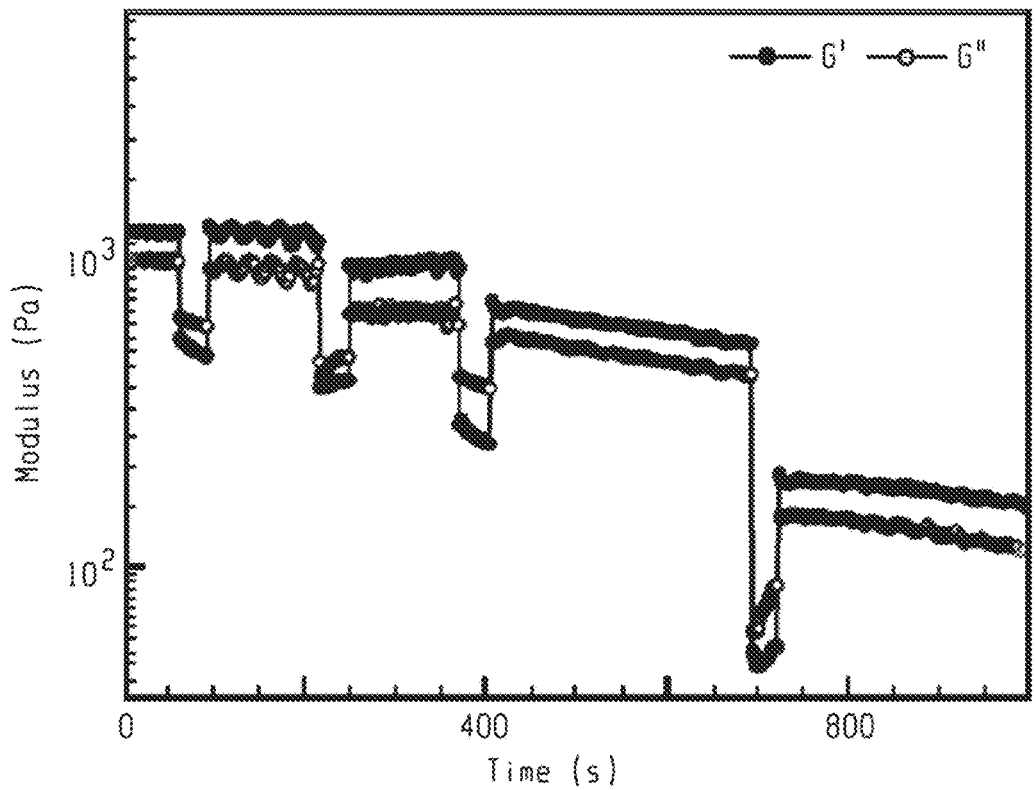
FIG. 18b between a strain of 0.5% and 500% at 10 rad s$^{-1}$. A prompt decrease of the modulus can be observed once a large-strain sweeping for both 20 and 70° C., and a quick self-repairing performance was detected, in agreement with the dynamic essence of the CB[8]-mediated supramolecular interaction. The modulus stay stable for the sample at 20° C. despite the large or small strain sweeping, indicating a good stability. However, for at 70° C., the modulus keeps decreasing, due to the dynamic essence and higher dissociation kinetics for the host-guest interactions.

Thus, the storage and/or loss modulus value for a hydrogel after a strain and self-repair cycle may be at least 90%, at least 95% or at least 98% the value of the hydrogel before the strain. The strain experiment maybe conducted between the strain of 0.5% and 500% at 10 rad s$^{-1}$. The storage and/or loss modulus value may be measured after one, two, three or four strain and repair cycles. The recovery of a dual network hydrogel after a strain and self-repair cycle is shown in FIG. 18(a) of the present case.

As expected, the ability to self-repair at 70° C. is poorer, and the loss and storage modulus decrease over repeated cycles, due to the dynamic nature and higher dissociation kinetics for the host-guest interaction.

In one embodiment, a rheological property of the hydrogel remains substantially the same following at least one cycle of deformation and reassembly, such as two cycles of deformation and reassembly. The rheological property may be one or more properties selected from the group consisting of viscosity, storage modules, loss modulus, and tan (8).

The response of the hydrogel to the deformation cycle demonstrates the strength of a cucurbituril-based network to reversibly form strong hydrogel structures.

Cucurbituril

The hydrogel of the invention makes use of a non-covalent complex of a cucurbituril with one or two guests. Within the art, the term cucurbituril and cucurbit[n]uril may be used interchangeably.

In the preferred embodiments, the cucurbituril is present as a host in a ternary complex with two guests, where the guests are provided on a polymer, which may be the same polymer molecule (thereby providing intramolecular bonding) or on different polymer molecules (thereby providing inter-molecular bonding). Typically the guests in the ternary complex are the same, although it is not essential.

Such hydrogels may be formed from the polymerization of a polymerizable composition comprising cucurbituril and a (first) polymerizable monomer having guest functionality for the cucurbituril, and optionally further comprising a second polymerizable monomer having guest functionality for the cucurbituril.

The present invention is nevertheless not limited to those hydrogel having ternary complexes, and a hydrogel may contain non-covalent cross-links that are based on the formation of binary complexes. Here, cucurbituril is present as a host in a binary complex with one guest, where the guest is provided on a polymer and the cucurbituril is covalently linked to a polymer, and these may be the same polymer molecule (thereby providing intramolecular bonding) or on different polymer molecules (thereby providing inter-molecular bonding).

Such hydrogels may be formed from the polymerization of a polymerizable composition comprising cucurbituril and a (first) polymerizable monomer having guest functionality for the cucurbituril, where the cucurbituril is covalently bonded to a second polymerizable monomer.

It follows that cucurbiturils that are capable of forming ternary complexes and binary complexes find use in the present invention. There are many examples in the art of cucurbiturils for use in forming such complexes.

One of the present inventors has previously shown the use of cucurbituril as a supramolecular handcuff to link and/or crosslink polymers using guest molecules present on one or more polymers. The formation of such complexes links individual polymer molecules thereby to form a network of material. Together with water, this network forms the hydrogel.

Recent work has shown that cucurbituril compounds have high in vitro and in vivo biocompatibility and have extremely low toxicity (see Uzunova et al. *Org. Biomol. Chem.* 2010, 8, 2037-2042). Thus, when used together with non-toxic polymer components, the present hydrogels are also suitable for use in biological systems.

The cucurbituril may be capable of forming a ternary complex. For example, CB[8], is capable of forming a ternary complex. As too are CB[10] and CB[12] compounds. The cucurbituril may be capable of forming a binary complex. For example, CB[7], is capable of forming a ternary complex. As too is CB[8] with an appropriate guest molecule.

The cucurbituril may be a CB[8], CB[10] or CB[12] compound.

In one embodiment, the cucurbituril is a CB[8] compound.

References to a cucurbituril compound are references to variants and derivatives thereof.

A variant of CB[8] may include a structure having one or more repeat units that are structurally analogous to glycoluril. The repeat unit may include an ethylurea unit.

Where all the units are ethylurea units, the variant is a hemicucurbituril. The variant may be a hemicucurbit[12]uril (shown below, see also Lagona et al. *Angew. Chem. Int. Ed.* 2005, 44, 4844).

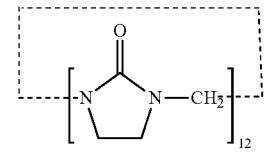

Cucurbituril derivatives are provided and find use in the methods described herein. A derivative of a cucurbituril is a structure having one, two, three, four or more substituted glycoluril units. A substituted cucurbituril compound may be represented by the structure below:

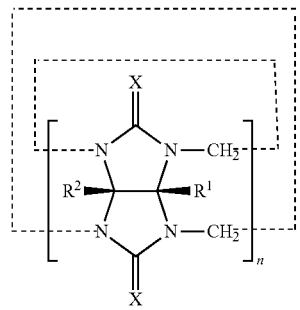

wherein:
n is an integer of at least 5;
and for each glycoluril unit
each X is O, S or NR$^3$, and —$R^1$ and —$R^2$ are each independently selected from —H and the following optionally substituted groups: —$R^3$, —OH, —$OR^3$, —COOH, —$COOR^3$, —$NH_2$, —$NHR^3$ and —$N(R^3)_2$ where —$R^3$ is independently selected from $C_{1-20}$alkyl, $C_{6-20}$carboaryl, and $C_{5-20}$heteroaryl, or where —$R^1$ and/or —$R^2$ is —$N(R^3)_2$, both —$R^3$ together form a $C_{5-7}$ heterocyclic ring; or together —$R^1$ and —$R^2$ are $C_{4-6}$alkylene forming a $C_{6-8}$carbocyclic ring together with the uracil frame.

In one embodiment, one of the glycoluril units is a substituted glycoluril unit. Thus, —$R^1$ and —$R^2$ are each independently —H for n−1 of the glycoluril units.

In one embodiment, n is 5, 6, 7, 8, 9, 10, 11 or 12.
In one embodiment, n is 5, 6, 7, 8, 10 or 12.
In one embodiment, n is 8, 10 or 12.
In one embodiment, n is 8.
In one embodiment, n is 7.
In one embodiment, each X is O.
In one embodiment, each X is S.
In one embodiment, $R^1$ and $R^2$ are each independently H.
In one embodiment, for each unit one of $R^1$ and $R^2$ is H and the other is independently selected from —H and the following optionally substituted groups: —$R^3$, —OH, —$OR^3$, —COOH, —$COOR^3$, —$NH_2$, —$NHR^3$ and —$N(R^3)_2$. In one embodiment, for one glycoluril unit, one of $R^1$ and $R^2$ is H and the other is independently selected from —H and the following optionally substituted groups: —$R^3$, —OH, —$OR^3$, —COOH, —$COOR^3$, —$NH_2$, —$NHR^3$ and —$N(R^3)_2$. In this embodiment, the remaining glycoluril units are such that $R^1$ and $R^2$ are each independently H.

Preferably —$R^3$ is $C_{1-20}$alkyl, most preferably $C_{1-6}$ alkyl. The $C_{1-20}$alkyl group may be linear and/or saturated. Each group —$R^3$ may be independently unsubstituted or substituted. Preferred substituents are selected from: —$R^4$, —OH, —$OR^4$, —SH, —$SR^4$, —COOH, —$COOR^4$, —$NH_2$, —$NHR^4$ and —$N(R^4)_2$, wherein —$R^4$ is selected from $C_{1-20}$ alkyl, $C_{6-20}$ carboaryl, and $C_{5-20}$ heteroaryl. The substituents may be independently selected from —COOH and —$COOR^4$.

In some embodiments, —$R^4$ is not the same as —$R^3$. In some embodiments, —$R^4$ is preferably unsubstituted.

Where —$R^1$ and/or —$R^2$ is —$OR^3$, —$NHR^3$ or —$N(R^3)_2$, then —$R^3$ is preferably $C_{1-6}$alkyl. In some embodiments, —$R^3$ is substituted with a substituent —$OR^4$, —$NHR^4$ or —$N(R^4)_2$.

Each —$R^4$ is $C_{1-6}$ alkyl and is itself preferably substituted.

Suitable for use in the present invention are cucurbiturils that are covalently connected to a polymerizable monomer. This is referred to as the fifth monomer in the description above. Typically, the cucurbituril is linked to the polymerizable monomer via one or more of the glycoluril units at position $R^1$ and/or $R^2$. For example, Jung et al. (*Biomacromoelcules* 2014, 15, 708) describe the use of cucurbituril that is functionalised at $R^1$ and $R^2$ with an allyl ether group.

In the preferred embodiments cucurbituril is not covalently connected to a polymerizable monomer.

It is noted that such monomers are not used to form non-covalent complexes until the polymer incorporating the monomer has been formed. After polymer formation, the polymer-bound cucurbituril is brought into contact with guests suitable for forming non-covalent complexes.
Cucurbituril Guest As noted above, the guest is a compound that is capable of forming a host-guest complex with a cucurbituril. The term complexation therefore refers to the establishment of the host-guest complex. The guest is provided within a monomer, such as the first and third monomers.

In some embodiments of the invention, the host-guest complex is a ternary complex comprising the cucurbituril host and a first guest and a second guest. Typically such complexes are based around CB[8] and variants and derivatives thereof. It is preferred that the first guest and the second guest are the same.

In principal, any compound having a suitable binding affinity (such as those mentioned in the discussion of the complex above) may be used in the methods of the present invention. The compound used may be selected based on the size of the moieties that are thought to interact with the cavity of the cucurbituril. The size of these moieties may be sufficiently large to permit complexation only with larger cucurbituril forms.

Within a polymerizable monomer, a cucurbituril guest is connected, such as covalently directly connected or covalently indirectly connected, to the polymerizable group, such as a vinyl group, which participates in the polymerization reaction.

In one embodiment, the guest is not linked to the polymerizable group via an ester linkage. The hydrogels of the present invention may be used in applications where the relatively labile ester functionality would not be helpful.

Cucurbituril guest molecules are well known in the art. Examples of guest compounds for use include those described in WO 2009/071899, Jiao et al. (Jiao et al. *Org. Lett.* 2011, 13, 3044), Jiao et al. (Jiao et al. *J. Am. Chem. Soc.* 2010, 132, 15734), Rauwald et al. (Rauwald et al. *J. Phys. Chem.* 2010, 114, 8606) and WO 2011/077099.

The present inventors have previously investigated complexation of guest molecules when these molecules are attached to another group (such as a polymer or a small organic compound) and when these molecules are unattached. The use of isothermal calorimeter has demonstrated that the attachment of a guest to another group does not result in a reduction in the binding constant of the guest. Thus, there is no observable effect on binding from polymer steric hindrance.

In one embodiment of the invention, the cucurbituril is CB[8] and the guests are molecules suitable for forming a ternary complex with this host.

In a preferred hydrogel, the complex of the cucurbituril is a ternary complex formed with two guests, where each guest is the same. This hydrogel may be formed from a polymerizable composition having only one monomer with guest functionality. A hydrogel may also be formed from a polymerizable composition having more than one polymerizable monomer, where each monomer has the same guest, with the remaining portion of the monomer differing between monomers.

The hydrogel may also contain ternary complexes where the first and second guests are different. Such hydrogels are formed from a polymerizable composition having a first monomer having a guest functionality, and a further monomer, such as a third monomer, having a different guest functionality. In this complex, one guest may be electron rich guest and one guest molecule may be electron deficient.

The guest may be ionic, such as cationic or anionic, and there may be a suitable counter ion. The ionic group present in the guest, may also be present, together with a counter ion, in the hydrogel product. Advantageously, the presence of ionic functionality within a monomer, such as a guest, provides a hydrogel having ionic conductivity. Examples of the type of guests that can be used to provide ionic conductivity are the cationic organic nitrogen heterocycles described below.

In one embodiment, a guest is an ionic liquid. Typically, such guests are suitable for forming a complex with CB[7]. However, they may also form complexes with CB[8] in either a binary complex, or in a ternary complex together with another small guest molecule or solvent (see Jiao et al. *Org. Lett.* 2011, 13, 3044). An ionic liquid is typically a cationic organic nitrogen heterocycle.

Thus, a guest may comprise a cationic organic nitrogen heterocycle, which may be an aromatic nitrogen heterocycle (a heteroaryl) or a non-aromatic nitrogen heterocycle. Here, the guest typically comprises a counter-anion to the cationic organic nitrogen heterocycle. The nitrogen heteroaryl group is preferably a nitrogen $C_{5-6}$heteroaryl group, most preferably a nitrogen $C_{5-6}$heteroaryl group, where the subscript refers to the total number of atoms in the ring or rings, including carbon and nitrogen atoms. The non-aromatic nitrogen heterocycle is preferably a nitrogen $C_{5-6}$heterocycle, where the subscript refers to the total number of atoms in the ring or rings, including carbon and nitrogen atoms. A nitrogen atom in the ring of the nitrogen heterocycle is quaternised.

The counter-anion may be a halide, preferably a bromide. Other counter-anions suitable for use are those that result in a complex that is soluble in water.

A guest is preferably selected from the group consisting of: imidazolium moiety; pyridinium moiety; quinolinium moiety; pyrimidinium moiety; pyrrolium moiety; quaternary pyrrolidine moiety; and quaternary amine.

Preferably, the guest is or comprises an imidazolium moiety. An especially preferred guest is 1-alkyl-3-alkylimidazolium, where the alkyl groups are optionally substituted.

1-Alkyl-3-alkylimidazolium compounds, where the alkyl groups are unsubstituted, are especially suitable for forming a complex with CB[7].

1-Alkyl-3-alkylimidazolium compounds, where the alkyl groups are unsubstituted, are especially suitable for forming a complex with CB[6]

1-Alkyl-3-alkylimidazolium compounds, where an alkyl group is substituted with aryl (preferably napthyl), are especially suitable for forming a complex with CB[8].

The 1-alkyl and 3-alkyl substituents may the same or different. Preferably, they are different.

In one embodiment, the 3-alkyl substituent is methyl, and is preferably unsubstituted.

In one embodiment, the 1-alkyl substituent is ethyl or butyl, and each is preferably unsubstituted.

In one embodiment, the optional substituent is aryl, preferably $C_{5-10}$aryl. Aryl includes carboaryl and heteroaryl. Aryl groups include phenyl, napthyl and quinolinyl.

In one embodiment, the alkyl groups described herein are linear alkyl groups.

Each alkyl group is independently a $C_{1-6}$alkyl group, preferably a $C_{1-4}$alkyl group.

The aryl substituent may itself be another 1-alkyl-3-substituted-imidazolium moiety (where the alkyl group is attached to the 3-position of the ring).

In another embodiment, the compound preferably comprises a pyridinium moiety.

The ionic liquid molecules described above are particularly useful for forming binary host-guest complexes. Complexes comprising two ionic liquid molecules as guests within a cucurbituril host are also encompassed by the present invention.

A cucurbituril may be capable of forming both binary and ternary complexes. For example, it has been previously noted that CB[6] compounds form ternary complexes with short chain 1-alkyl-3-methylimidazolium guest molecules, whilst longer chain 1-alkyl-3-methylimidazolium guest molecules form binary complexes with the cucurbituril host.

Preferred guests for use in the present invention are of the form $H^+X^-$, where $H^+$ is one of the following cations,

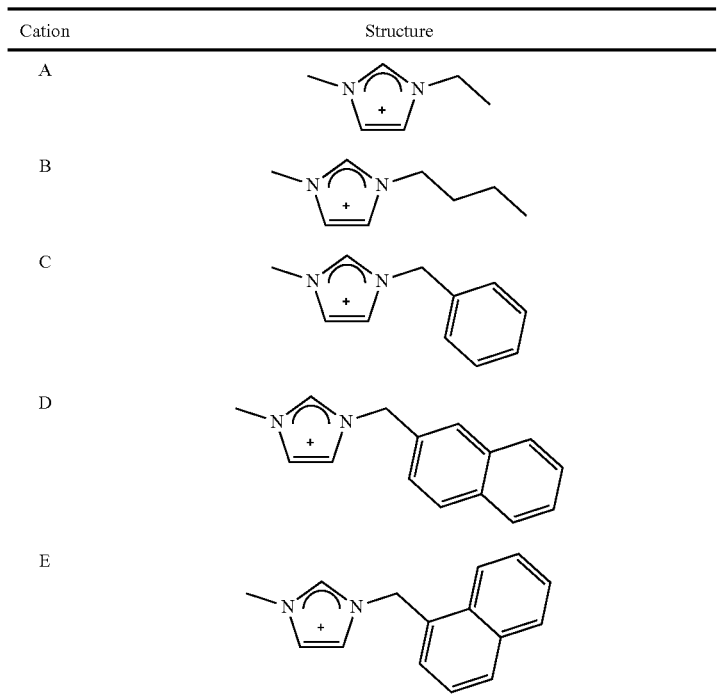

| Cation | Structure |
|---|---|
| A | 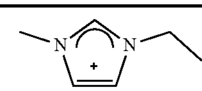 |
| B | 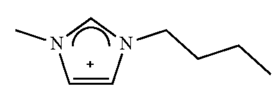 |
| C | 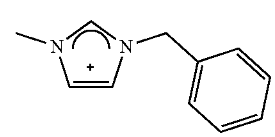 |
| D | 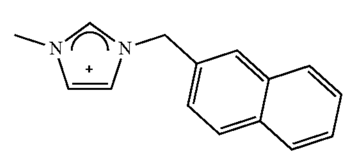 [SMILES: CN1C=CN(Cc2ccc3ccccc3c2)C1] |
| E | 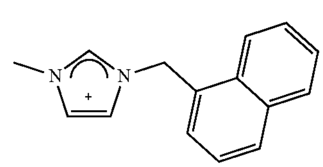 [SMILES: CN1C=CN(Cc2cccc3ccccc23)C1] |

| Cation | Structure |
|---|---|
| F | 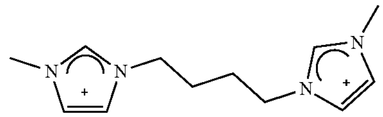 |
| G | 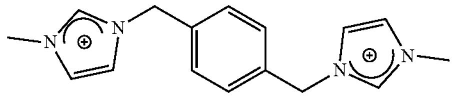 |
| H | 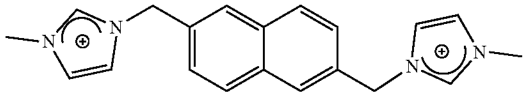 |
| I | 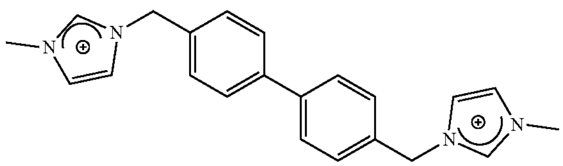 |
| J | 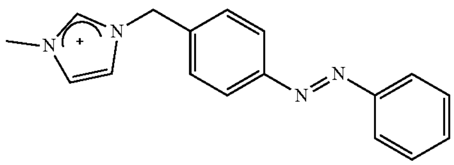 [SMILES: CN1C=CN(Cc2ccc(/N=N/c3ccccc3)cc2)C1] |
| K | | and X⁻ is a suitable counter-anion, as defined above. A preferred counter anion is a halide anion, preferably Br⁻.

In a preferred embodiment, cation A or cation B may be used to form a complex with CB[7] or CB[6].

In a preferred embodiment, cation C, D or E may be used to form a complex with CB[8], for example cation C is used as a guest in the present work.

Cations A and B may be referred to as 1-ethyl-3-methylimidazolium and 1-butyl-3-methylimidazolium respectively.

Cations D and E may be referred to as 1-naphthalenylmethyl-3-methylimidazolium, where D is 1-naphthalen-2-yl-methyl-3-methylimidazolium and E is 1-naphthalen-1-ylm-ethyl-3-methylimidazolium.

Alternatively or additionally, a guest may be or contain an imidazolium salt of formula (I):

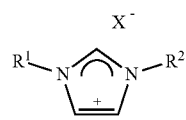

wherein X⁻ is a counter anion;
R¹ is independently selected from H and saturated $C_{1-6}$ alkyl;
R² is independently $C_{1-10}$ alkyl which may optionally contain one or more double or triple bonds, and may be optionally interrupted by a heteroatom selected from —O—, —S—, —NH—, and —B—, and may be optionally substituted.

In one embodiment, X⁻ is independently selected from the group consisting of Cl⁻, Br⁻, I⁻, $BF_4^-$, $PF_6^-$, OH⁻, SH⁻, $HSO_4^-$, $HCO_3^-$, $NTf_2^-$, $C_2N_5O_4^-$, $AlCl_4^-$, $Fe_3Cl_{12}^-$, $NO_3^-$, $NMeS_2^-$, $MeSO_3^-$, $SbF_6^-$, $PrCB_{11}H_{11}^-$, $AuCl_4^-$, $HF_2^-$, $NO_2^-$, $Ag(CN)_2^-$, and $NiCl_4^-$. In one embodiment, X⁻ is selected from Cl⁻, Br⁻, and I⁻.

In one embodiment, R¹ is selected from H and linear saturated $C_{1-6}$ alkyl.

In one embodiment, R² is linear $C_{1-10}$ alkyl, which may optionally contain one or more double bonds, and may be optionally interrupted by a heteroatom selected from —O—, —S—, —NH—, and —B—, and may be optionally substituted.

In one embodiment, R² is linear $C_{1-10}$ alkyl, which may optionally contain one or more double bonds, and may be optionally substituted.

In one embodiment, where a double or triple bond is present, it may be conjugated to the imidazolium moiety. Alternatively, the double or triple bond may not be conjugated to the imidazolium moiety.

In one embodiment, the optional substituents are independently selected from the group consisting of halo, optionally substituted $C_{5-20}$ aryl, —$OR^3$, —$OCOR^3$, =O, —$SR^3$, =S, —$BR^3$, —$NR^3R^4$, —$NR^3COR^3$, —$N(R^3)CONR^3R^4$, —$COOR^3$, —$C(O)R^3$, —$C(=O)SR^3$, —$CONR^3R^4$, —$C(S)R^3$, —$C(=S)SR^3$, and —$C(=S)NR^3R^4$, where each of $R^3$ and $R^4$ is independently selected from H and optionally substituted saturated $C_{1-6}$ alkyl, $C_{5-20}$ aryl and $C_{1-6}$ alkylene-$C_{5-20}$ aryl.

or $R^3$ and $R^4$ may together may form an optionally saturated 5-, 6- or 7-membered heterocyclic ring which is optionally substituted with a group —$R^3$.

In one embodiment, the optional substituents are independently selected from the group consisting of halo, optionally substituted $C_{5-20}$ aryl, —$OR^3$, —$OCOR^3$, —$NR^3R^4$, —$NR^3COR^3$, —$N(R^3)CONR^3R^4$, —$COOR^3$, —$C(O)R^3$, and —$CONR^3R^4$, where $R^3$ and $R^4$ are defined as above.

Each $C_{5-20}$ aryl group may be independently selected from a $C_{6-20}$ carboaryl group or a $C_5$-20 heteroaryl group.

Examples of $C_{6-20}$ carboaryl groups include phenyl and napthyl.

Examples of $C_{6-20}$ heteroaryl groups include pyrrole (azole) ($C_5$), pyridine (azine) ($C_6$), furan (oxole) ($C_5$), thiophene (thiole) ($C_5$), oxazole ($C_5$), thiazole ($C_5$), imidazole (1,3-diazole) ($C_5$), pyrazole (1,2-diazole) ($C_5$), pyridazine (1,2-diazine) ($C_6$), and pyrimidine (1,3-diazine) ($C_6$) (e.g., cytosine, thymine, uracil).

Each $C_{5-20}$ aryl is preferably selected from optionally substituted phenyl, napthyl and imidazolium.

Each $C_{6-20}$ aryl group is optionally substituted. The optional substituents are independently selected from halo, $C_{1-6}$ alkyl, —$OR^3$, —$OCOR^3$, —$NR^3R^4$, —$NR^3COR^3$, —$N(R^3)CONR^3R^4$, —$COOR^3$, —$C(O)R^3$, and —$CONR^3R^4$, where $R^3$ and $R^4$ are defined as above.

In one embodiment, each $C_{6-20}$ aryl group is optionally substituted with $C_{1-6}$ alkyl.

Where the $C_{6-20}$ aryl group is an imidazolium, such is preferably substituted at nitrogen with a group $R^1$ (thereby forming a quaternary nitrogen).

The structure of formula (I) comprises an imidazolium moiety having a substituent $R^2$ at the 1-position and a substituent $R^1$ at the 3-position. The structure of formula (I) may be optionally further substituted at the 2-, 4- or 5-positon with a group $R^A$, wherein $R^A$ has the same meaning as $R^1$.

The embodiments above are combinable in any combination, as appropriate.

A cucurbituril guest may be, or contain, a structure from the table below:

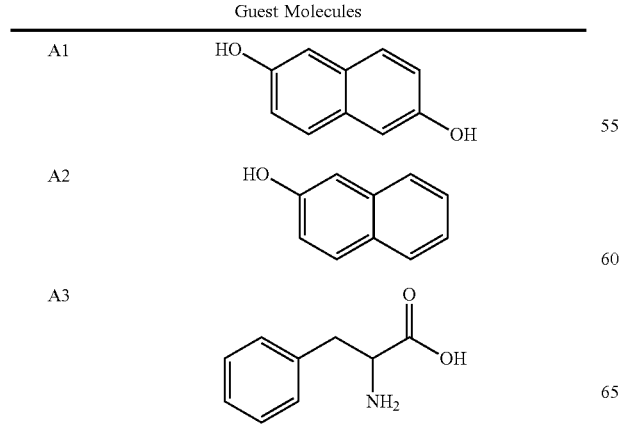

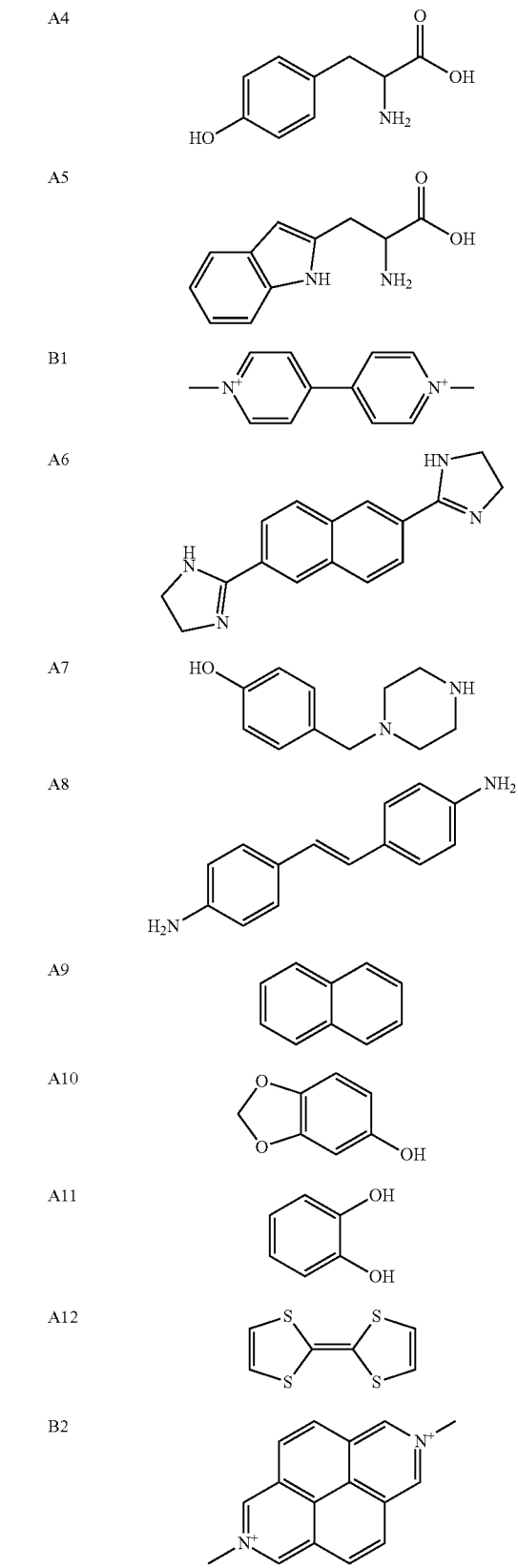

-continued

| Guest Molecules | |
|---|---|
| B3 | [3-methyl-benzo[g]isoquinoline-2,7-diium structure] |
| B4 | [1,1'-dimethyl-4,4'-stilbazolium structure] |
| A13 | [indole] |
| A14 | [serotonin] |
| A15 | [anthracene] |
| A16 | [hexafluorobenzene] |
| A17 | [7-methoxy-2-naphthol] |
| A18 | [1-naphthol] |
| A19 | [2,3-dihydroxynaphthalene] |
| A20 | [2,7-dihydroxynaphthalene] |

-continued

| Guest Molecules | |
|---|---|
| A21 | [3-methoxy-2-naphthol] |
| A22 | [1,5-dihydroxynaphthalene] |
| A23 | [2,6-dihydroxynaphthalene (with 1,5 OH)] |
| A24 | [1,3,8-trihydroxynaphthalene arrangement] |
| A25 | [2-chlorophenol] |
| A26 | [3-chlorophenol] |
| A27 | [phenol] |
| A28 | [benzamide] |
| A29 | [4-chlorophenol] |
| A30 | [2-methoxyphenol] |

-continued

| | Guest Molecules |
|---|---|
| A31 | 4-bromophenol |
| A32 | 4-fluorophenol |
| A33 | 4-iodophenol |
| A34 | 3-methoxyphenol |
| A35 | 3-cyanophenol |
| A36 | resorcinol (1,3-dihydroxybenzene) |
| A37 | 2-hydroxybenzonitrile |
| A38 | 4-methoxyphenol |
| A39 | 1,4-dimethoxybenzene |
| A40 | hydroquinone (1,4-dihydroxybenzene) |
| A41 | phloroglucinol (1,3,5-trihydroxybenzene) |
| A42 | 4-hydroxybenzonitrile |
| A43 | 1H-benzotriazole |
| A44 | azobenzene |
| A45 | 2-naphthalenethiol |
| A46 | 1-adamantylamine |
| A47 | tryptophan |

| Guest Molecules |
|---|
| A48 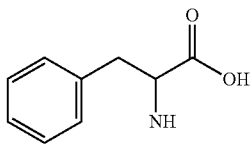 | where the structure may be a salt, including protonated forms, where appropriate. In one embodiment, the guest molecules are guest molecules for CB[8].

In one embodiment, the guest molecule is, or is derived from, or contains, structure A1-A43, A46 or B1-B4, in the table above.

In one embodiment, the guest molecule is, or is derived from, or contains, structure A1, A2, or A13 in the table above.

In one embodiment, the guest molecule is, or is derived from, or contains, structure B1.

Additionally, the guest molecule is or is derived from, or contains, adamantane, ferrocene or cyclooctane (including bicyclo[2.2.2]octane). Such are described by Moghaddam et al. (see *J. Am. Chem. Soc.* 2011, 133, 3570).

Other guest molecules suitable for use include pyrene, dibenzofuran and fluorine, and derivatives thereof. The derivative may be a compound where an aromatic ring atom is replaced with a heteroatom, such as nitrogen. Additionally or alternatively, the derivative may be a compound that is substituted at a ring atom with a group such as halogen, alkyl, hydroxy, amino, alkoxy or the like.

In some embodiments, first and second guest molecules form a pair which may interact within the cavity of cucurbituril to form a stable ternary host-guest complex.

Any guest pair that fits within the cavity of the cucurbituril may be employed. In some embodiments, the pair of guest molecules may form a charge transfer pair comprising an electron-rich and an electron-deficient compound. One of the first and second guest molecules acts as an electron acceptor and the other as an electron donor in the CT pair. For example, the first guest molecule may be an electron deficient molecule which acts an electron acceptor and the second guest molecule may be an electron rich molecule which acts as an electron donor or vice versa. In one embodiment, the cucurbituril is CB[8].

Suitable electron acceptors include 4,4'-bipyridinium derivatives, for example N,N'-dimethyldipyridyliumylethylene, and other related acceptors, such as those based on diazapyrenes and diazaphenanthrenes. Viologen compounds including alkyl viologens are particularly suitable for use in the present invention. Examples of alkyl viologen compounds include N,N'-dimethyl-4,4'-bipyridinium salts (also known as Paraquat).

Suitable electron donors include electron-rich aromatic molecules, for example 1,2-dihydroxybenzene, 1,3-dihydroxybenzene, 1,4-dihydroxybenzene, tetrathiafulvalene, naphthalenes such as 2,6-dihydroxynaphthalene and 2-naphthol, indoles and sesamol (3,4-methylenedioxyphenol). Polycyclic aromatic compounds in general may find use as suitable electron donors in the present invention. Examples of such compounds include anthracene and naphthacene.

In one embodiment, the guest is anthracene. In one embodiment, the guest is cinnamic acid.

Amino acids, such as tryptophan, tyrosine and phenylalanine may be suitable for use as electron donors. Peptide sequences comprising these amino acids at their terminus may be used. For example, a donor comprising an amino acid sequence N-WGG-C, N-GGW-C or N-GWG-C may be used.

In one embodiment, the guest is tryptophan or phenylalanine. In one embodiment the guest is phenylalanine.

In some embodiments, the guest molecules are a pair of compounds, for example first and second guest molecules, where one of the pair is an A compound as set out in the table above (e.g. A1, A2, A3 etc.), and the other of the pair is a B compound as set out in the table above (e.g. B1, B2, B3 etc.). In one embodiment, the A compound is selected from A1-A43 and A46. In one embodiment, the B compound is B1.

Other suitable guest molecules include peptides such as WGG (Bush, M. E. et al *J. Am. Chem. Soc.* 2005, 127, 14511-14517).

An electron-rich guest molecule may be paired up with any electron-deficient CB[8] guest molecule. Examples of suitable pairs of guest molecules for example first and second guest molecules, for use as described herein may include:
- viologen and naphthol;
- viologen and dihydroxybenzene;
- viologen and tetrathiafulvalene;
- viologen and indole;
- methylviologen and naphthol;
- methylviologen and dihydroxybenzene;
- methylviologen and tetrathiafulvalene;
- methylviologen and indole;
- N,N'-dimethyldipyridyliumylethylene and naphthol;
- N,N'-dimethyldipyridyliumylethylene and dihydroxybenzene;
- N,N'-dimethyldipyridyliumylethylene and tetrathiafulvalene;
- N,N'-dimethyldipyridyliumylethylene and indole;
- 2,7-dimethyldiazapyrenium and naphthol;
- 2,7-dimethyldiazapyrenium and dihydroxybenzene;
- 2,7-dimethyldiazapyrenium and tetrathiafulvalene; and
- 2,7-dimethyldiazapyrenium and indole.

In particular, suitable pairs of guest molecules for use as described herein may include 2-naphthol and methyl viologen, 2,6-dihydroxynaphthalene and methyl viologen and tetrathiafulvalene and methyl viologen.

In one embodiment, the guest pair is 2-naphthol and methyl viologen.

In one embodiment, the guest pair is a reference to a pair of guest molecules suitable for forming a ternary complex with CB[8].

Component

The hydrogel of the invention may hold a component. The hydrogel is suitable for storing a component, and this component may be later released as required at a chosen location.

Some of the present inventors have previously described hydrogels holding components, and the use of the hydrogels to deliver a component to a target location.

See, for example, WO 2013/124654, the contents of which are incorporated by reference herein.

It is understood that a reference to a component held by the hydrogel is not a reference to a solvent molecule. For example, the component is not water or an organic solvent. The component is therefore provided in addition to solvent that may be present within the hydrogel.

It is also understood that a reference to a component is not a reference to a cucurbituril or a monomer used in the preparation of the hydrogel, or other components of the polymerizable composition, or an intermediary product formed from the complexation of cucurbituril with a suitably functionalised monomer, or an intermediary product formed during the polymerization reaction. Otherwise, the component is not particularly limited.

In one embodiment, the component has a molecular weight of at least 100, at least 200, at least 300, at least 1,000, at least 5,000 (1 k), at least 10,000 (10 k), at least 15,000 (15 k), at least 20,000 (20 k), at least 50,000 (50 k), at least 100,000 (100 k) or at least 200,000 (200 k).

The present inventors have previously found that supramolecular hydrogels can usefully hold and deliver a component, such as a bioactive component, to a location.

The activity of the component may be maintained throughout its storage in the hydrogel and after its subsequent delivery to the desired location.

In one embodiment, the component is a therapeutic compound.

In one embodiment, the component is or comprises a biological molecule, such as a polynucleotide (for example, DNA and RNA), a polypeptide or a polysaccharide.

In one embodiment, the component is a polymeric molecule, including biological polymers such as those biological molecules mentioned above.

In one embodiment, the component is a cell.

In one embodiment, the component has a detectable label. The detectable label may be used to quantify and/or locate the component. The label may be used to determine the amount of component contained with the hydrogel.

In one embodiment, the detectable label is a luminescent label. In one embodiment, the detectable label is a fluorescent label or a phosphorescent label.

In one embodiment, the detectable label is a visible label.

In one embodiment, the fluorescent label is a rhodamine or fluorescein label.

In one embodiment, the component is a polypeptide, such as a protein. The protein may be a serum albumin or a lysozyme. Examples of the former include bovine serum albumin.

In one embodiment, the component is a particle. The particle may be a metal particle.

In one embodiment, the component is selected from the group consisting of toxic molecules (such as nerve agents and heavy metals), hormones, herbicides, pesticides, antibodies, pathogens (such as viruses), adjuvants, gels, nanoparticles (including metal or non-metal particles), polymers (including synthetic and natural polymers), catalysts (organic, inorganic, and organometallic), adhesives and sealants.

In another embodiment, the component may be a delivery vehicle, which may be loaded with an agent for delivery, and which agent may be selected from the components listed above. For example, the delivery vehicle may be a capsule, a micelle or a liposome.

The presence of a component within the hydrogel may be determined using suitable analytical techniques which are capable of distinguishing the network material and the component. Such techniques are well known to those of skill in the art.

Methods for the Preparation of Compositions and Hydrogels

The polymerizable compositions of the invention may be easily prepared by simple mixture of the compounds, for example in water, as described above.

In one aspect the invention provides a method for the preparation of a polymerizable mixture, the method comprising the step of mixing the cucurbituril with the polymerizable monomers, such as mixing the cucurbituril and the polymerizable monomers together with water.

The components of the polymerizable composition may be all added together, or the components may be added stepwise. For example, the cucurbituril host may be mixed, for example in water, with the first monomer and optionally the third monomer where present, thereby to form a complex of the cucurbituril with the guests of the monomers. The remaining components of the polymerizable composition may then be added to the mixture. Typically the total monomer concentration, $C_{mon}$, in the polymerizable composition is at least 0.5 M.

Preferably, the polymerizable composition comprises a complex of cucurbituril with a guest or guests provided from monomer in the polymerizable composition. For example, a cucurbituril form a ternary complex with two guests provided from the first monomer. Where a third monomer is present in the polymerizable composition, a ternary complex with guest provided from the first and third monomers may be present, as well as complexes with guest provided from the first monomer only, and the third monomer only.

The amount of cucurbituril held in complex in the polymerizable composition may be at least 5% of the total amount of cucurbituril present, such as at least 10%, at least 20%, at least 50%, at least 60, at least 70%, at least 80%, at least 90%, or at least 95%.

The formation of complexes within the polymerizable composition may be determined by standard spectroscopic methods. For example, the inventors have observed complex formation by US/vis spectroscopy and NMR spectroscopy, amongst others.

The polymerization reaction may be initiated by a polymerization initiator present in the polymerizable composition, and/or by a stimulus, such as light or heat. In the worked examples of the present case, a polymerization photo-initiator is described, and this photo-initiator is activated by UV irradiation of the polymerizable composition.

The conditions for the polymerization reaction are chose appropriately with respect to the monomers present in the polymerization reaction.

The polymerization reaction may be conducted at room temperature, for example at a temperature in the range 10 to 25° C., such as 15 to 20° C.

It follows that the hydrogels of the invention may be prepared under mild and ambient conditions.

The methods of the invention permit the preparation of hydrogels having any desired shape. The shape of the hydrogel material is determined by the reaction vessel used for the polymerization. Thus, an appropriate choice of reaction vessel shape is all that is needed for formation of the desired hydrogel design. Typically, a hydrogel is prepared at a macroscale, therefore the largest dimension of the hydrogel is in the μm, mm or cm range. A reaction vessel is therefore selected that is appropriate for the formation of a hydrogel having such dimensions.

Of course, a product having a desired shape and desired dimensions may be prepared from a larger hydrogel piece, for example by cutting of that large piece into the shape and dimensions desired.

A hydrogel may also be prepared by assembly of a plurality of hydrogel pieces. The present case shows that the hydrogels of the invention have self-healing properties, resulting from the dynamic dissociation and formation of non-covalent crosslinks in the supramolecular network. This same dynamic properties also allow separate pieces of hydrogel material to be brought together and joined. The worked examples in the present case show the fusion of two separate hydrogel pieces into a unified hydrogel form. The rheological studies provided for the hydrogel healing processes in the worked examples show that healed hydrogels can regain the beneficial mechanical properties of the original hydrogel form, given sufficient healing time.

The hydrogel of the invention may hold a component. The component may be introduced into the hydrogel either during hydrogel formation, or the component may be added to a preformed hydrogel, which is then disturbed such as to allow the incorporation of the component therein.

Where the component is incorporated into the hydrogel during hydrogel formation, the component simply needs to be mixed into the polymerizable composition prior to hydrogel formation. The supramolecular network forms around the component thereby to provide a hydrogel holding a component.

Thus, a polymerizable composition of the invention, such as an aqueous polymerizable composition, may further comprise a component. Polymerization of the aqueous polymerizable composition will provide a hydrogel containing the component.

The component does not participate in the polymerization reaction. The component may not possess the functionality of the monomers that is required for polymerization. For example, the component may not include a carbon-carbon double or triple bond, as such may be reactive in a radical polymerization reaction.

Alternatively, a method for preparing a hydrogel holding a component comprises the steps of providing a hydrogel of the invention and agitating that hydrogel in the presence of a component, thereby to incorporate the component into the hydrogel. The agitation step may be a mechanical agitation or disruption of the hydrogel.

The supramolecular complexes of the present invention are reversible, and a complex that is disrupted is capable of reforming, as shown in the worked examples of the present case.

Use of Hydrogel

The hydrogels described herein may find use as materials in medical applications, by virtue of their low toxicity and high water content. The hydrogels of the invention, when suitably loaded with a component, may be used to deliver that component to a target location.

In a further aspect of the invention there is provided a biomaterial comprising a hydrogel of the invention or a polymer of the invention. The biomaterial is for use as a structural element for location on or within an animal, such as a mammal, such as a human. The biomaterial may be an implant. The biomaterial may be provided as a tissue, cartilage or bone replacement material.

In yet a further aspect of the invention, there is provided an electronic device, such as a sensor, comprising the hydrogel or the polymer of the invention. As described herein, a hydrogel of the invention may be ionically conductive, and the hydrogel may be provided as a conductive feature of the electronic device. More generally, the hydrogel materials have beneficial mechanical properties any may provide structure to the electronic device. The polymer of the invention may have similar properties that allow it to be used in a similar way.

The inventors have found that the hydrogels of the invention have excellent adhesive properties. Thus, the invention also provides the use of the hydrogel as an adhesive.

A polymer of the invention may also be used as an adhesive. In a further aspect there is provided as adhesive comprising the hydrogel or the polymer of the invention.

The present inventors have previously found that components held in a cucurbituril hydrogel of the invention may be released from the hydrogel at a chosen location.

Thus, in the present case there is provided a method of delivering a component to a location, the method comprising the steps of:
(i) providing a hydrogel holding a component, as described herein;
(ii) making the hydrogel available at a target location;
(iii) releasing the component from the hydrogel.

In one embodiment, the target location is a location in vivo. Thus, the hydrogel may be placed at a target location in or on a subject. The subject may be a mammal, such as a human or a rodent, such as a rat or a mouse.

In this embodiment, the component may be a therapeutic for use in the treatment or prophylaxis of a disease. The hydrogel comprising the therapeutic compound is therefore suitable for use in methods of treatment of a human or animal body.

In other embodiments, the hydrogel is suitable for delivering a component to a location that is ex vivo, or in vitro.

The present inventors have previously found that changes to a hydrogel composition may be used to change the timing of component release from a hydrogel. Here, timing may refer to the rate at which the component is released, and additionally the timing may refer to change in that rate over time. Thus, changes to the absolute and relative amounts of the components in the polymerizable composition can be used to alter the release profile of the component from the hydrogel.

In one embodiment, a component is released without the application of any external stimulus to the hydrogel. Thus, a hydrogel may be placed at a desired location and the component is simply permitted to leach out of the hydrogel.

In other embodiments, the release of the component may be associated with the at least partial decomplexation of the network. The decomplexation of the complex to separate the guest or guests from the host may occur in response to an external stimulus, including, for example, a competitor guest compound, light, an oxidising or reducing agent, electrochemical potential, and temperature changes amongst others.

Such decomplexation may be induced in order to provide additional or larger pores in the hydrogel through which a component that is held in the hydrogel may pass. Decomplexation may also be used to disrupt the entire network and bring about the breakdown of the hydrogel. Thus, the decomplexation may be initiated by the application of an external stimulus to the hydrogel.

A polymer of the invention may be used in place of the hydrogel in the invention in the methods and uses described above.

Other Preferences

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

Experimental and Results

Materials

Unless otherwise specified, the chemicals used in the current work, including acrylamide, N,N'-methylene bisacrylamide, vinyl imidazole, 1-adamantane amine, benzyl bromide, Irgacure 2959, were purchased from Sigma-Aldrich and were used without further purification. Cucurbit[7]uril and cucurbit[8]uril were synthesized as previously reported (Scherman et al, *Chem. Commun.*, 2010, 46, 2007-2009; Kim et al., *J. Am. Chem. Soc.*, 2000, 122, 540-541).

Instrumentation and Measurement $^1$H NMR (500 MHz) spectra were recorded using a Bruker Avance BB 500. Chemical shifts are reported in ppm (δ).

Photo-irradiation was performed on a photo-reactor with both 365 nm wavelength lamps (power density: 4.8 mW cm$^{-2}$).

A reference to room temperature is reference to an experiment typically conducted at 20° C. or 25° C. Where a temperature figure is not given, a temperature of 20° C. or 25° C. may be assumed.

The instruments and measurements used in the present work are set out below.

Viscosity Test

The polymer solution viscosities were measured using glass, Schott-Gerate Ubbelohde microviscometers with a suspended level bulb using a PVS1 measuring device, and the microviscometers were thermostated in a PV15 water bath at 25° C. using a DLK10 thermostat unit (all manufactured by Lauda). Measured solutions were in Mill-Q (18 mW) H$_2$O at concentrations between 0.01 to 80 g L$^{-1}$.

Tensile Tests

Room temperature (at 20° C.) mechanical testing of the samples was conducted on a tensile Hounsfield machine equipped with a 5-N load cell at a predetermined crosshead speed, and five samples were tested for each case.

Tensile tests were performed on a tensile Hounsfield machine equipped with a 5-N load cell. The experiments were performed at room temperature at deformation rate of 100 mm min$^{-1}$. In order to avoid systematic failure in the vicinity of the clamps, samples were cut using a dumbbell-shaped die cutter following the ISO4661-1 standard with the reduced section of the samples having dimensions of 12 mm×2 mm×2 mm. The work of extension at fracture Wb (J m$^{-3}$), a parameter that characterizes the work required to fracture the sample per unit volume, was calculated from the area below the tensile stress-strain curve until fracture. In the compression test, samples with cylinder shapes (20 mm in diameter and 5 mm in initial thickness) were placed on a metal plate coated with silicon oil to decrease the friction. The loading velocity was typically set at 0.5 mm min$^{-1}$.

ITC Tests

ITC titration experiments were carried out on a VP-ITC from Microcal Inc. at 25° C. in sodium phosphate buffer (pH 7, 10 mM). The aqueous GPC setup consisted of a Shodex OHpak SB column, connected in series with a Shimadzu SPD-M20A prominence diode array detector, a Wyatt DAWN HELEOS multi-angle light scattering detector and a Wyatt Optilab rEX refractive index detector.

In a typical experiment, the host molecules (CB[8]) were loaded in the sample cell at a concentration of 0.05 mM, and the guest molecules (1-benzyl-3-vinylimidazolium) were loaded in the syringe at a 20-fold higher concentration (1 mM). A titration consisted of 20 consecutive injections of 2-10 mL with at least 60 s intervals between injections. The first data point was removed from the data set prior to curve fitting.

Heats of dilution were checked by titration of the guest solution into a buffer solution and subtracted from the normalised enthalpies, even they were relatively small in all cases. The data were analysed with Origin 7.0 software, using the one set of sites model.

Tearing Test

The tearing test was performed to characterize the toughness in air using tensile Hounsfield machine equipped with a 5-N load cell. Samples of ca. 2 mm (w) in thickness were cut into the standard JIS-K6252 ½ dimension (50 mm×7.5 mm; the initial notch length 20 mm). The two arms of a test piece were clamped, and then the upper arm was pulled at 100 mm min$^{-1}$ with the tearing force F was recorded. Tearing energy T was calculated at a constant tearing force F following T=2 F/w, where w is the thickness of the sample.

Pure Shear Test

A pure shear test was also used to characterize the toughness. Two different samples, notched and unnotched, were used to measure the tearing energy T. Rectangular-shaped samples (20 mm (width)×40 mm (length))×1.02 mm (thickness) were used.

An initial notch of 20 mm in length was cut using a razor blade. The test piece was clamped on two sides, and the distance between the two clamps was fixed at 8 mm (L$_0$). The upper clamp was pulled at 100 mm min$^{-1}$, with the lower clamp fixed. The force-length curves of the samples were recorded, and the tearing energy was calculated from T=U(L$_c$)/(a$_0$×b$_0$), where U(L$_c$) is the work done by the applied force to the unnotched sample at the critical stretching distance L$_c$, and L$_c$ is the distance between the two clamps when the crack starts to propagate in the notched sample.

The onset of the crack propagation was determined from a movie image recorded by a camera. The inventors have confirmed that the tearing test and the pure shear test gave the consistent values for the same kind of samples.

Rheological Tests

Rheological tests were performed using a Discovery Hybrid Rheometer (DHR)-2, a controlled stress hybrid rheometer from TA Instruments fitted with a water bath set to various temperatures. All measurements were performed using a 20- and 40-mm parallel plate geometry with a gap of 500 nm. The disc-shaped samples with thicknesses of 0.5 mm and diameters of 20 mm were used and surrounded by a vendor supplied solvent trap in order to mitigate solvent (water) loss during the measurements, and results were analysed using TA Instruments TRIOS software. Generally the rheological tests were conducted at 20° C. or 25° C., except for the temperature sweep experiments the temperature was varied from, for example, 5 to 80° C. (as discussed below).

Dynamic oscillatory strain amplitude sweep measurements were conducted at a frequency of 10 rad s$^{-1}$. Dynamic oscillatory frequency sweep measurements were conducted at a 1% strain amplitude, between 0.01 to 100 rad s$^{-1}$ or 0.01 to 200 rad s$^{-1}$, while temperature frequency sweep tests were done with a shear strain of 1% and shear frequency of 60 rad s$^{-1}$, on a ramp at a rate of 5° C. between 5° C. and 80° C.

Relaxation tests were conducted with a maximum strain amplitude ($\gamma_0$) of 10%, applied within 0.01 s (shear rate 10 s$^{-1}$), then the change of relaxation modulus, G(t), was recorded with time.

Continuous step-strain measurements of the samples at 20° C., 40° C. and 70° C. was conducted at high-amplitude oscillatory (parameters: strain ($\gamma$)=500%, angular frequency ($\omega$)=10 rad s$^{-1}$) and low-amplitude oscillatory parameters: $\gamma$=0.5%, $\omega$=10 rad s$^{-1}$).

Transmittance

Optical transmission spectra of the hydrogels were measured using a UV/Vis spectrophotometer for the whole range of visible light. A quartz cuvette with Milli-Q water (18 mW, 100% transmittance at 550 nm) was used as a reference to reduce the reflection from index mismatch.

Polymer Molecular Weight

A rough estimation of the weight-average molecular weight ($M_w$) for the non-covalent hydrogel was conducted via the overlapping concentration (c*) of the polymer solution where the viscosity increased dramatically. The c* value determined by the viscosity measurement in Milli-Q solution was approx. 26.3 g/L, corresponding to the monomer molar concentration of approx. 0.32 M (excluding CB[8] fraction). As c* is related to the repeat unit size a (approx. 0.2 nm), the average degree of polymerization N, as well as the coil size of a polymer chain R, following the equation:

$$c^* \sim \frac{N}{N_A \frac{4}{3}\pi R^3}$$

Assuming the polymer is a theta state, so R is approx. $aN^{1/2}$, and $$N \sim \left(\frac{3}{4\pi N_A a^3 c^*}\right)^2$$

As a result, the degree of polymerization is N approx. 24,500, and the corresponding molecular weight is around approx. 2.1 MDa, which still falls in the typical MW range of polymers from free radical polymerization. As observed and confirmed by the rheological measurement, a gel network was obtained at 0.4 M monomer concentration (weight fraction of 33 g L$^{-1}$), while for 0.3 M a flow sol solution was obtained. Since the entanglement concentration is just a few times above the overlapping concentration, therefore, polymer chain entanglement is involved in those supramolecular polymer hydrogels, contributing to the extremely toughness and stretchability, together with the CB[8]-mediated host-guest interactions.

Monomer Synthesis

Synthesis of 1-benzyl-3-vinylimidazolium

Benzyl bromide (50 mmol) was added dropwise into a solution of vinyl imidazole (50 mmol) in diethyl ether (100 mL) at 0° C. within 10 min. The reaction was left for another 16 h at room temperature. The reaction crude product was filtered off giving a grey powder, followed by washing with diethyl ether and drying under vacuum to constant weight (yield of ca. 100%).

$^1$H NMR (500 MHz, D$_2$O, 298 K, d, ppm): 10.68 (s, 1H, —N$^+$—CH—N—), 7.17-7.91 (m, 7H, aromatics), 7.22 (dd, 1H, —N—CH=CH$_2$), 5.89 (dd, 1H, —N—CH=CH—Htrans), 5.52 (s, 2H, Ph-CH$_2$—N$^+$—), 5.16 (dd, 1H, —N—CH=CH—Hcis).

Hydrogel Synthesis—Non-Covalent Cross-Links

Predetermined amounts of AAm (95 mole equiv.), 1-benzyl-3-vinylimidazolium (5 mole equiv.) and CB[8] (2.5 mole equiv.) were dissolved in H$_2$O. After purging with nitrogen for 30 min, of photo-initiator (Irgacure 2959, 0.03 mole equiv.) was added to the monomer.

The reaction mixture was transferred into laboratory-made glass molds previously sealed, and then exposed to UV irradiation for 2 h.

The hydrogels were prepared with a total monomer concentration ($C_{mon}$) of from 0.05 M to 2.0 M, including 0.05, 0.1, 0.2, 0.3, 0.4, 0.5, 1.0 and 2.0 M.

A sample of the supramolecular network (prepared with $C_{mon}$ of 2.0 M; diameter 1 cm, thickness 0.5 cm) was completely dissolved in water (~50 mL) after vigorous stirring at room temperature for 5 days. CB[8]-containing polymers were obtained after freeze-drying of the polymer solution. In order to remove the CB[8], the polymer solution was dialyzed against an ADA solution for one week, followed by dialysis against Milli-Q water and freeze-drying. The sample was analysed by $^1$H NMR before and after decomplexation of CB[8]. A ca. 5 mole equiv. fraction for the monomer with a guest was confirmed via the proton signal integration ratio, in agreement with the 5 mole equiv. of the monomer used in the network synthesis.

Figure 5:
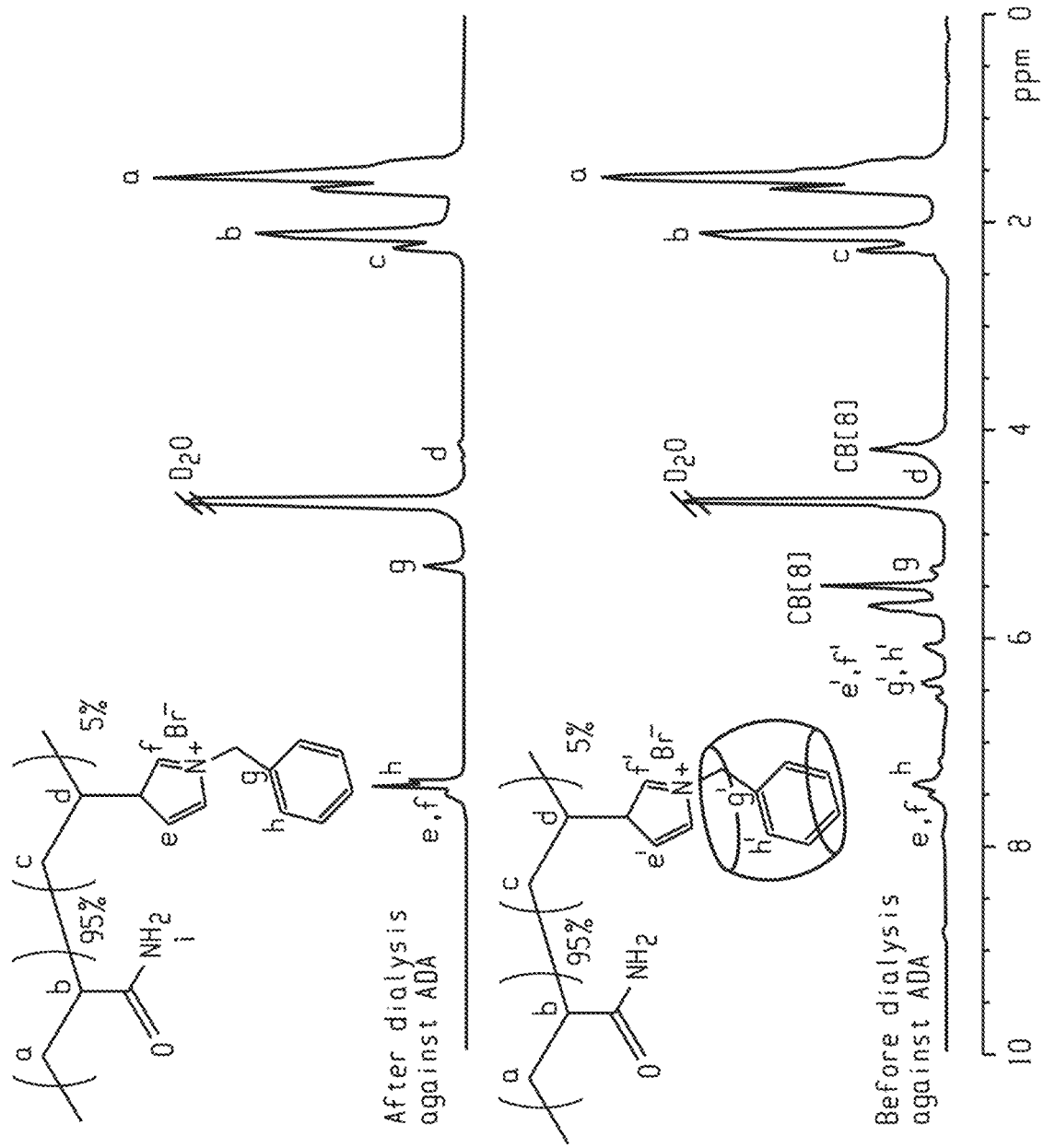
FIG. 5 shows two $^1$H NMR spectra (500 MHz, 298 K) of a polymer obtained (bottom) via a dissolution-freeze drying procedure, and (top) after the dialysis against excessive amount of adamantane amine (ADA), in order to remove the CB[8], followed by the freeze-drying. A 5 mol % fraction was confirmed via the signal integration estimation, in agreement with the 5 mol % stoichiometric feeding ratio.

The chemical shift of the proton signal between the two spectra, arising to the proton in from the benzyl and imidazolium groups (peaks of e', f', g' and h'), also confirms the complexation of the polymer side groups with the CB[8] host molecules, as well as complete removal of CB[8] after dialysis against ADA as competitive guest. The NMR spectra are shown in FIG. 5.

Hydrogel Synthesis—Non-Covalent Cross-Links with Fluorescent Labels

Figure 3A:
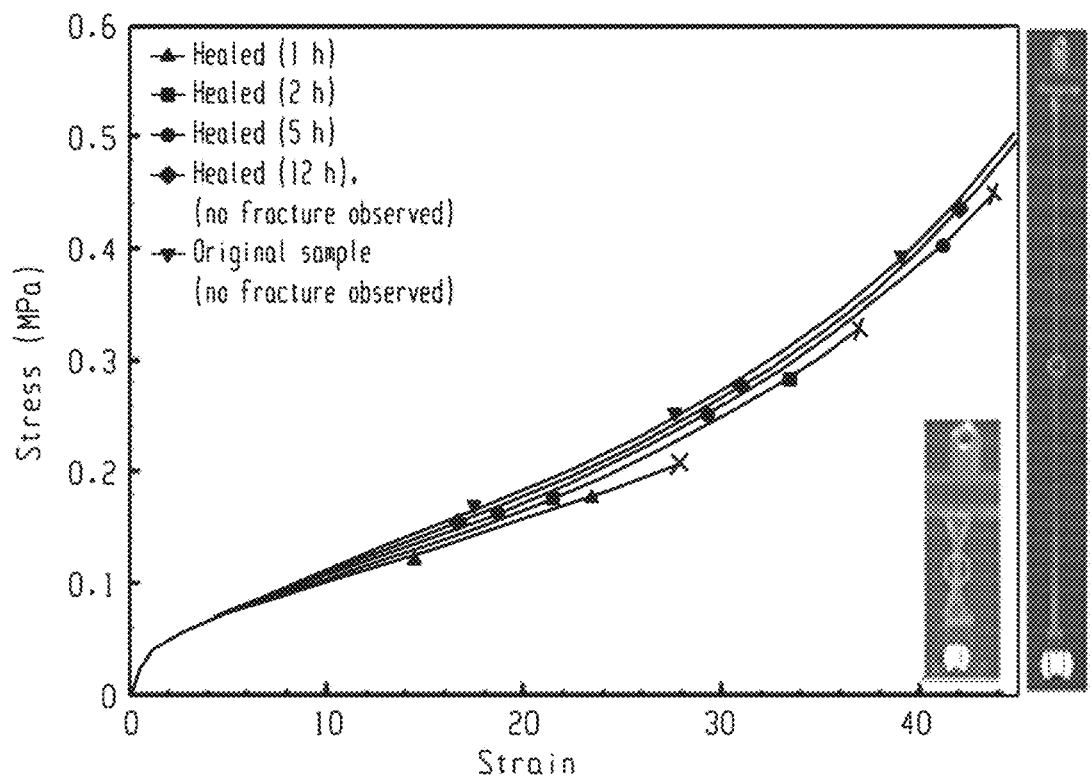
FIG. 3a shows the stress-strain curves of a virgin hydrogel and self-healed hydrogels healed at 25° C. for 1, 2, 5 and 12 hours after fracture (the original sample and self-healed sample after 12 h did not fracture at a strain of 32 mm/mm, the maximum strain could be achieved by the tensile machine). Shown inset are photographs of the dumbbell-shaped polymer network after self-healing upon stretching at a deformation ratio of λ=0, (i) and λ=22, (ii), where the parts marked by a circle indicate the cut part and a hydrogel which is permitted to self-healing at 25° C. for 2 h can sustain a tensile strain of 22 mm/mm before fracture. The change in stress (MPa) is shown with a change in strain (mm/mm)
Figure 3B:
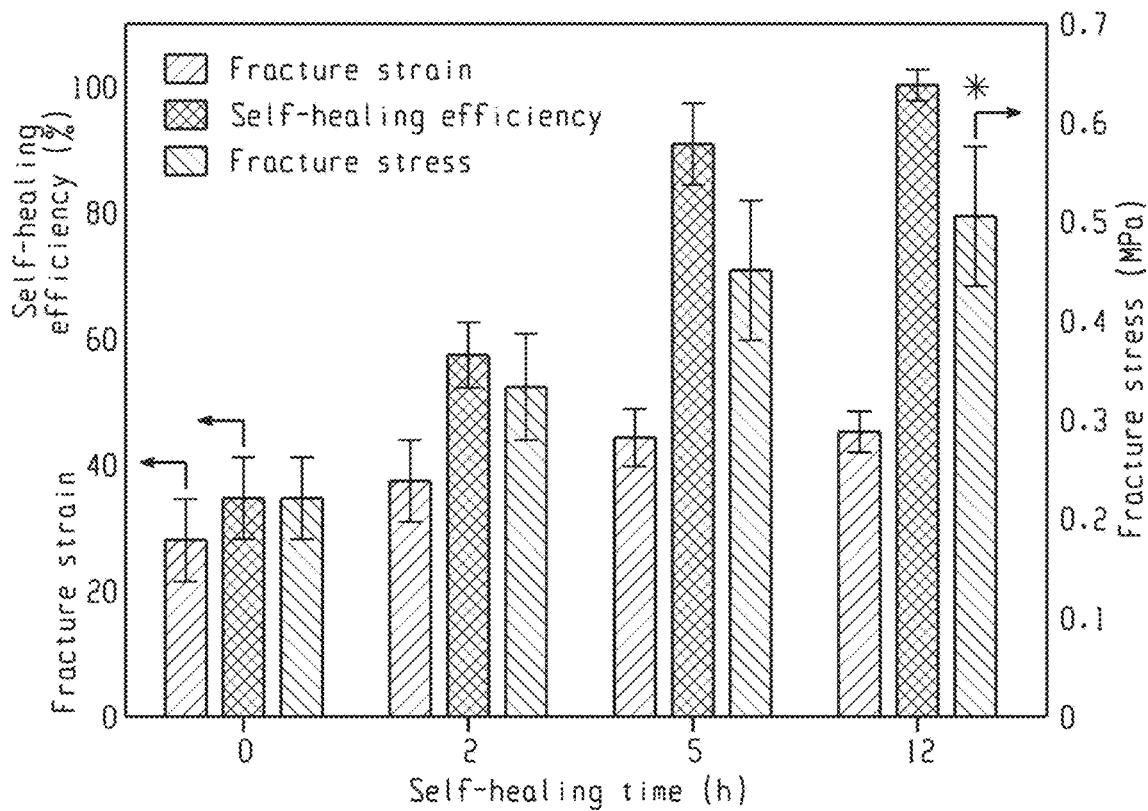
FIG. 3b is a plot of fracture stress (MPa), fracture strain (expressed as the inverse of the stretched length/original length) as well as self-healing ratio (work of the tensile test of the self-healed samples to that of the original sample, the work of original sample at strain 45 mm/mm is taken as 100%)

A fluorescently-labelled hydrogel with non-covalent cross-links was prepared using the method described above for the synthesis of the hydrogel with non-covalent cross-links. To the polymerizable composition was added either rhodamine acrylamide or fluorescein acrylamide (0.002 mole equiv.), and the total monomer concentration was kept at 2.0 M. Two hydrogels samples were prepared, one with the rhodamine label and the other with the fluorescein label. The two samples were used in a healing test, as shown in FIG. 3(c).

Hydrogel Synthesis—Dual Network

Typically, predetermined amounts of AAm (94.95 mole equiv.), 1-benzyl-3-vinylimidazolium (5 mole equiv.), CB[8] (2.5 mole equiv.) and MBA (0.05 mole equiv.) were dissolved in Milli-Q H$_2$O (18 mW). After purging with nitrogen for 30 min, photo-initiator (Irgacure 2959, 0.03 mole equiv.) was added to the monomer solution. The reaction mixture was transferred into a laboratory-made glass mould, and then exposed to UV irradiation (4.8 mW cm$^{-2}$) for 2 h.

The total monomer concentration ($C_{mon}$) was 1.0 M. As with the non-covalent network, the total monomer concentration may be varied in order to adjust the properties of the hydrogel product.

Results—Non-Covalent Network

Figure 1C:
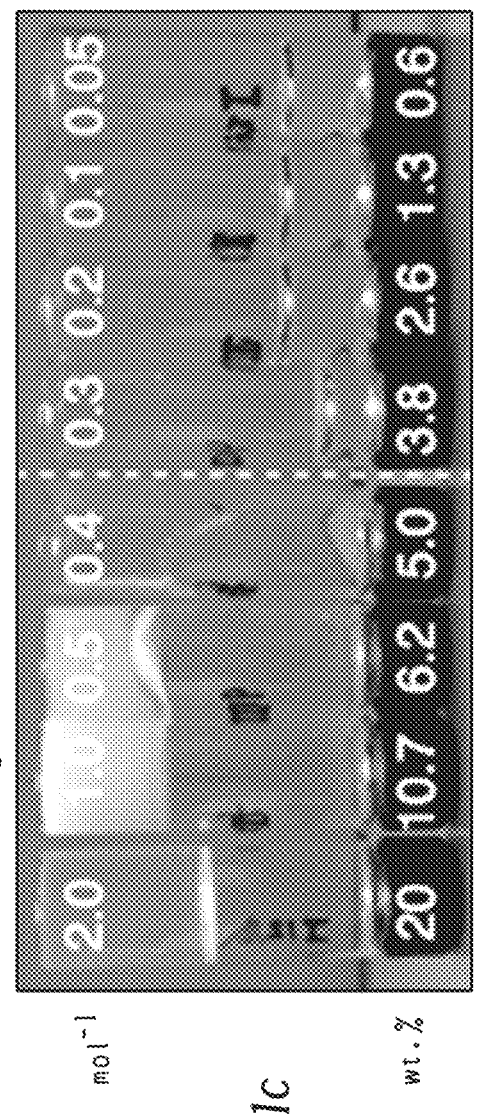
FIG. 1c is photographs of the supramolecular polymer hydrogels at different total monomer concentration (mol/L) or mass fraction (wt %), as well as the invert-vial demonstration of viscosity for each sample.

A hydrogel is prepared from a polymerizable composition comprising the host (cucurbit[8]uril), a monomer having guest molecules (1-benzyl-3-vinylimidazolium) and the monomer acrylamide, which provides the main backbone in the hydrogel product. The dynamic CB[8]-mediated host-guest complexation acts as the sacrificial bonds that rupture under deformation and dissipate the applied energy, which can further re-form leading to the self-healing of the macroscopic supramolecular network As described above, a series of supramolecular polymer networks, with total monomer concentrations ($C_{mon}$) ranging from 0.05 to 2.0 M, were polymerized and examined in an invert-vial test (the results are shown in FIG. 1(c)). An obvious increase in the viscosity was observed with a change in the monomer concentration ($C_{mon}$): with a viscous flow at 0.2 and 0.3 M, and a stable network at concentrations at 0.5 M and above. This indicated that the host-guest interaction between the polymer chains was stabilized at high concentration to form a stable supramolecular hydrogel even without chemical crosslinking.

It was confirmed that there is no covalent crosslinking in the network as they could dissolve completely in Milli-Q water (25° C., 18 mΩ) after 5 days, which can give a fluffy/amorphous polymer after freeze-drying, as well as the subsequent formation of supramolecular polymer network again after re-dissolution in water (results not shown). The strong concentration effect on the gelation is attributed to the entanglement of polymer chains. A rough estimation of the overlapping concentration from the molecular weight of the sample supports this argument (see Polymer Molecular Weight discussion above). The fact that the critical Cm of gelation shifted to a lower value when adding a small amount of chemical crosslinker also supports this argument (see the double network system described below).

Figure 6A:
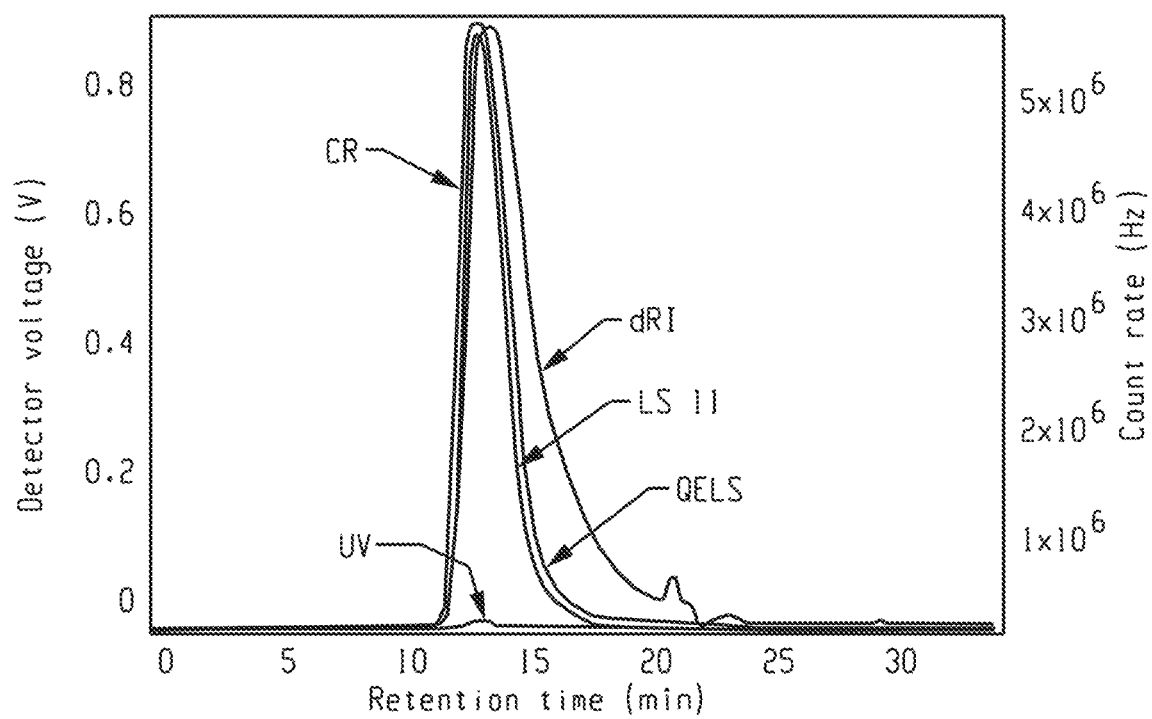
FIG. 6a shows an aqueous GPC trace of the as-obtained polymer (with CB[8] removed) from a supramolecular polymer hydrogel, giving a weight-average molecular weight ($M_w$) of 2.53 MDa ($M_w/M_n$=1.9), which falls in the typical $M_w$ range of free radical polymerization.

FIG. 6(a) shows the GPC trace of a freeze-dried polymer after dialysis against excessive ADA solution (1 mM). Here, CB[8] molecules were completely removed from the polymer by the competitive formation of ADA complexes, as confirmed by the NMR analysis.

Figure 6B:
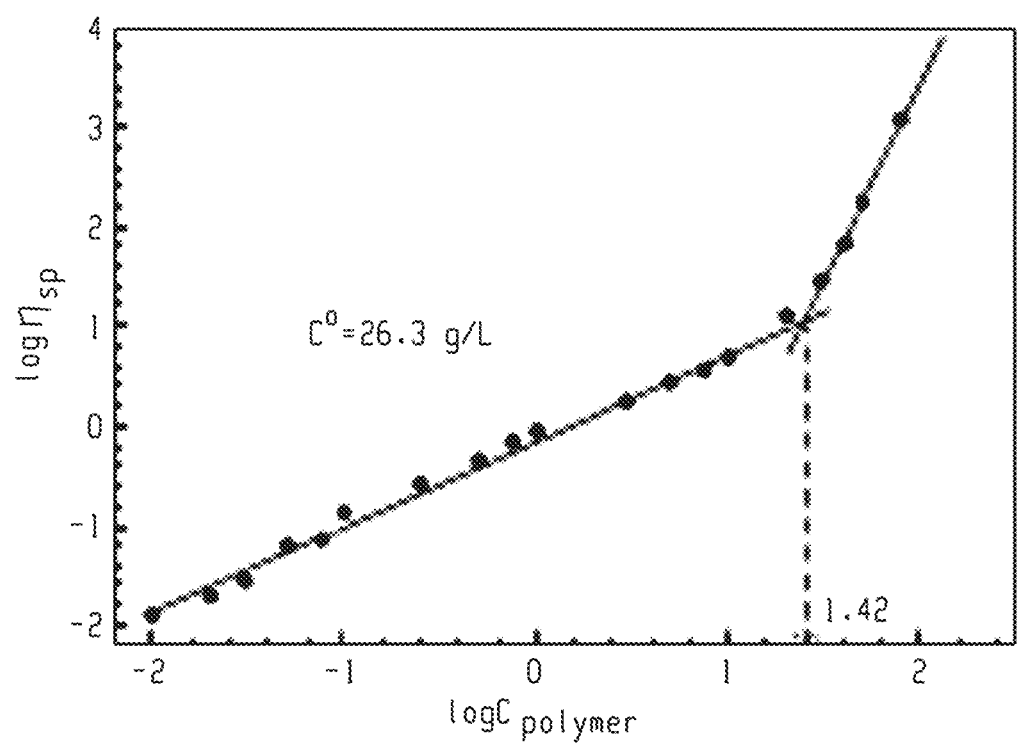
FIG. 6b shows log-log plotting of the specific viscosity against polymer solution (with CB[8] removed) via the viscometer measurement, as well as the linear plotting of the data points in the range of −2-1 (0.01-10 g/L) and 1-1.9 (10-80 g/L), give a crossing point at 1.42 (26.3 g), namely the overlapping concentration.

Polymer solutions with concentrations ranging from 0.01 to 80 g/L were prepared in Mill-Q (18 mΩ) water, and the viscosity of the polymer solution was measured using glass, Schott-Gerte Ubbelohde microviscometers at 25.0° C. Two sets of linear plots were generated to give a critical entanglement concentration at the crossover point (see FIG. 6(b)).

Figure 2A:
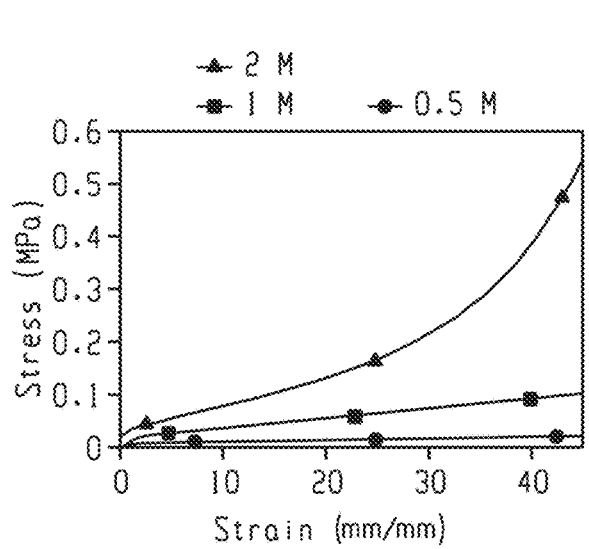
FIG. 2a the uniaxial tensile behaviour of hydrogels prepared from a polymerizable composition having a total monomer concentration of 0.5 M (bottom line), 1 M (middle line) and 2 M (top line) at a deformation rate of 100 mm/min.

The tensile stress-strain curves of the supramolecular polymer network (FIG. 2(a)) demonstrate that increases in $C_{mon}$ remarkably enhance the mechanical performance.

The gels synthesized at low monomer concentrations (e.g. $C_{mon}$ 0.5 M) do not show an obvious yielding point, indicating weak chain entanglement, whereas the gels synthesized at higher concentrations (e.g. $C_{mon}$ 2.0 M) exhibit clear yielding points with markedly enhanced modulus. Apparently, the enhanced mechanical strength is due to the strong chain entanglement, coupling with the inter-chain CB[8]-mediated host-guest complexation, at elevated concentration. This is also corroborated by the controls with CB[7] or without CB[n], which could only give a highly viscous fluids, with modulus lower by 2 magnitudes (see FIG. 10).

Moreover, the distinct yielding observed beyond a certain strain should stem from the internal rupture of host guest complex. It is of interest to note that such kind of supramolecular polymer network can be stretched beyond 45 times of the original dimension (maximum stretch obtainable from the tensile machine) without fracture observed during the tensile test (results not shown). A simple weight-lifting test shows that a network ribbon could easily lift a weight 500 times heavier than the network itself (results not shown).

Figure 2B:
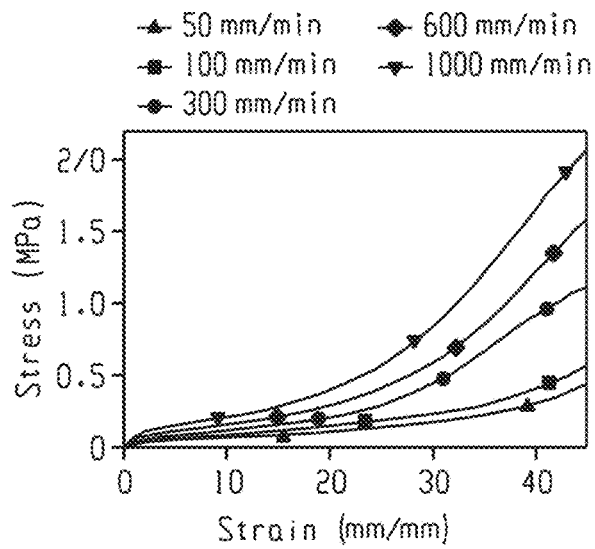
FIG. 2c shows the uniaxial tensile behaviour of a hydrogel prepared from a polymerizable composition having a total monomer concentration of 2 M over cycles of loading and unloading to variant strains. The deformation rate was 100 mm/min.
FIG. 2d shows the uniaxial tensile behaviour of a hydrogel prepared from a polymerizable composition having a total monomer concentration of 2 M. Immediately after strain is applied, (bottom curve at 40 mm/mm), after the first cycle of loading and unloading at a strain of 8 mm/mm (bottom curve at 6 mm/mm), and a hydrogel sample which was self-repaired at rt for 30 min (top curve at 40 mm/mm) after stress. The high overlapping of the normal run curve (second from top curve at 40 mm/mm) and the self-repaired sample after 30 min indicates the almost complete self-reparation of the network via the reformation of previously-cleaved supramolecular bonding. In all figures, the change in stress (MPa) is shown with a change in strain (mm/mm).

The deformation-rate dependence of tensile behaviour also confirms the physical picture described above (FIG. 1(a)). The pronounced increase in the strength and Young's modulus (24 times from 0.016 MPa at 10 mm/min to 0.42 MPa at 2,000 mm/min) of the supramolecular polymer hydrogel with the deformation-rate increase indicates the dynamic and reversible features of less stable host-guest interactions within the entire deformation rate range, whose features are absent in traditional covalent networks (FIG. 2(b)). This viscoelastic feature contributes to the high shock-absorption ratio and toughness of the supramolecular networks. It is noted that no fracture was observed before the stretching ratio of 45 (the maximum ration that could be achieved by the tensile machine used in the study), despite of the deformation speed increases from 10 to 2,000 mm/min.

Figure 2C:
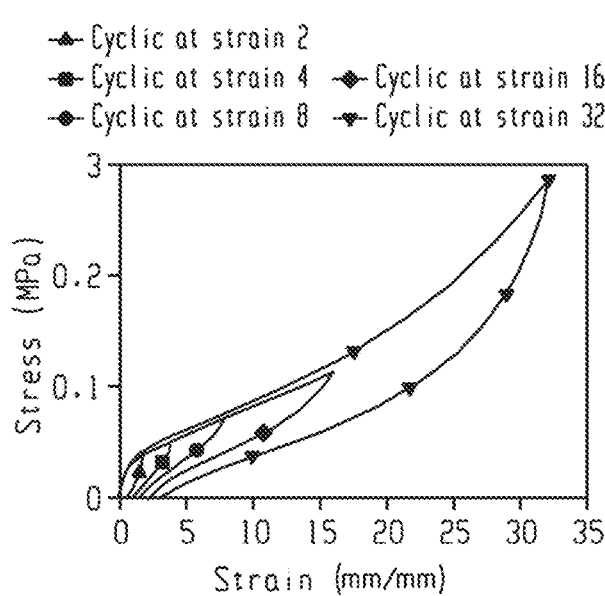

To further justify the viscoelastic properties of the supramolecular network, the inventors performed cyclic tensile tests to observe the hysteresis of the deformation and its recovery. As shown in FIG. 2(c), a clear yielding is observed upon loading the sample to a predefined tensile strain and a large hysteresis is observed upon unloading to zero stress. A residual strain was observed at zero stress. The yielding reveals the structural change of the gel, i.e., dissociation of supramolecular host-guest complex that dissipates the energy. The residual strain and hysteresis reveal that the structural change is preserved within the unloading time. The residual strain decreased to zero after a certain waiting time.

Figure 2D:
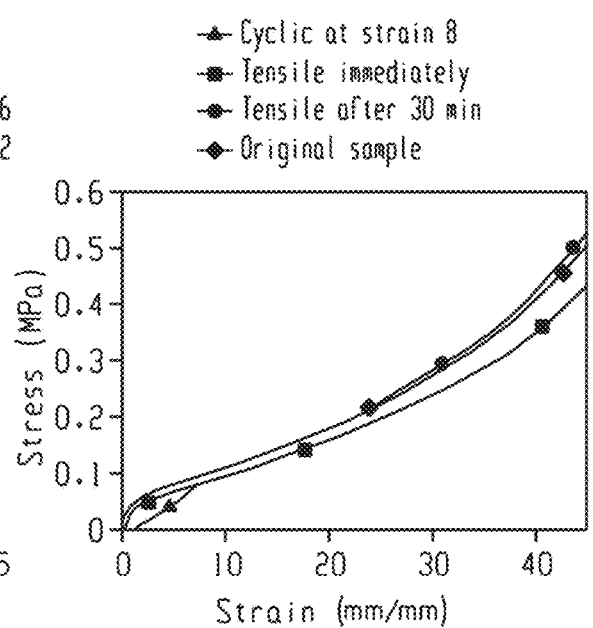

As shown in FIG. 2(d), a decrease in both modulus and stress was detected in the tensile run immediately after the cyclic tensile test at a strain of 8. However, upon a waiting period of ca. 30 min, the sample recovers all of the mechanical properties, as evidenced by the overlapping of the tensile curve with the original one. This indicates that even without covalent cross-linking, no chain sliding occurs under the large deformation because of wide distributions of host-guest complexation within the network. Moreover, the CB[8]-mediated host-guest complexes serve as reversible sacrificial bonds, which break and reform dynamically, giving high toughness to this novel viscoelastic supramolecular polymer network.

Figure 7:
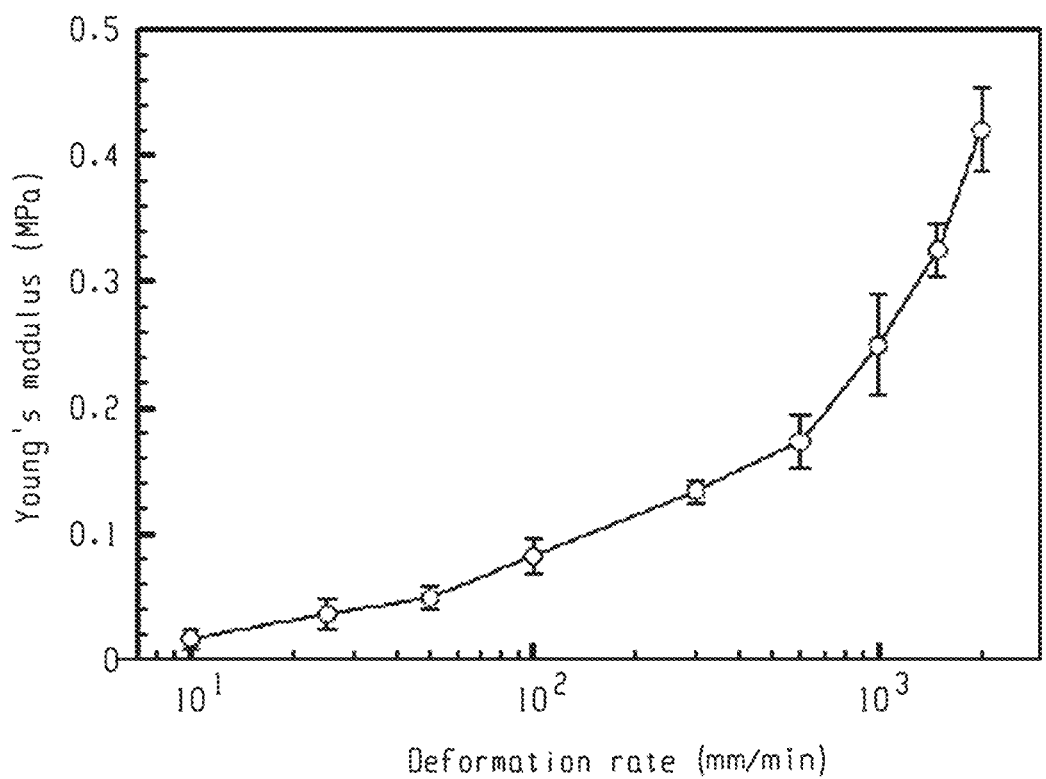
FIG. 7 shows the change in Young's modulus (MPa) with change in the deformation rate (mm/min) for a hydrogel prepared with a total monomer concentration of 2.0 M. Here, a quantitative increase in Young's modulus was estimated with an approx. 24-time increase when the deformation rate was increased from 10 (0.017 MPa) to 2,000 mm min$^{-1}$ (0.42 MPa).

FIG. 7 show the change in Young's modulus with the change in the deformation rate for the hydrogel sample (prepared at $C_{mon}$ of 1.0 M). The presence of cucurbituril host guest interactions imparts remarkable viscoelasticity on the network, thus higher modulus values are observed at higher deformation rates. This can be contrasted with covalently-crosslinked hydrogel systems which display a dependence on the deformation rate due to the elastic essence of the material.

Although several gels of high strength and toughness based on physical association have recently been developed (see Sun et al. Nature; Haque et al.; Tanaka et al.), most of them only have partial self-recovery ability, probably due to some permanent damage of covalent bonds upon loading. Thus, a delicate balance between the physical bonds of the rigid and brittle nature and the covalent bonds of the soft and ductile main chain is crucial for the tough hydrogels.

Figure 8:
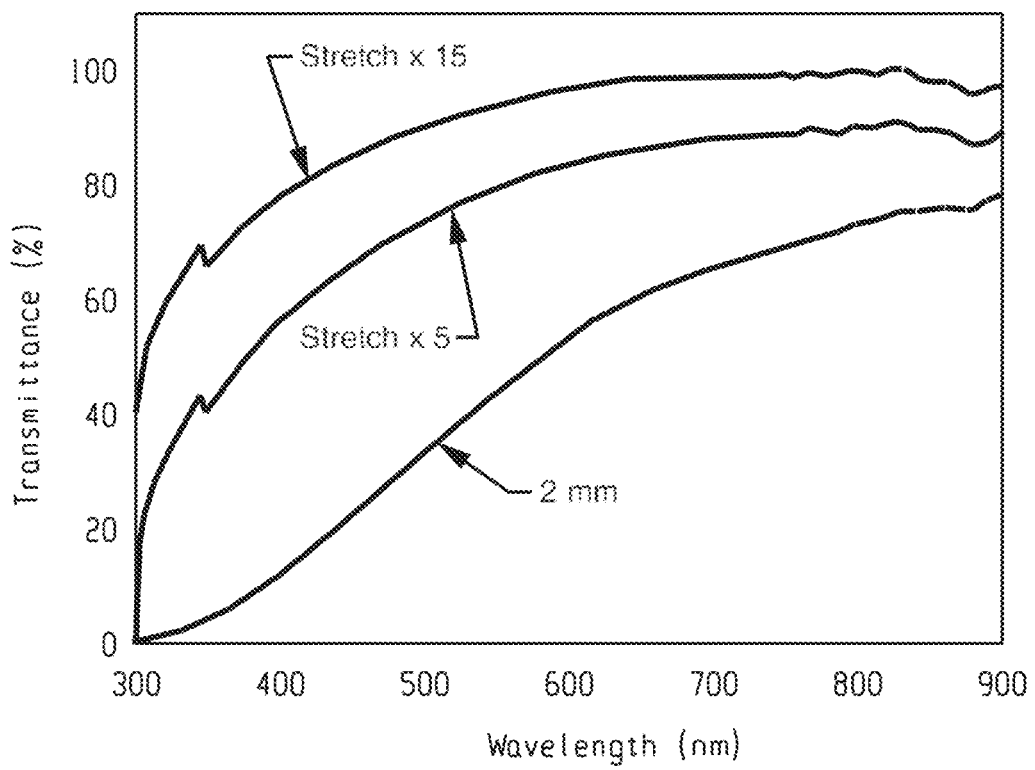
FIG. 8 shows the change in transmittance (%) with change in wavelength (nm) for a hydrogel prepared with a total monomer concentration of 2.0 M with change in stretching, where a film with original thickness of 2 mm was stretched to the strain of 5 and 15 under uniaxial stretching, respectively, upon the fixation of the two ends to a UV/vis spectra holder, the transmittance of the samples were recorded, with a cuvette filled with Milli-Q water as blank.

The hydrogel has a relatively high visual light transmittance across the range 600 to 900 nm (see FIG. 8, for a film sample prepared with at $C_{mon}$ of 1.0 M having a thickness of 2 mm prior to stretching). The light transmittance in the visible range is moderate, and this increases upon stretched for example when the sample is stretched 5 times or 15 times (FIG. 8).

Traditional covalent hydrogels are too brittle to sustain compression, slicing or elongation (see Aida et al.; Yan et al.). However, with the presence of CB[8]-mediated supramolecular host guest complexation to dissipate the energy, the supramolecular networks are highly elastic and stretchable, behaving like rubbers. The network samples are very elastic and are able to withstand high compression, or high level of deformations such as bending, twisting, knotting and extensive stretching.

Moreover, the network could also hold a slicing with blade, leaving a trace, which can be quickly healed in few minutes (results not shown). From the proposed chemical/topological network structure, the supramolecular polymer network built with these supramolecular interactions is assumed to have a relatively uniform and large length. They exhibit a natural coil state if no load is applied. They can be elongated under stress until they become straight, and can recover to the lowest energy coil state when the stress is taken away. Thus, the stress can be dissipated effectively to the dissociation of those host-guest supramolecular crosslinking.

The supramolecular polymer network was also extremely notch-insensitive: a virgin supramolecular network with a sheet-shape could be stretched to 25 times its original length without rupture, while subsequent fracture was observed near the glass or metal clamp, where all intensive stress accumulated. When a notch was cut into the gel and then pulled it, the notch was dramatically blunted and remained stable before the stretch ratio of 13.8 and 15.5, respectively. After the critical applied stretch, a crack initiated at the front of the notch, and ran rapidly through the entire sample. At a critical applied stretch (strain of 10), a large, recoverable deformation is demonstrated by dropping a metal ball on a membrane of the gel fixed by circular clamps. On hitting the membrane, the ball stretched the membrane greatly and then bounced back. The membrane remained intact, vibrated, and recovered its initial flat configuration after the vibration was damped out. A ball with greater kinetic energy, however, caused the membrane to rupture after large deformation.

Room-temperature self-healing efficiency testing was carried out with a dumbbell-shaped sample, which was cut into two pieces and then brought into contact for a range of different self-healing times. The healing efficiency, defined as the ratio between the work required to break the healing joint, and the work required to break the virgin sample by tensile deformation, reached approx. 35% after 1 h healing at room temperature. The healed joint was able to withstand a very large stress (approx. 40% of the original stress, see FIG. 3(a)), with a deformation ratio of approx. 28, followed by a fracture of the healed part (see FIG. 3(a)(ii) and (iii), the circles indicate the location of the fracture).

A longer self-healing period of 12 h can lead to almost complete self-healing of the material. This high self-healing efficiency is also comparable with previously reported self-healing system based on hydrogel bonding (Cordier et al.; White et al.; Chen et al.; Wang et al.; Tee et al.), metal-ligand conjugation (Burnworth et al.), electrostatic interaction (Sun et al. *Nat. Mater.*), and host-guest interactions (Nakahata et al.), amongst others.

Furthermore, adhesion between uncut surfaces was also observed by fluorescence microscopy imaging of fluorescently-labelled hydrogels. The hydrogels were prepared as before, with the addition of small amounts of red- or green-labelled monomers to the polymerizable compositions (0.002 mole equiv. fluorescent monomer to 95 mole equiv. of AAm), which were then polymerized to give red- and green-labelled hydrogels. The hydrogels were brought into contact, and the fluorescently imaged. The appearance of yellow region, corresponding to the overlap of red luminance (RITC) and green luminance (FITC), corroborated the self-healing at the contact area.

Ionic conductors generally have higher resistivity than most electronic conductors.

However, when high stretchability and transmittance are required, ionic conductors have lower sheet resistance than electronic conductors such as silver nanowires, single-wall carbon nanotubes, graphene, and indium tin oxide (see Keplinger et al.).

Figure 4A:
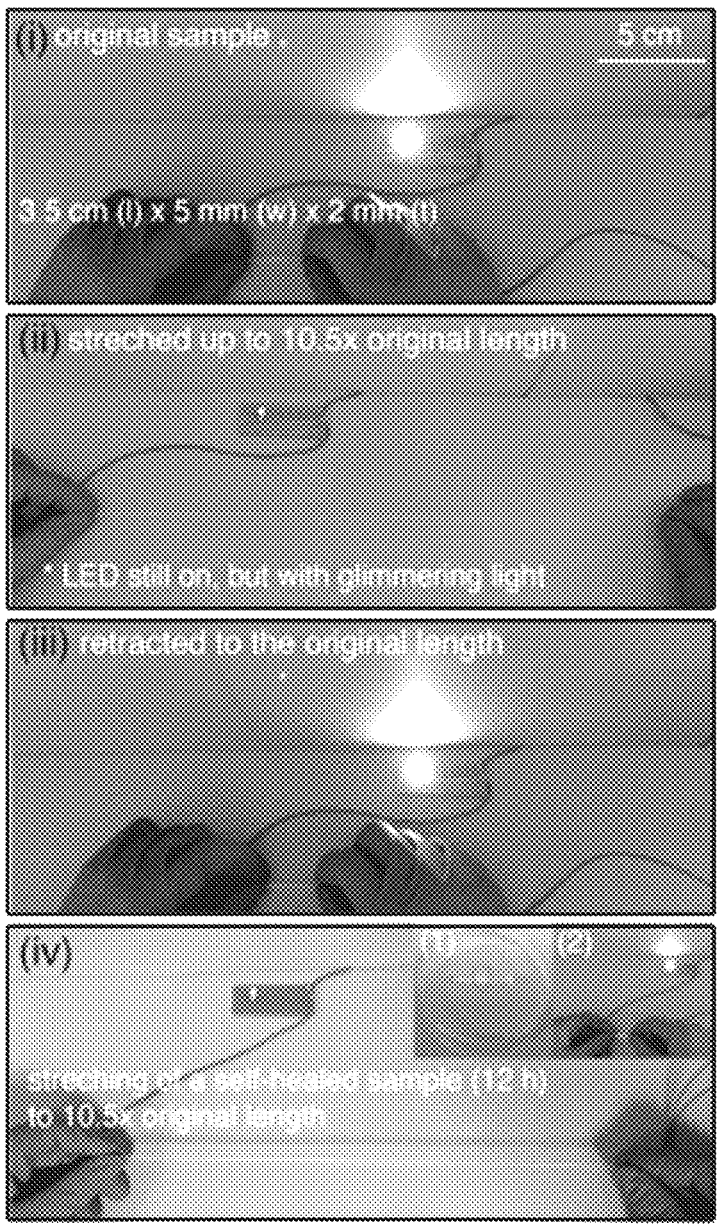
FIG. 4a shows a visual demonstration of the supramolecular polymer network as conductor to light LED bulb when connected with a battery, before (i) and after (ii) the sample was stretched to a strain λ=10.5, recovered to its original length (iii), as well as using of a self-healing sample (12 h, (iv)(1)) as a conductor, before ((iv)(2)) and after (iv) stretching to a strain of λ=10.5.
Figure 4B:
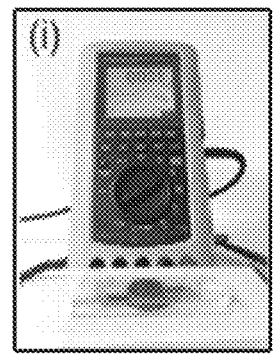
FIG. 4b shows a visual demonstration of the pressure sensing with the network sample connected to a multimeter (voltage channel), before (i) and upon (ii) compression (ca. 30% deformation), as well as compression removal and voltage signal recovered to the original value within 18 s (iii)
Figure 4B:
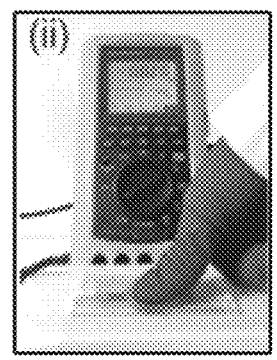
Figure 4B:
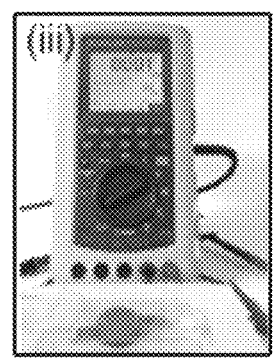
Figure 4C:
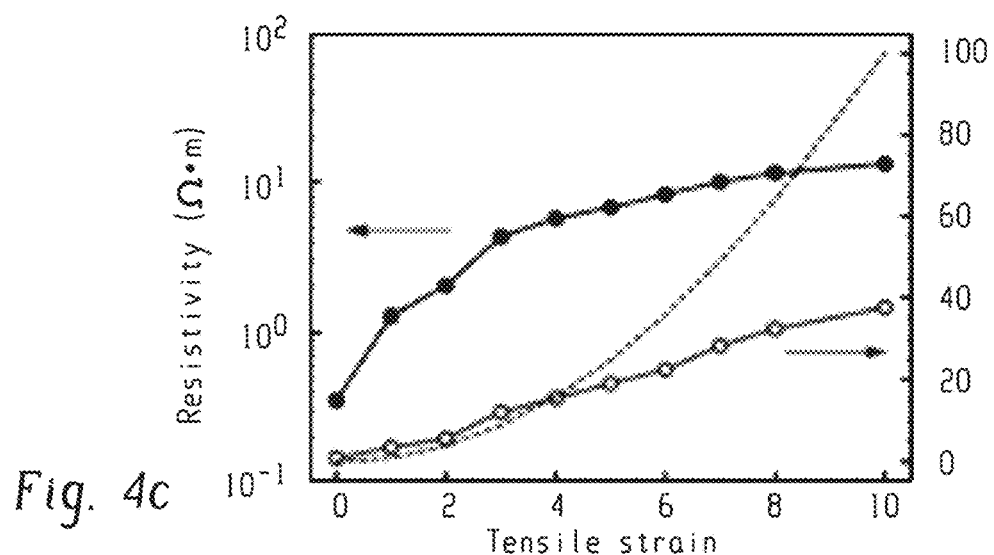
FIG. 4c shows the change in resistivity (Ω·m) and relative resistance (R/R$_0$) with change in tensile strain (as expressed in relation to the ration of length of the stretch sample to the length of an unstretched sample)

FIG. 4(a) shows that the supramolecular polymer network is conductive enough to power a LED light, even when the hydrogel is stretched by up to five times along its length (see FIG. 4(a) (ii)). In addition, the resistance of the network increased by two times once stretched by four times, due to the increase in length and the decreased intersect surface area (FIG. 4(c)). However, the resistivity of the network (1 to $15 \times 10^{-3}$ Ω·m) is two orders higher than that of sea water (approx. 0.2 Ω·m).

Figure 4D:
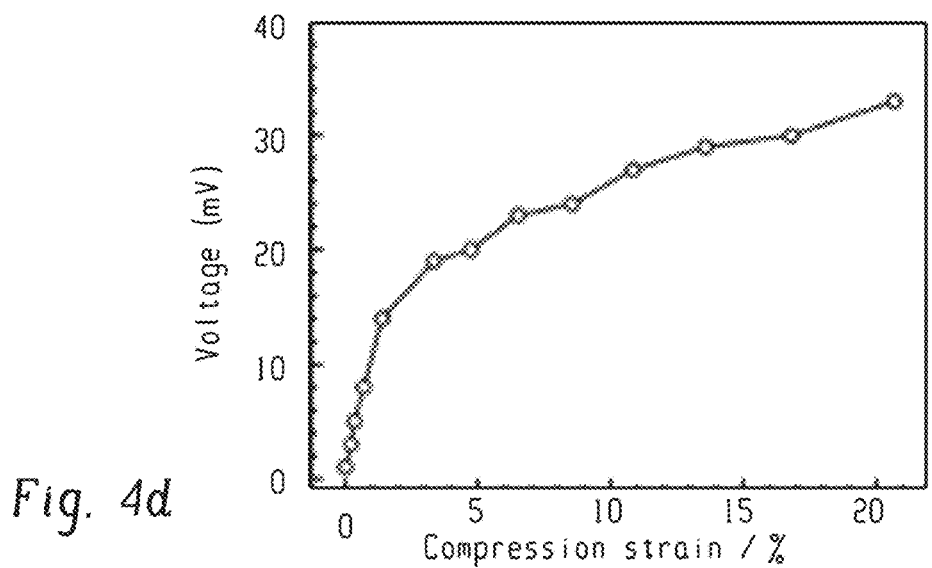
FIG. 4d shows the change in voltage (mv) with change in compression strain (%)
Figure 4E:
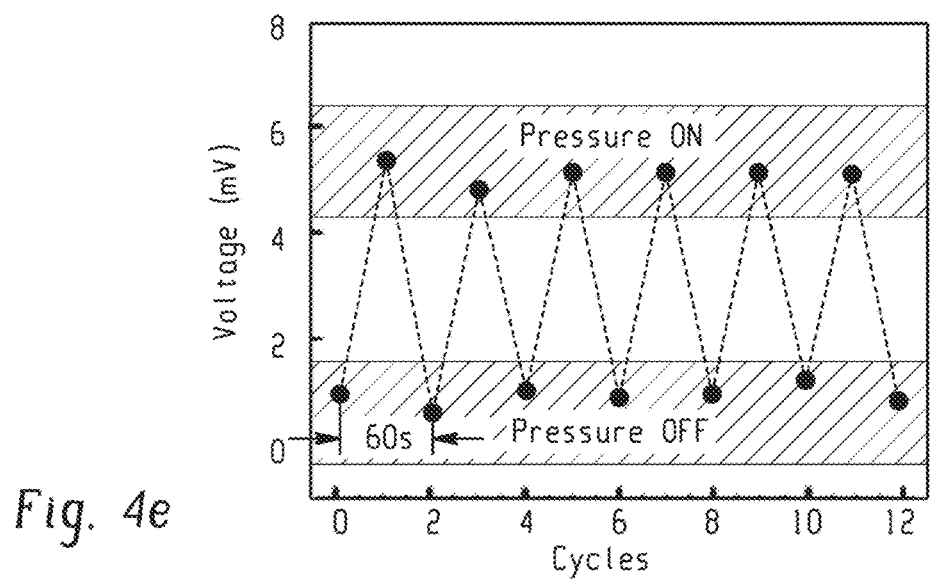
FIG. 4e shows the change in voltage (mv) during a cyclic compression/decompression cycles upon a compression strain of 2% (stress of ca. 0.35 kPa), with an interval of 60 s for each cycle. In all experiments the virgin hydrogel is a non-covalent hydrogel prepared from a polymerizable composition having a total monomer concentration of 2 M.

Under compression, the measure voltage is seen to increase, with a significant increase in the initial compression range (from 0 to 5%) (see FIG. 4(d)). The change in voltage during a cyclic compression/decompression cycles was also studied. The results are show in FIG. 4(e).

Figure 11A:
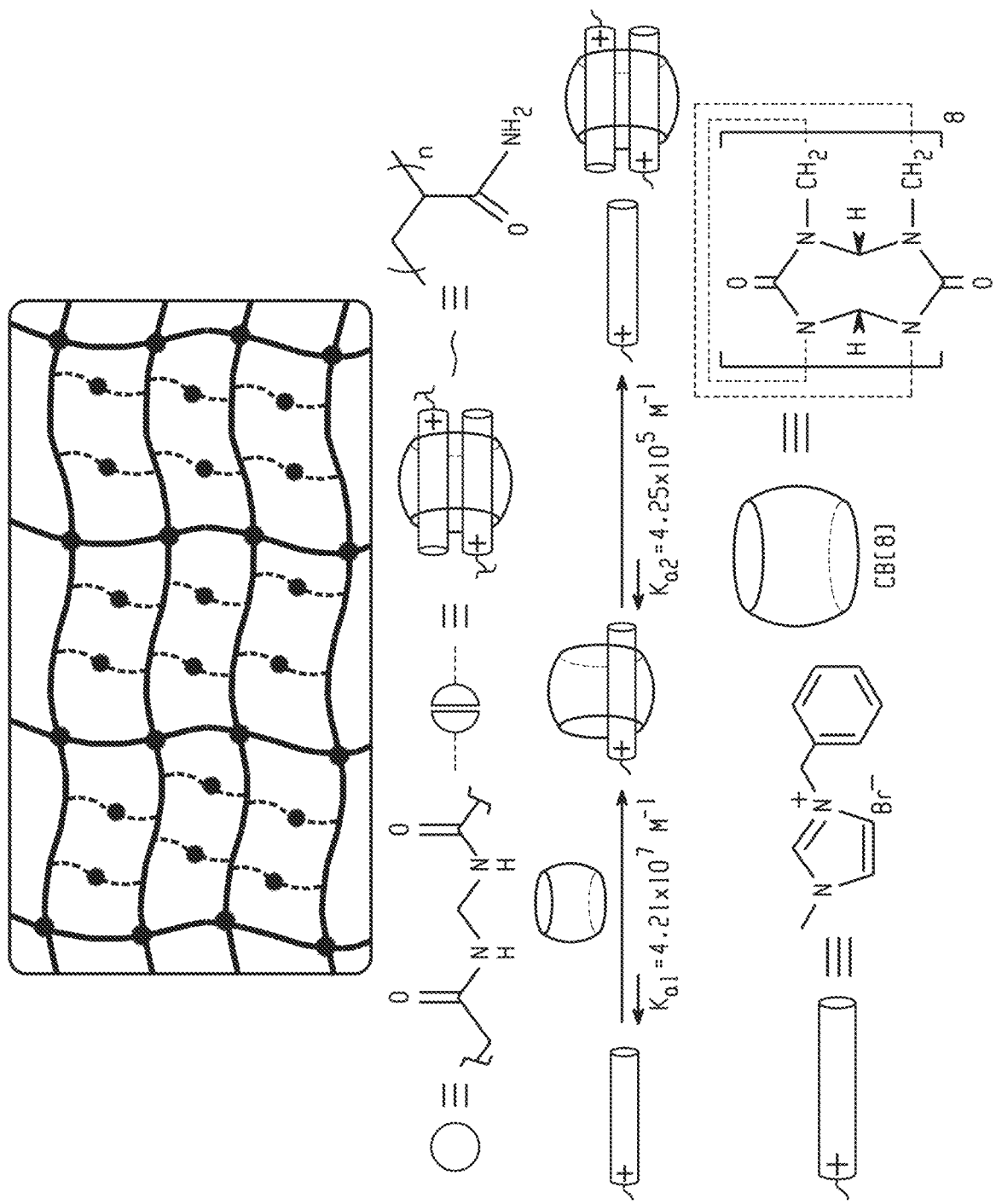
FIG. 11a shows the concept of biomimetic modular hierarchical supramolecular dual network design, where a schematic illustration of a modular dual network composed of supramolecular physical host-guest crosslinks (blue circles) and permanent crosslinks (pink circles). The three-component CB[8] ternary complex in a 1:2 stoichiometric ratio.
Figure 15:
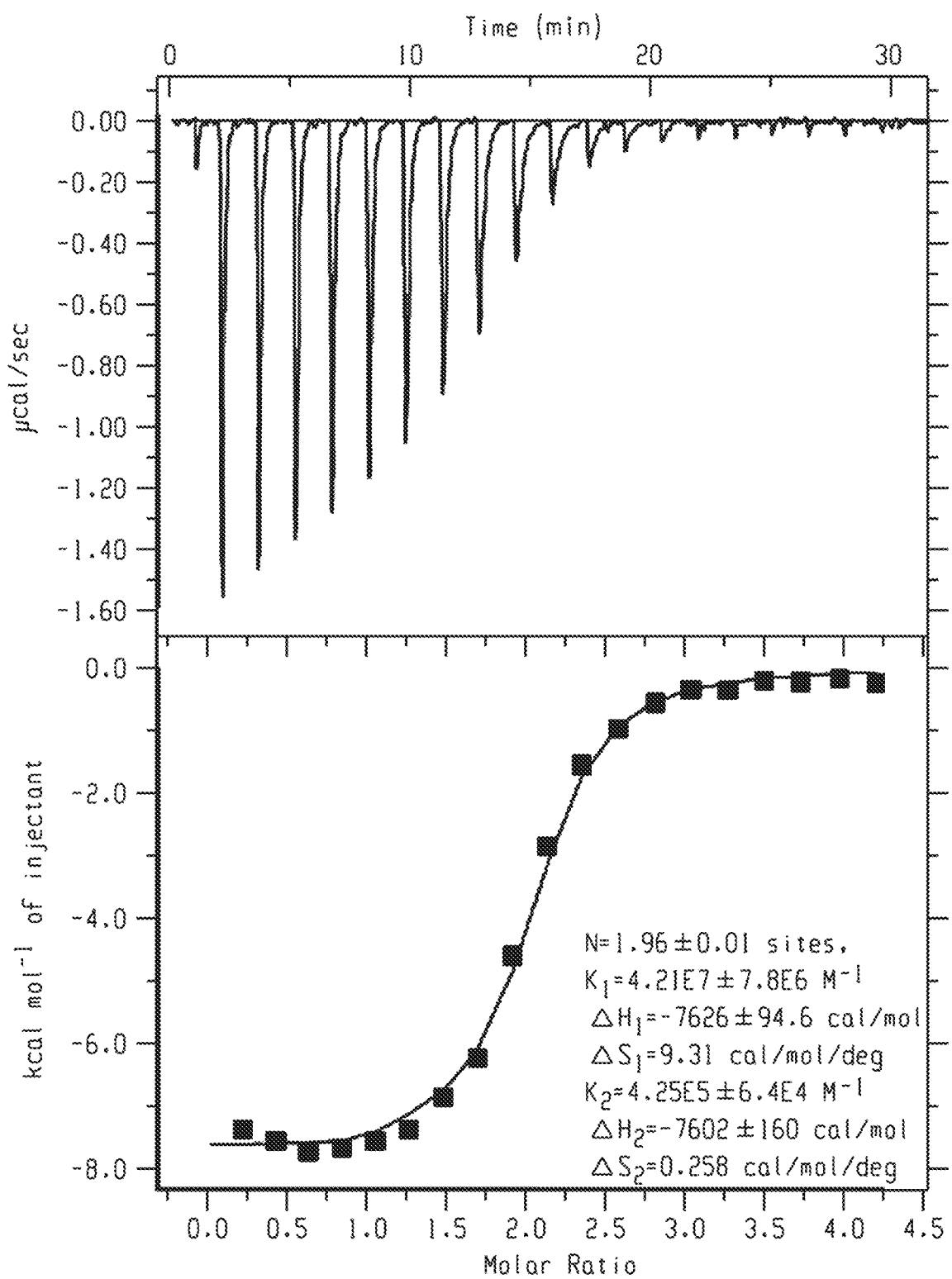
FIG. 15 shows the ITC titration of 1 mM 1-benzyl-3-vinylimidazolium solution into 0.05 mM CB[8] solution (both prepared in 10 mM PBS buffer, pH 7, 25° C.). A high binding constant of 1.8×10$^{13}$ M$^{-2}$, entropy of 7.63 kJ mol$^{-1}$ (ΔH$_1$) and 7.60 kJ mol$^{-1}$ (ΔH$_2$) were detected for the 2:1 binding. The binding energy is comparable to the protein folding within titin, corroborating the use of the materials as biomimicks.
Figure 20:
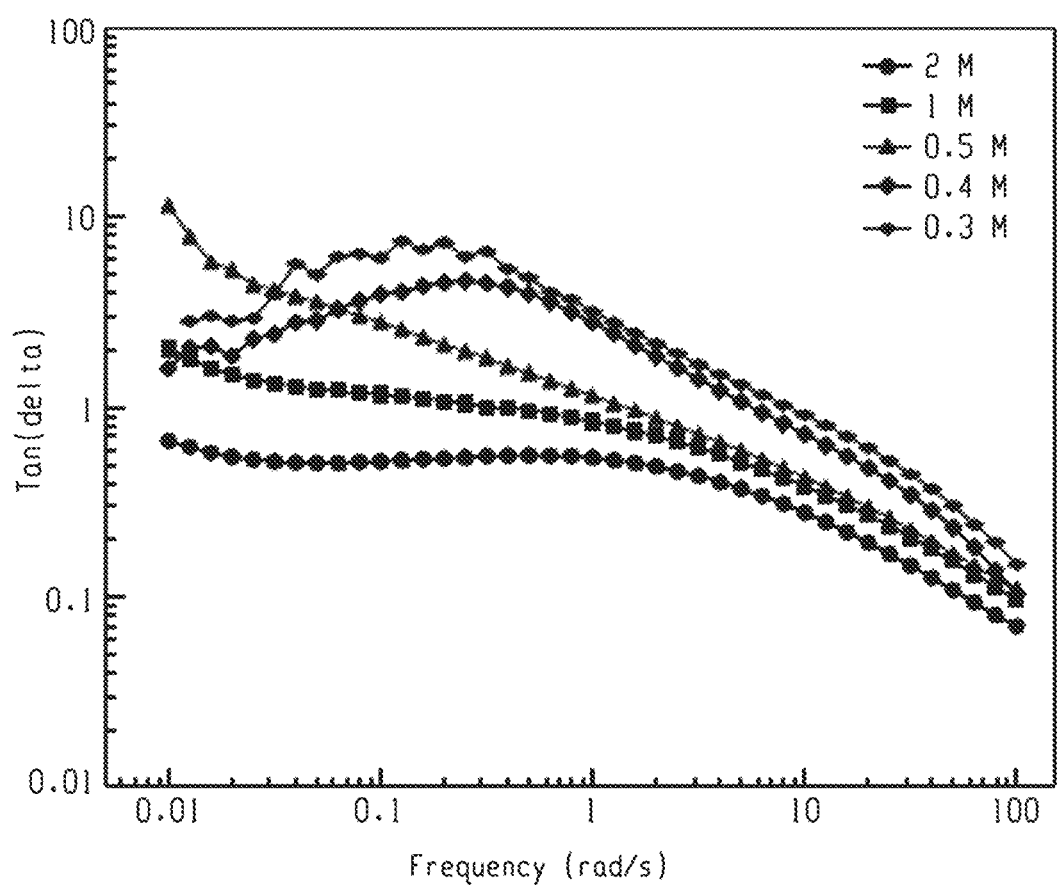
FIG. 20 shows the change in tan (δ) with change in frequency (rad/s) for five hydrogels prepared from a polymerizable composition having a total monomer concentration of 0.3 M (top line at 100 rad/s), to 2 M (bottom line at 100 rad/s). The hydrogels have a supramolecular non-covalent network. In all experiments the virgin hydrogel is a non-covalent hydrogel.
Figure 21A:
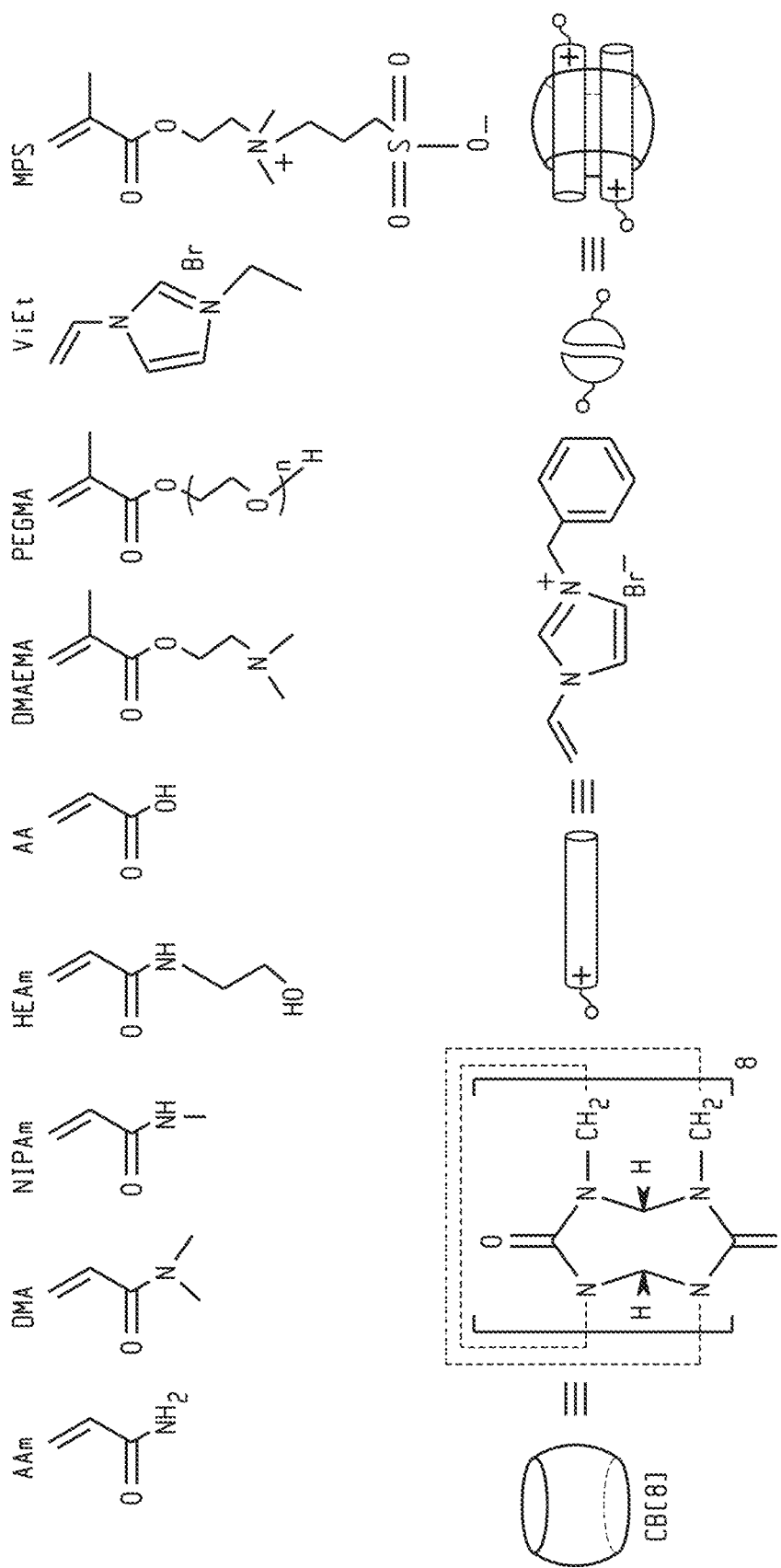
FIG. 21a shows example monomers for use as second monomers in a polymerizable composition according to an embodiment of the invention (top line), the structure of CB[8], and a schematic for the formation of a ternary complex of the first monomer 1-benzyl-3-vinylimidazolium bromide with CB[8] (second line)
Figure 21B:
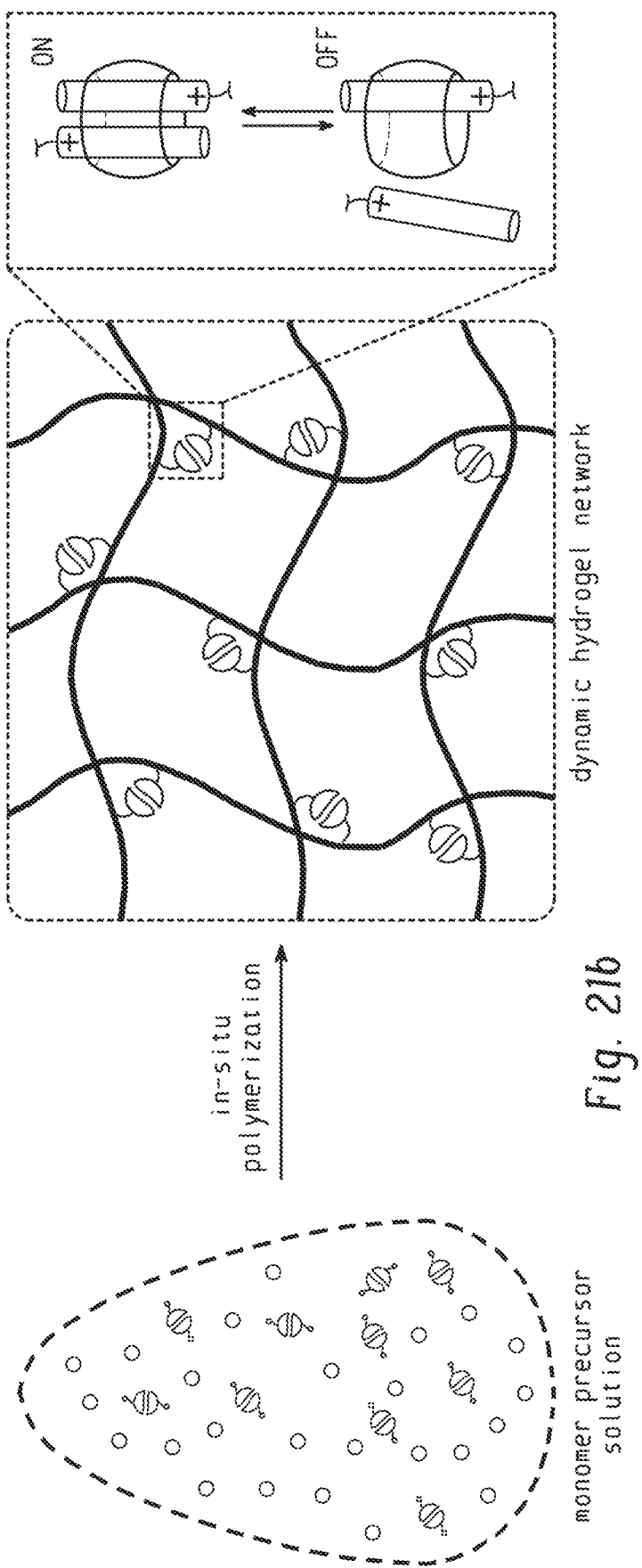
FIG. 21b shows a schematic of hydrogel formation from a polymerizable composition containing polymerizable monomers together with a CB[8] host, where the hydrogel has a dynamic network assembled from non-covalent ternary complexes of the CB[8] host and 1-benzyl-3-vinylimidazolium bromide.
Figure 21C:
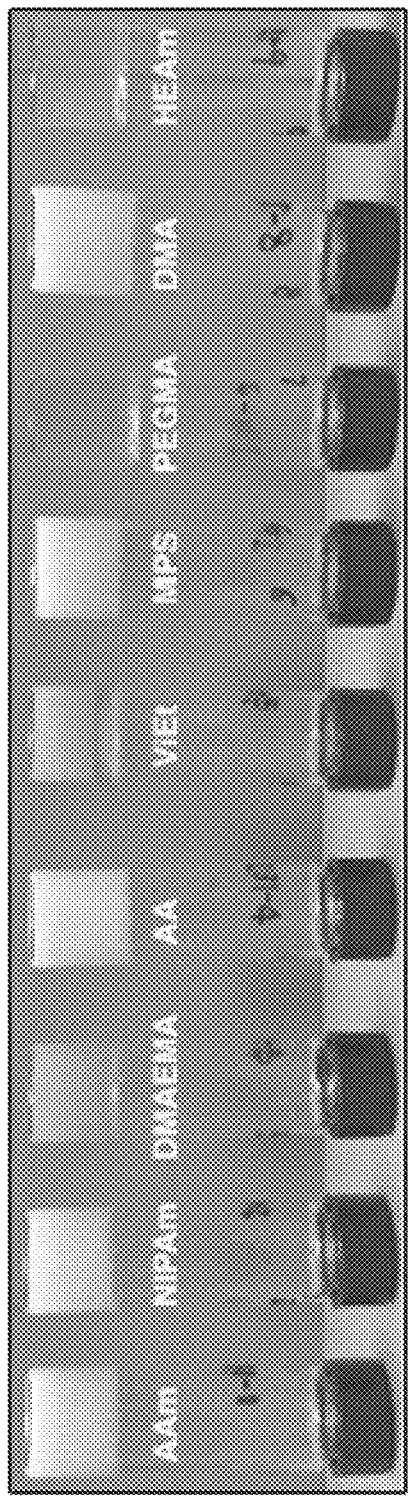
FIG. 21c is a photograph of supramolecular hydrogel networks prepared from 1-benzyl-3-vinylimidazolium bromide together with each of the monomers shown in (a) (top line), as well as the corresponding inverted-vial demonstration of their viscosities. Note: acrylamide (AAm), N-isopropylacrylamide (NIPAm), 2-(dimethylamino)ethyl methacrylate contains (DMAEMA), acrylic acid (AA), 1-vinyl-3-ethylimidazolium bromide (ViEt), 3-[2-(methacryloyloxy)ethyl](dimethyl)ammonio-1-propanesulfonate (MPS), poly(ethylene glycol) methacrylate (PEGMA), dimethylacrylamide (DMA) and N-hydroxyethyl acrylamide (HEAm).

FIG. 20 shows the change in tan (δ) with the change in a frequency sweep experiment for a range of non-covalent hydrogels prepared at different $C_{mon}$, including 0.3, 0.4, 0.5, 1.0 and 2.0 M. The experiment was conducted at room temperature. It is observed that the hydrogels prepared at a lower total monomer concentration, $C_{mon}$, exhibit quasi-solid character only at higher frequencies. Those hydrogels prepared at higher total monomer concentrations have a higher network stability across the whole sweep range Results—Dual Network As described above, a polymerizable guest (1-benzyl-3-vinylimidazolium), serving as a non-covalent supramolecular crosslinker upon complexation with CB[8] in a 2:1 manner ($K_{a1}=4.21 \times 10^7$ M$^{-1}$, $K_{a2}=4.25 \times 10^5$ M$^{-1}$, see FIG. 15), was polymerized with a small amount of a chemical crosslinker, N,N'-methylenebisacrylamide (MBA, 2 mol equiv. of the dynamic CB[8] crosslinking) and the hydrophilic monomer acrylamide, yielding a so-called aqueous dual network (see FIG. 11(a)). The dual network is readily prepared at room temperature in aqueous media.

Figure 11B:
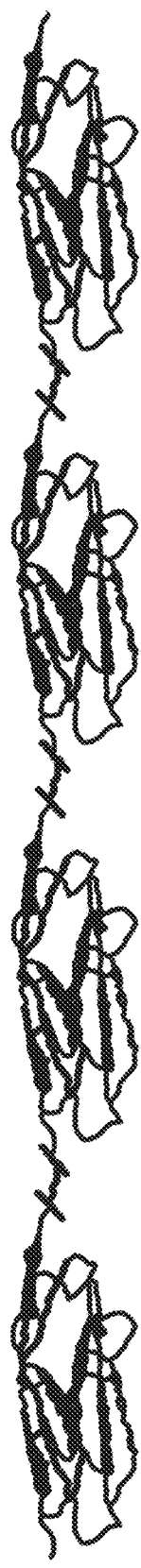
FIG. 11b shows a typical section of titin structure, which has ca. 200-300 repeating immunoglobulin (Ig)-like domains, and modular tertiary-folded-domain protein that provides the core functionality for hierarchically assembled muscle machinery.
Figure 11C:
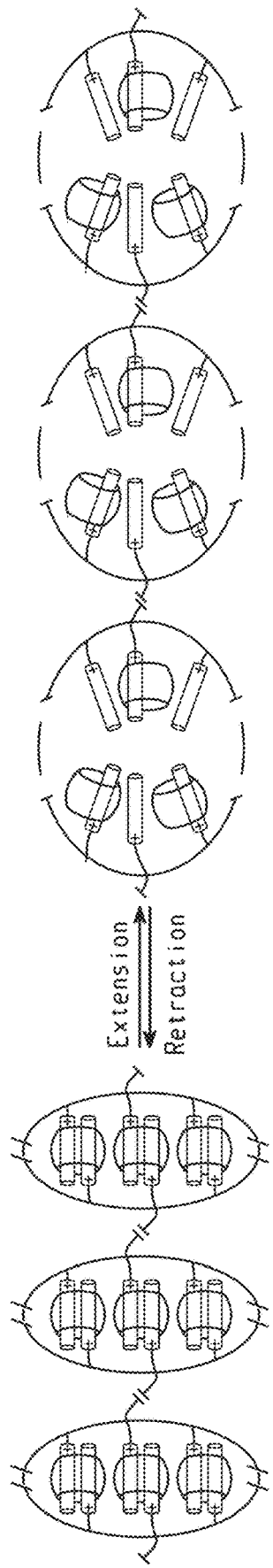
FIG. 11c shows a schematic illustration of the double-network containing multiple loops held by the cucurbit[8]uril-mediated host-guest complexation (structure extracted from the shadow area in a, the mechanically-induced dissociation of the supramolecular interaction, the fundamental mechanism for energy dissipation, as well as reformation of the host-guest complexation upon unloading and relaxation.

The CB[8]-mediated host-guest interactions (physical crosslinks) form dynamic 'loops' along the polymer chains (FIG. 11(c)). Force-induced dissociation of the host-guest complexes, similar to the un-folding of titin protein domains (FIG. 11(b)), could effectively dissipate energy and impart the system with remarkable toughness.

Rupture of the 2:1 CB[8] benzyl-imidazolium complex requires 7.6 kcal mol$^{-1}$ ($\Delta H_2$, see FIG. 15), which is comparable to the protein unfolding energy (ca. 4 kJ mol$^{-1}$ for an immunoglobulin domain; see Fong et al.). In this hydrogel, chemical crosslinking present in the system not only improves mechanical performance, but also increases the elasticity of the overall network, similar to the roles of actin and myosin, which are two motor proteins responsible for muscle contraction.

The hydrogel has a high level of transparency, and is both tough and durable upon compression. Indeed, the networks cannot be cut easily with a blade and display prompt recovery to their original shape after removal of the cutting blade. This dual network is strong enough to easily hold 500 times its own weight (FIG. 11(f)). Interestingly, the network rapidly shrinks isotropically without undergoing any cracking at the gel surface upon freeze drying; furthermore, it can absorb up to 500 times its own weight in water.

Figure 11D:
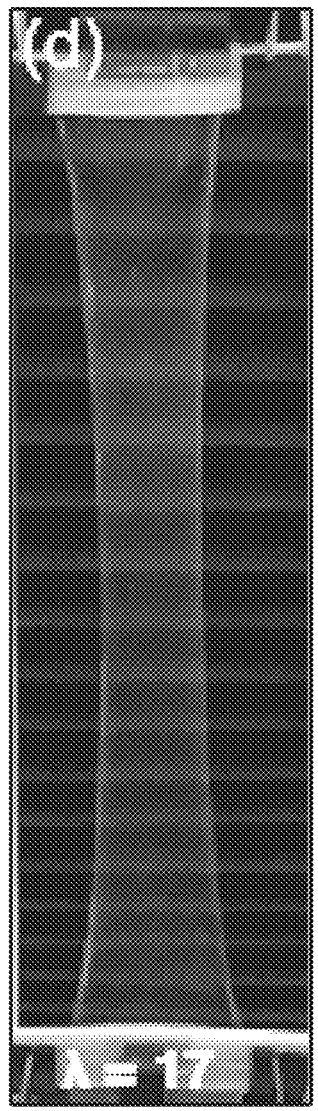
FIG. 11d is a photograph of a strip of the unnotched dual network sample (immobilized with two glass slides and rigid clamps, sample dimension: 4 cm (L)×1 mm (W)×1.5 mm (T)) upon elongation at strain of 17.

To test the stretchability of the material, a sample of 8.0 mm (L)×40 mm (W)×1.5 mm (T) was routinely stretched to between 17 to 25 times (FIG. 11(d)) its original dimension without rupture. During stretching the dual network maintains excellent transparency in the visible light range (400 to 700 nm) (see FIG. 16).

Figure 11E:
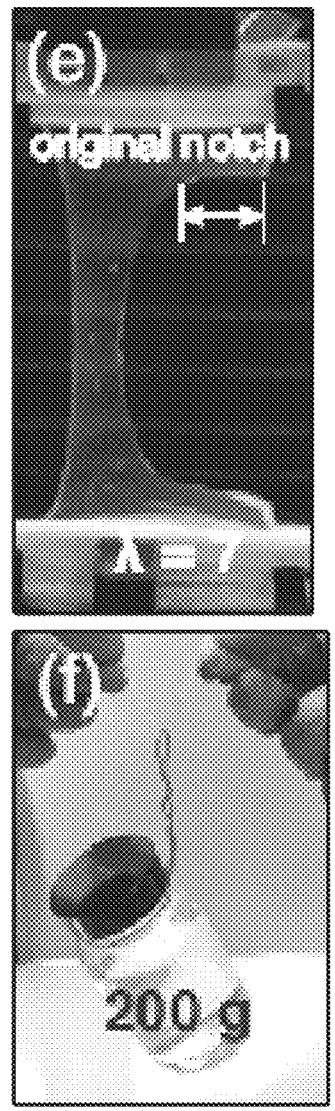
FIG. 11e is a photograph of the elongation of a notched sample (sample dimension: 4 cm (L)×1 mm (W)×1.5 mm (T), notch size 2 cm) at strain of 17. (The strain was defined by the deformation between the two clamps when the network sample is deformed, divided by the original length)
Figure 11F:
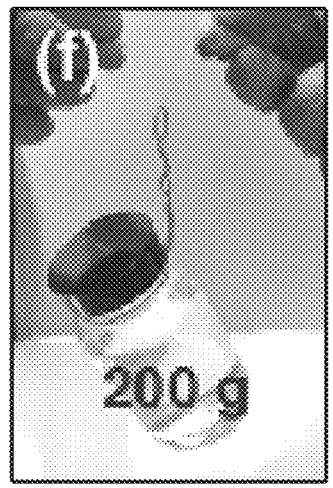
FIG. 11f is a photograph demonstrating the capability of the dual network (4 cm (L)×2 mm (W)×1.5 mm (T)) sustaining a weight of 200 g. The polymer dual network was prepared at $C_{mon}$ of 1.0 M.

Moreover, a notched sample (with a notch of 20 mm (W), half of the overall width) reached a strain of 7, exhibiting remarkable notch-insensitivity. The notch was dramatically blunted and remained stable (FIG. 11(e)) during stretching until a critical strain was reached. In order to ascertain the material's ability to dissipate energy, a drop-ball test was conducted. A large, recoverable deformation was observed when a metal ball (16 g, diameter of 2 cm, drop-height of 45 cm) was dropped onto a sample membrane. Upon hitting the membrane, the ball stretched the material extensively before bouncing back: the membrane remained intact, vibrated and recovered to its initial flat configuration successfully dissipating all energy.

Figure 12A:
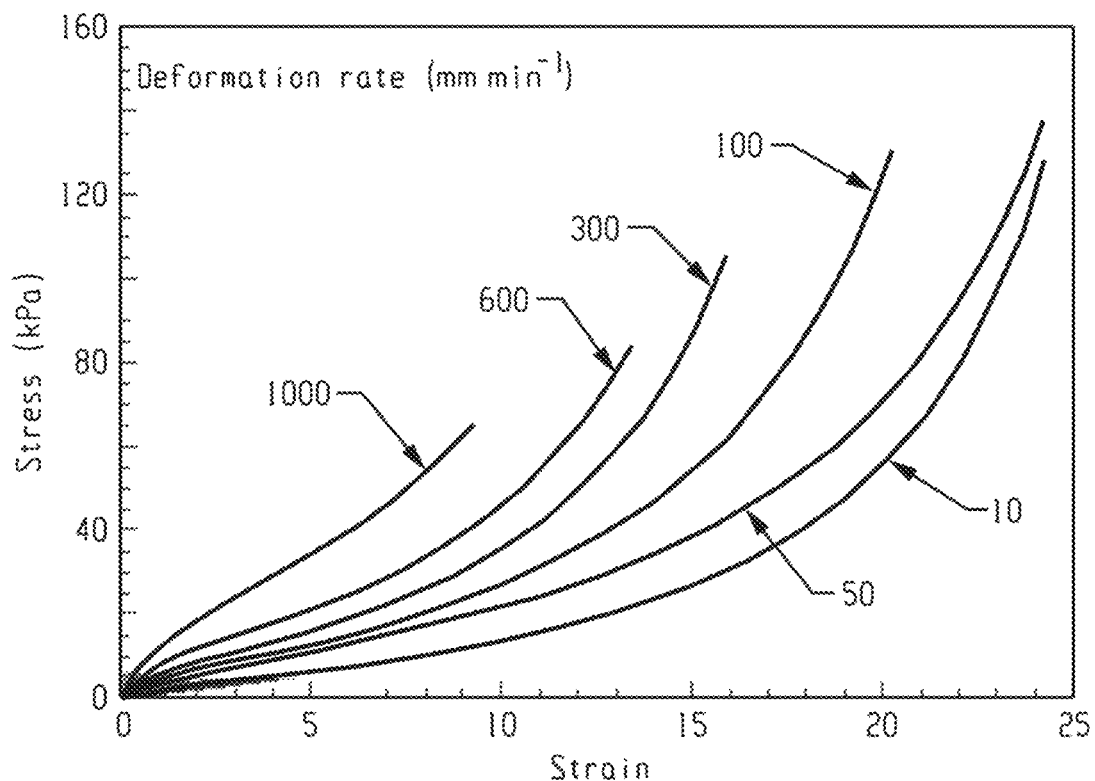
FIG. 12a shows uniaxial tensile behaviour of the supramolecular polymer dual network with different initial deformation rates, ranging from 10 to 1000 mm min$^{-1}$. Each test was conducted by pulling a dumbbell-shaped sample to rupture.

To ascertain the nonlinear and viscoelastic behaviour of the dual network at large deformation, uniaxial stretching studies were performed on dumbbell-shaped samples at various initial rates of deformation (10 to 1,000 mm $min^{-1}$). Tensile stress-strain curves (nominal stress vs. nominal strain) are shown in FIG. 12(a). Clearly, the mechanical properties are strongly influenced by the rate of deformation, and the yield in all cases is observed above a specific strain, which decreases with higher deformation rates. The yield can be attributed to the continuous dissociation of the host-guest complexes at the molecular level upon stretching, resulting in absorption of energy.

Figure 12B:
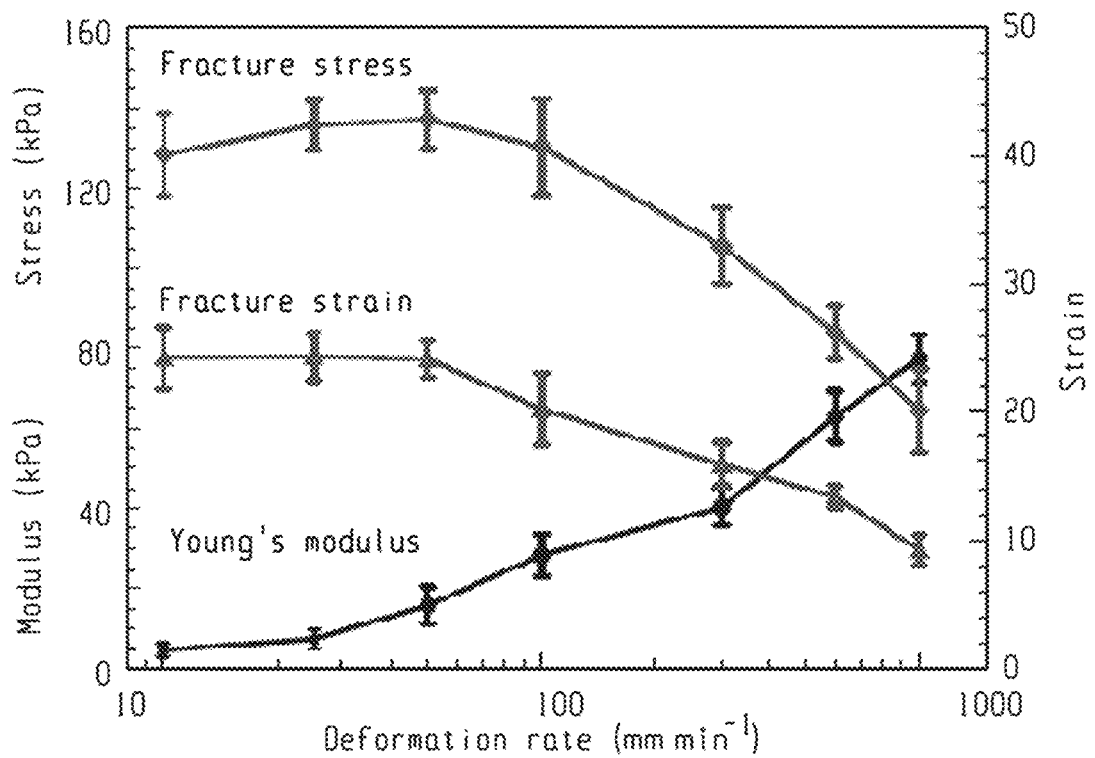
FIG. 12b shows deformation rate dependence of fracture stress, fracture strain and Young's Modulus of the dual network. The polymer dual network was prepared at $C_{mon}$ of 1.0 M.

Notably, the Young's modulus increases ca. 17 times from 4.6 kPa (10 mm $min^{-1}$) to 77.5 kPa (1,000 mm $min^{-1}$) (see FIG. 12(b)). Both fracture stress and fracture strain of the material change slightly at lower deformation rates (10 and 50 mm $min^{-1}$), however, they decrease at higher rates (see FIG. 12(b)). This is explained by the dynamic dissociation and reformation of the CB[8] host-guest interactions during low-rate stretching, which further maintains the fracture stress and strain. At higher stretching rates (>100 mm $min^{-1}$), however, the dual network loses its toughness presumably because the host-guest complexation does not have sufficient time to reform after dissociation, enabling stress to propagate at the crack tip. This viscoelastic character of the dual networks is similar to polyampholyte hydrogels reported by Gong and co-workers (see Sun et al.; and the various Luo et al. publications).

Figure 13A:
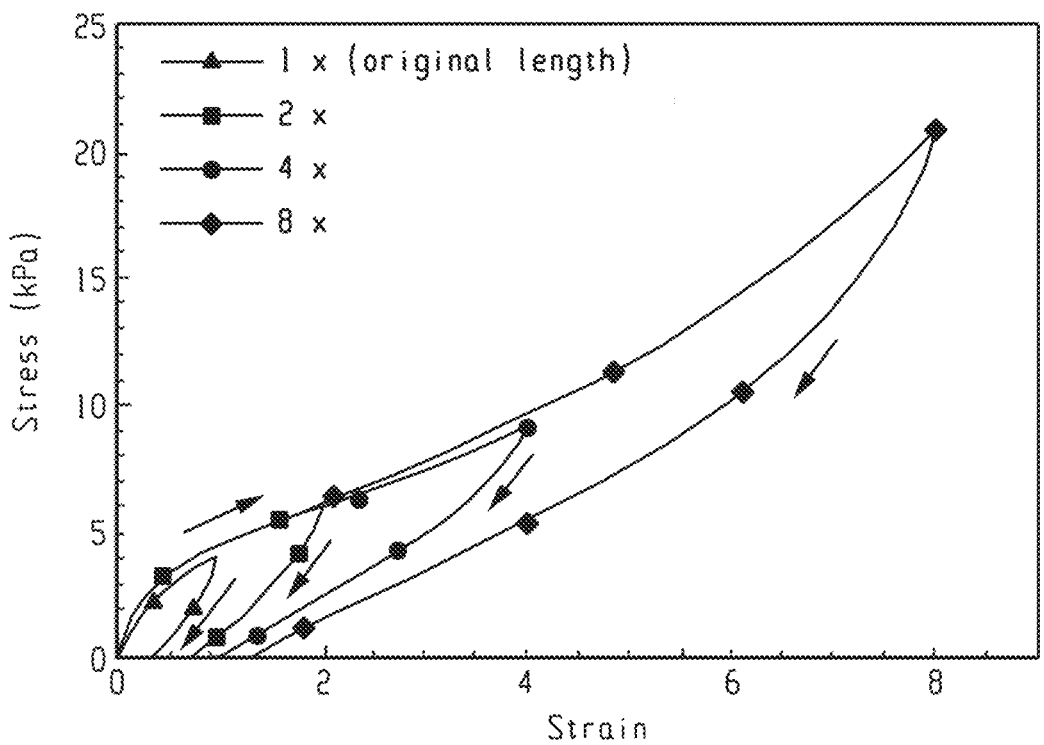
FIG. 13a shows samples of the supramolecular polymer dual network that were subjected to a cycle of loading and unloading of varying strains (deformation rate of 100 mm min$^{-1}$)
Figure 13B:
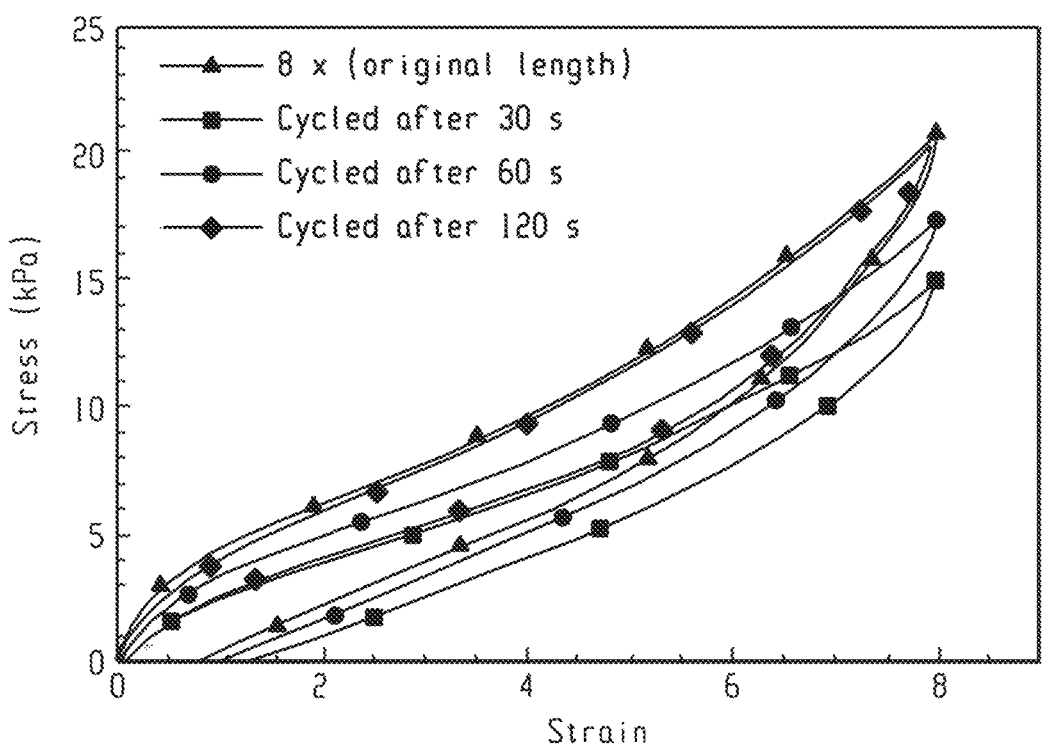
FIG. 13b shows recovery of the sample at different waiting times performed by cyclic tensile tests at a strain of 8×(original length)

Cyclic tensile tests were carried out to investigate the dynamic essence of the host-guest interactions as reversible sacrificial bonds, similar to the reversible protein folding within titin. The deformation rate in each of the strain experiments was 100 min $min^{-1}$. Four stretching-retraction cycles at different strains (1, 2, 4 and 8) are shown in FIG. 13(a), demonstrating significant quasi-plastic deformation and remarkable hysteresis. Thus it confirms the efficient energy dissipation of the supramolecular system through the sacrificial rupture of the non-covalent supramolecular crosslinks, which is an important characteristic for all high toughness materials. Moreover, during the retraction process (removal of load) the residual strain gradually decreases (FIG. 13(b)), which can be ascribed to both the elasticity arising from the covalent crosslinks and reformation of the host-guest interactions.

Figure 13C:
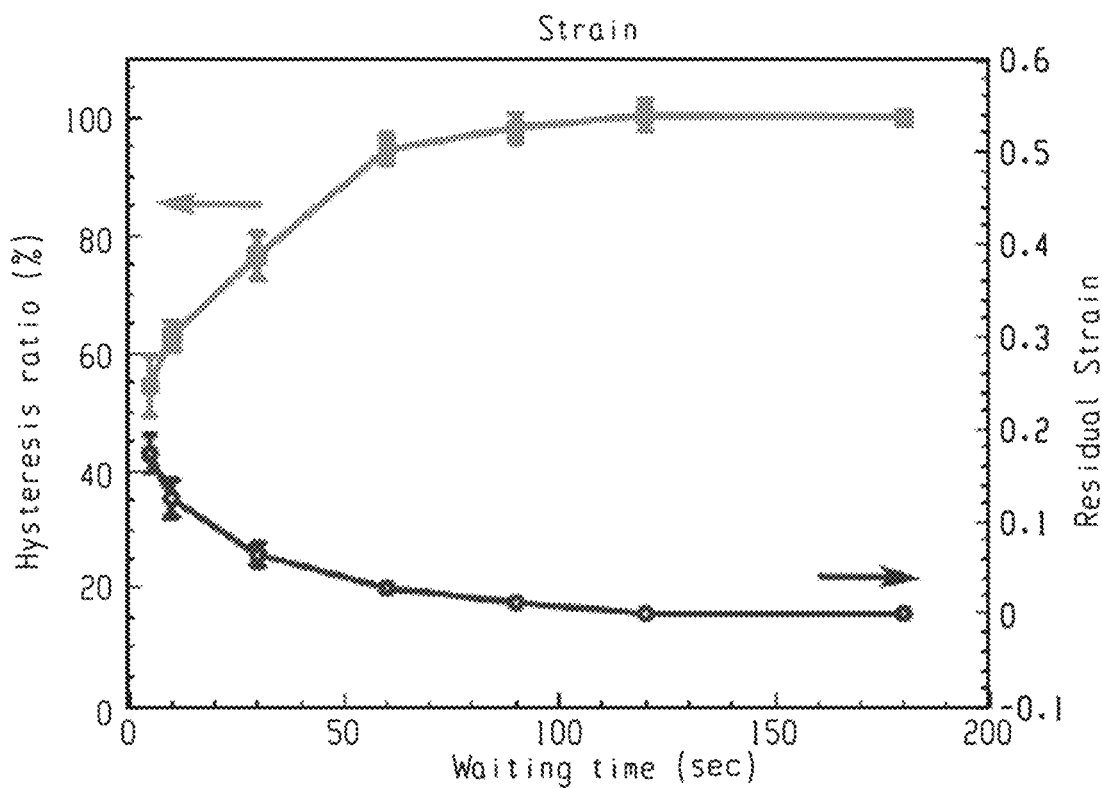
FIG. 13c shows dependence of the hysteresis ratio (area ratio of the following hysteresis loop to the first cyclic run) and residual strain on the waiting time.
Figure 13D:
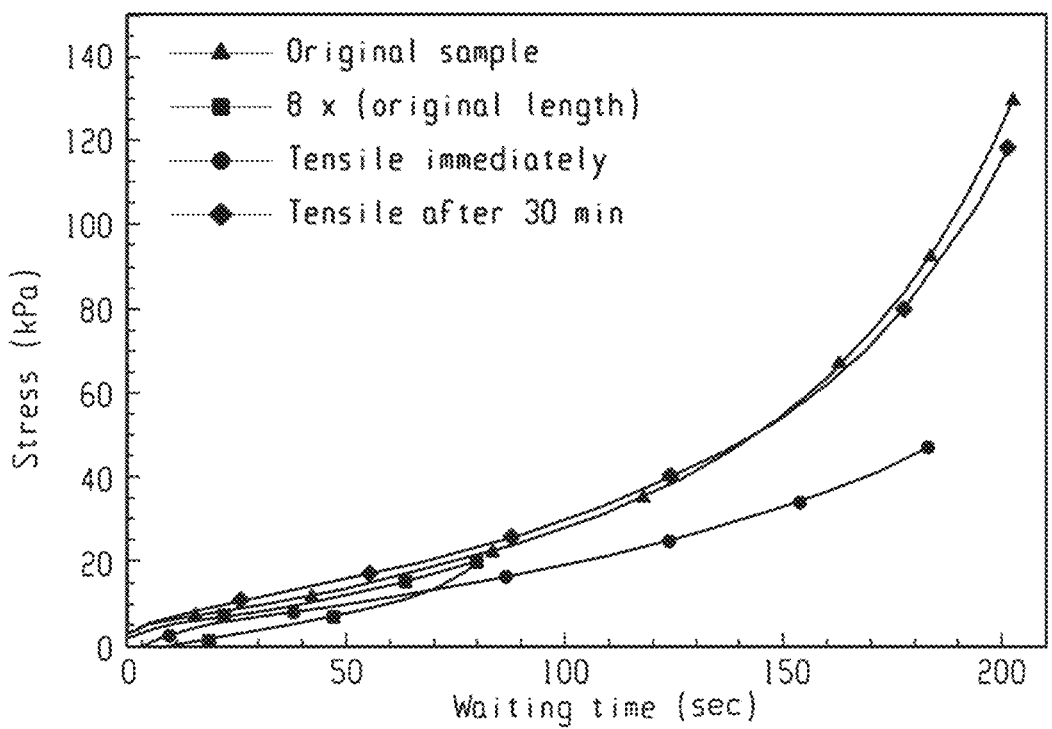
FIG. 13d shows tensile test of the sample immediately (blue curve) after the first cycle of loading and unloading at strain of 8×(original length) (pink curve), and the self-repaired sample was allowed to sit at room temperature for 30 min (green curve). The high-level of overlap between the original sample curve (black curve) and the self-repaired sample after 30 min (green curve) indicates complete recovery of mechanical properties via the reformation of supramolecular host-guest conjugation. The polymer dual network was prepared at $C_{mon}$ of 1.0 M.

Fifty percent of the observed hysteresis is recovered within 5 s (FIG. 13(c)), while the remaining 50% is recovered following a much slower and complex process. If a 120 second waiting is applied between consecutive cycles, the material does not display any noticeable plastic deformation. After the dual network was subjected to a cyclic strain of 8 times its original length it is marginally weaker than the original material, however, it is completely self-repaired after a 30-min waiting time at room temperature (FIG. 13(d)).

Figure 17:
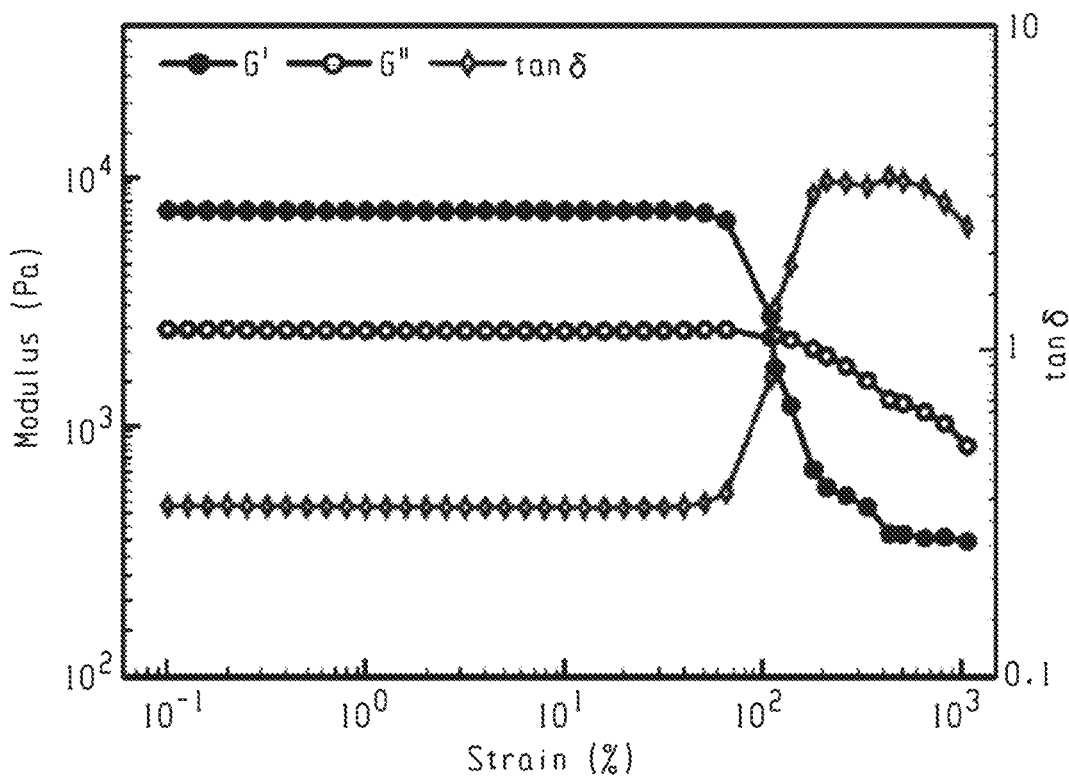
FIG. 17 shows the change in G', G" (Pa) and tan (δ) values with strain (%) for the supramolecular dual network in a dynamic room-temperature amplitude sweep experiment (from 0.1% to 1000%, 10 rad s$^{-1}$).

The dual network exhibited a broad linear viscoelastic regime, typical of a tough hydrogel as depicted in FIG. 17, with a critical yield strain of 80%, above which the rigid network starts to rupture (G">G'). The angular frequency was 10 rad $s^{-1}$, and the experiments were conducted at room temperature. On account of the reversible nature of CB[8] host-guest interactions, the dual network is shear sensitive and behaves in a highly viscoelastic manner with increasing angular frequency (w).

Figure 14A:
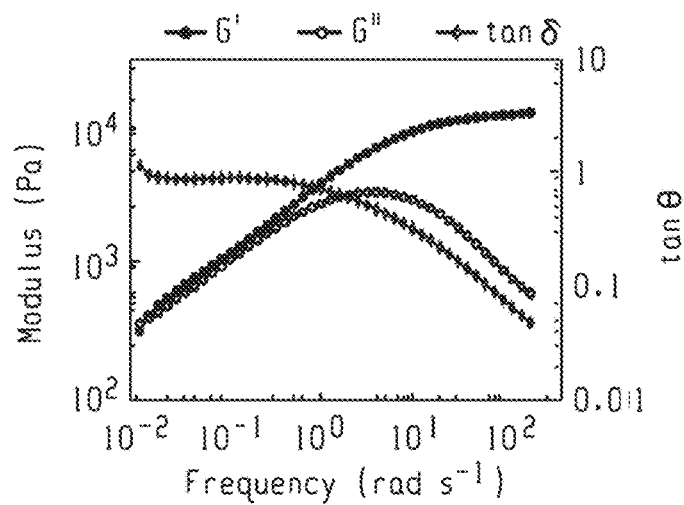
FIG. 14a shows G', G" and tan (δ) values of the supramolecular dual network from the dynamic room-temperature frequency sweep (from 0.01 to 200 rad s$^{-1}$, 0.5% strain.

The frequency-dependent viscoelastic moduli clearly identify the elastic behaviour of the dual network with G'>G" above $\omega$=1 rad $s^{-1}$ (FIG. 14(a)), corroborating the tensile tests at various strain rates (FIG. 12(a)). For the work shown in FIG. 14(a) the strain was 0.5%, and the measurements were made at room temperature.

Figure 14B:
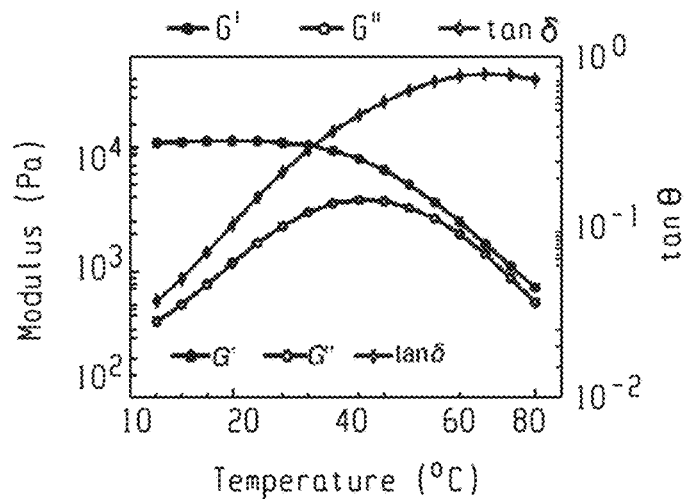
FIG. 14b shows temperature sweep (from 5 to 80° C. with an interval of 5° C., 60 rad s$^{-1}$, 0.5% strain)

G' of the dual network is constant until 40° C. and gradually decreases with increasing temperature afterwards (FIG. 14(b)). In contrast, G" continues to increase as a function of temperature and peaks at around 45° C., indicating a softening of the dual network, stemming from the thermally-induced dissociation of CB[8] host-guest complexes. The softening temperature of the dual network at which tan ($\delta$) reaches a maximum is around 70° C., above which the material completely melts, which is much higher than the softening temperature of polyampholyte hydrogels (see Sun et al.). No obvious gel-sol transition is detected throughout the temperature range studied, on account of the covalent crosslinks, which stabilise the overall structure of the dual network. For the work shown in FIG. 14(b) the strain was 0.5% and the angular frequency was 60 rad $s^{-1}$.

Figure 14C:
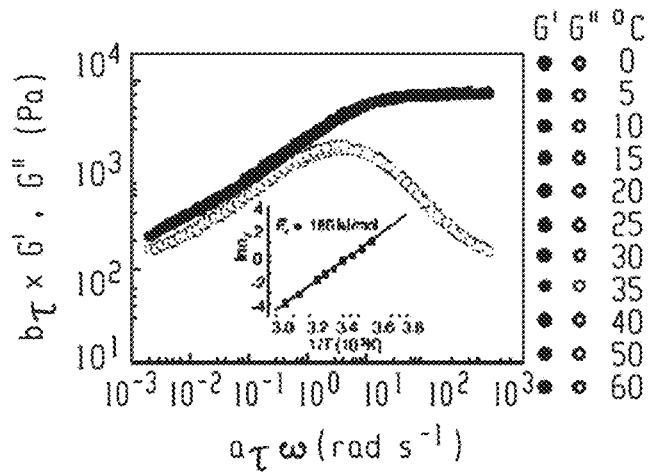
FIG. 14c shows a master curve of the supramolecular dual network (from 0 to 60° C., 0.5% strain, 10 rad s$^{-1}$)

FIG. 14(c) depicts the rheological master curve for the dual network using time-temperature superposition (TTS) referenced at 20° C. The data superimposes well over the frequency range of $10^{-3}$ to $10^3$ rad $s^{-1}$, yielding an activation energy ($E_a$) of 185 kJ $mol^{-1}$, comparable to the typical titin protein unfolding activation energies of 128 pN nm (1 kJ $mol^{-1}$=1.6 pN nm, namely, 80 kJ $mol^{-1}$) (see, for example Rief et al. and Reif et al.). For the work shown in FIG. 14(c) the strain was 0.5% and the angular frequency was 10 rad $s^{-1}$.

Figure 14D:
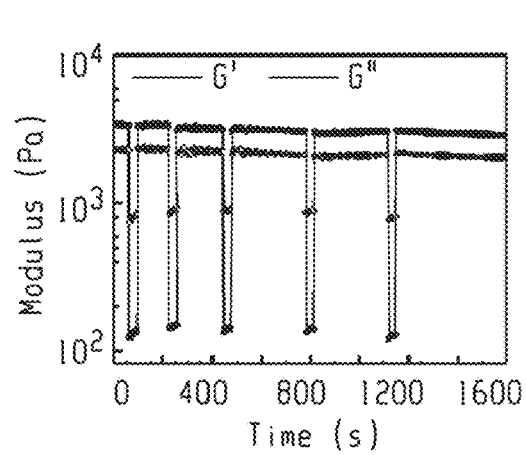
FIG. 14d shows continuous step-strain measurements of the sample at 40° C. (high-amplitude oscillatory parameters: strain (γ)=500%, angular frequency (w)=10 rad s$^{-1}$; low-amplitude oscillatory parameters: γ=0.5%, ω=10 rad s$^{-1}$).

Rapid recovery of its mechanical properties after a large-amplitude oscillatory breakdown is observed at both 20° C. (FIG. 18(a)) and 40° C. (FIG. 14(d)). Upon application of a large-amplitude oscillatory force ($\gamma$=500%, $\omega$=10 rad $s^{-1}$), G' decreases from 5,000 to 600 Pa, resulting in a quasi-liquid state (tan $\delta$=G"/G' approx. 2.0). However, when the amplitude is decreased ($\gamma$=0.5%, $\omega$=10 rad $s^{-1}$), G' immediately recovers its initial value of a quasi-solid state (tan $\delta$=0.5), similar to the reversible unfolding-folding process of muscle proteins under external mechanical stimuli.

Figure 19A:
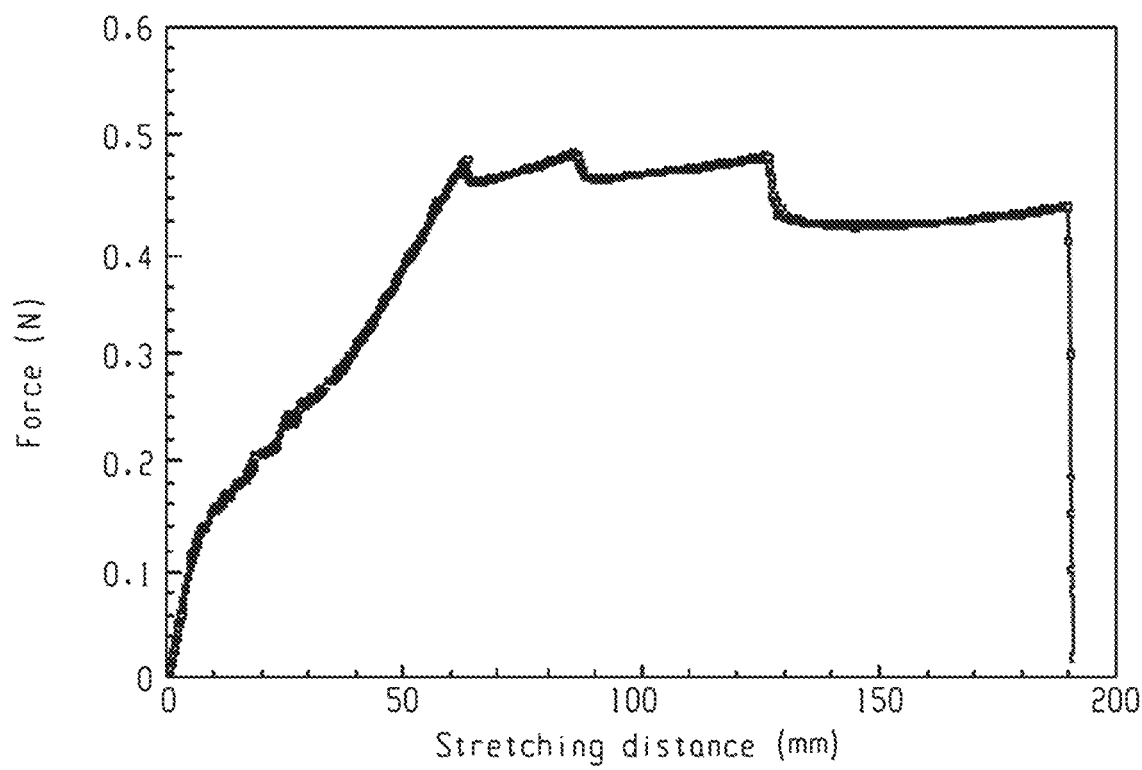
FIG. 19a is a graph showing the change in force (N) with the change in stretching distance (mm), in which a representative force-extension curve for a tearing test for the dual network.

FIG. 19 shows the change in force with change in stretching distance for a dual network hydrogel sample. In a first experiment the dual network sample was subjected to a tearing test. A representative force extension curve is shown in FIG. 19(a). Here, the tearing energy (T) is calculated from the constant stretching force F as T=2f/w. T is 630 J $m^{-2}$ for the dual network sample.

Figure 19B:
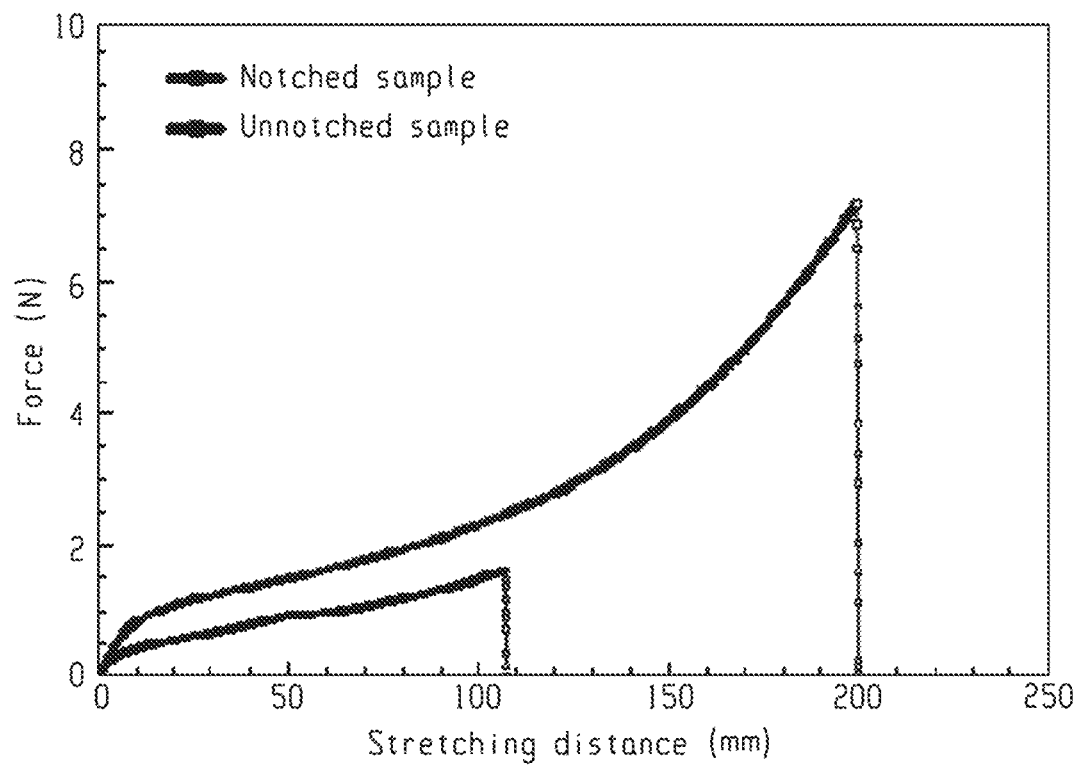
FIG. 19b shows the force-extension curves of unnotched notched samples of dual network.

In a second experiment the notched and un-notched dual network samples were stretched. The results are shown in FIG. 19(b). The values recorded in FIGS. 19(a) and (b) differ owing to the nature of the tearing and stretching tests used for the samples.

L, is the stretching distance where a notched sample starts to propagate a crack, and $U(L_c)$ is the work done when force is an applied to an un-notched sample until that sample has reached a stretching distance of $L_c$. The tearing energy (T) is calculated as $(T)=U(L_c)/(a_0 \times b_0)$ (where $a_0$ and $b_0$ were denoted as the sample width and thickness, respectively). Fracture energy obtained from this method (Rivlin-Thomas pure shear test) is 750 J m$^{-2}$, which is comparable with the value of 750 J m$^{-2}$ obtained from the tearing test (630 J m$^{-2}$). Moreover, this toughness is close to that of cartilage (1,000 J m$^{-2}$), further promising the use of this dual network for potential as structural biomaterials for regenerative tissue engineering.

Worked Examples—Dual Network

The inventors have observed and recorded the high compression of a cylinder-shaped dual network (original diameter of 10 mm, height of 5 mm) to a thin film (diameter 29 mm, height of ca. 0.59 mm, compression strain ca. 88.2%), and the recovery of this material to its original dimension within 3 min.

The inventors have observed and recorded the deformation of a dual network when subjected to a drop ball test. In the test, the material exhibits a large deformation when a metal ball (16 g, diameter 2 cm, drop height 45 cm) is dropped on a membrane of the dual network (2 mm thickness). On hitting the membrane, the ball stretches the membrane greatly and then bounces back. The membrane remains intact, vibrating, and recovers to its initial flat configuration after the vibration was damped out and the impacting energies were completely dissipated.

Additional Experimental and Results

The inventors have prepared additional hydrogels to highlight the advantages of the invention. The hydrogels are prepared from 1-benzyl-3-vinylimidazolium together with a second monomer that is selected from AAm, DMA, NIPAm, HEAm, AA, DMAEMA, ViEt and MPS.

The hydrogels were prepared in a similar manner to the non-covalent hydrogel described above, where an aqueous mixture of 1-benzyl-3-vinylimidazolium and the second monomer were used together with CB[8] and a photo-initiator. This is described in further detail below.

Materials

Monomers such as acrylamide (AAm), dimethyl acrylamide (DMA), N-isopropylacrylamide (NIPAm), N-hydroxyethyl acrylamide (HEAm), acrylic acid (AA), 2-(dimethylamino)-ethyl methacrylate (DMAEMA), poly(ethylene glycol) methacrylate (PEGMA), 1-vinyl-3-ethylimidazolium bromide (ViEt) and 3-[2-(methacryloyloxy)ethyl](dimethyl) ammonio-1-propanesulfonate (MPS) were purchased from Sigma-Aldrich. Unless specified, all the chemicals used in the work were used without further purification.

1-Benzyl-3-vinylimidazolium bromide was synthesised as described above.

Instrumentation

Photo-irradiation was performed on a photo-reactor with UV lamps (365 nm, power density of 4.8 mW cm$^{-2}$).

Rheological tests were performed using a Discovery Hybrid Rheometer (DHR)-2, a controlled stress hybrid rheometer from TA Instruments fitted with a water bath, which was set to various temperatures. Disc-shaped samples of hydrogels were prepared having a thicknesses of 0.5 mm and a diameter of 20 mm, and these were surrounded by a vendor-supplied solvent trap in order to mitigate solvent (water) loss during the measurements, and results were analysed using TA Instruments TRIOS software.

Dynamic oscillatory strain amplitude sweeps were conducted at a frequency of 10 rad s$^{-1}$. Dynamic oscillatory frequency sweep measurements were conducted at a 1% strain amplitude, between 0.01 to 100 rad s$^{-1}$, while temperature frequency sweep tests were done with a shear strain of 1% and shear frequency of 60 rad s$^{-1}$, on a ramp at an interval of 5° C. between 0 and 80° C.

The amplitude sweep, frequency sweep and step-strain experiments were performed at a temperature of 20° C.

In the temperature stability tests described below, the treatment temperature was raised in intervals of 5° C. The ramp between each test temperature was relatively fast. A typical test involved treatment of a test sample for around 5 min. at each test temperature.

Hydrogel Synthesis—Non-Covalent Cross-Links

Typically, for the acrylamide (AAm)-based hydrogel network, pre-determined amounts of 1-benzyl-3-vinylimidazolium (5 mole equiv.), CB[8] (2.5 mole equiv.) and acrylamide (95 mole equiv.) were dissolved in Milli-Q H$_2$O (2 mL, 18 mΩ). After purging with nitrogen for 30 min, the photo-initiator Irgacure 2959 (0.03 mole equiv.) was added to the monomer solution. The monomer solution was exposed to UV irradiation (4.8 mW cm$^{-2}$) for 6 h.

The other monomer based hydrogel networks, where the AAm is replaced with an alternative monomer, were prepared following the same strategy. The monomers used were DMA, NIPAm, HEAm, AA, DMAEMA, ViEt and MPS. Each monomer was used at the same mole % as AAm in the hydrogel preparation.

The as-obtained samples were used for measurement directly.

Rheological Tests

In order to probe the network dynamics of the supramolecular hydrogel networks, as well as quantify their mechanical properties, rheological characterization of the hydrogel products was performed.

Figure 22A:
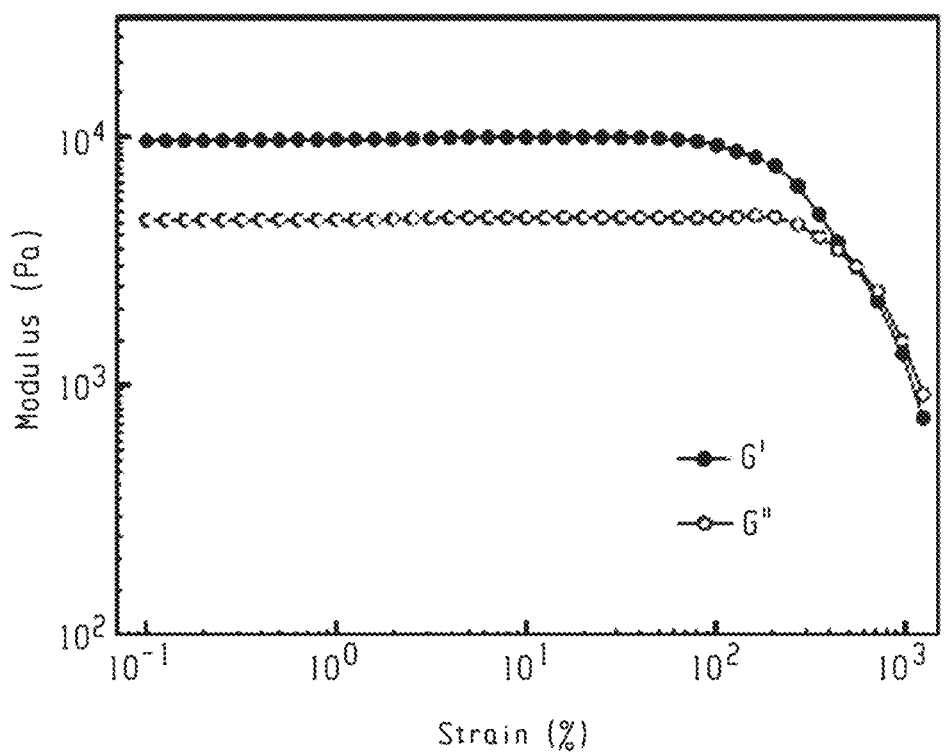
FIG. 22a shows the change in G' and G" (Modulus, Pa) for a HEAM-based CB[8]hydrogel via dynamic room-temperature (a) amplitude sweep (from $10^{-1}$ to $10^3$% strain, 10 rad $s^{-1}$)

A representative strain-dependent oscillatory rheology (FIG. 22(a)) of the HEAm-based hydrogel network (solid fraction of 12 wt %, CB[8] crosslinking of 2.5 mol. %) displays an extremely broad linear viscoelastic region (strain of 0.1-550%) before structural failure at high strain, indicating a wide processing regime and shear thinning behaviour. Compared with previous CB[8] hydrogels with intermediate mechanical properties, (i.e. with a plateau modulus of $10^1$-$10^3$ Pa) (see Appel et al. 2010; Tan et al.), hydrogel networks with G'>$10^4$ Pa can be easily obtained by tuning the overall solid fraction and/or dynamic crosslinking degree.

Figure 22B:
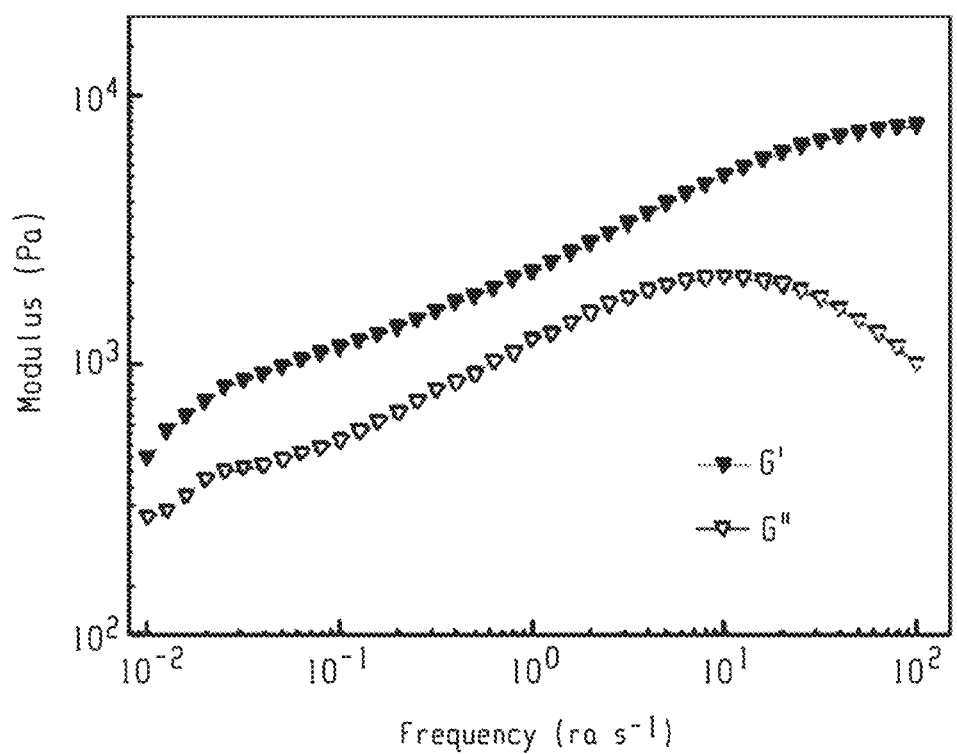
FIG. 22b shows the frequency sweep (from $10^{-2}$ to $10^2$ rad $s^{-1}$, 1% strain).

The frequency-dependence of G' and G" confirms the elastic behaviour of the supramolecular networks, as G' is dominant across the whole range of frequencies applied ($10^{-2}$-$10^2$ rad s$^{-1}$, FIG. 22(b)). In those previous studies, the critical relaxation time (β) was estimated when G' and G" crossed over in an oscillatory frequency sweep, below which the hydrogel networks are elastic (ω>β), but turned to viscous fluids as the viscous component dominated (ω<β) (see Appel et al. 2010; Tan et al.). Although β of the CB[8] hydrogel networks here could not be detected within the experimental timescales ($10^2$-$10^2$ rad s$^{-1}$), the principle of time-temperature superposition (TTS) can extend the b value over a wider angular frequency range ($10^{-3}$-$10^3$ rad s$^{-1}$) (see Appel et al. 2010; Tan et al.). On account of the larger number of dynamic crosslinks, higher solid mass fraction (>10 wt %) and polymer chain entanglement, much slower relaxation after oscillatory perturbation (i.e. higher elasticity) was obtained for these CB[8] hydrogel networks, as evidenced by the higher moduli with G'>G" throughout the entire range of angular frequencies.

Oscillatory dynamic rheological sweeps of all other hydrogel networks exploiting the different monomers mentioned above were recorded, and the results are shown in FIGS. 24 to 31. Thus, hydrogels prepared from DMA, NIPAm, HEAm, AA, DMAEMA, ViEt and MPS, together with 1-benzyl-3-vinylimidazolium, were tested under amplitude sweep and frequency sweep conditions, and the storage and loss moduli recorded.

Figure 23A:
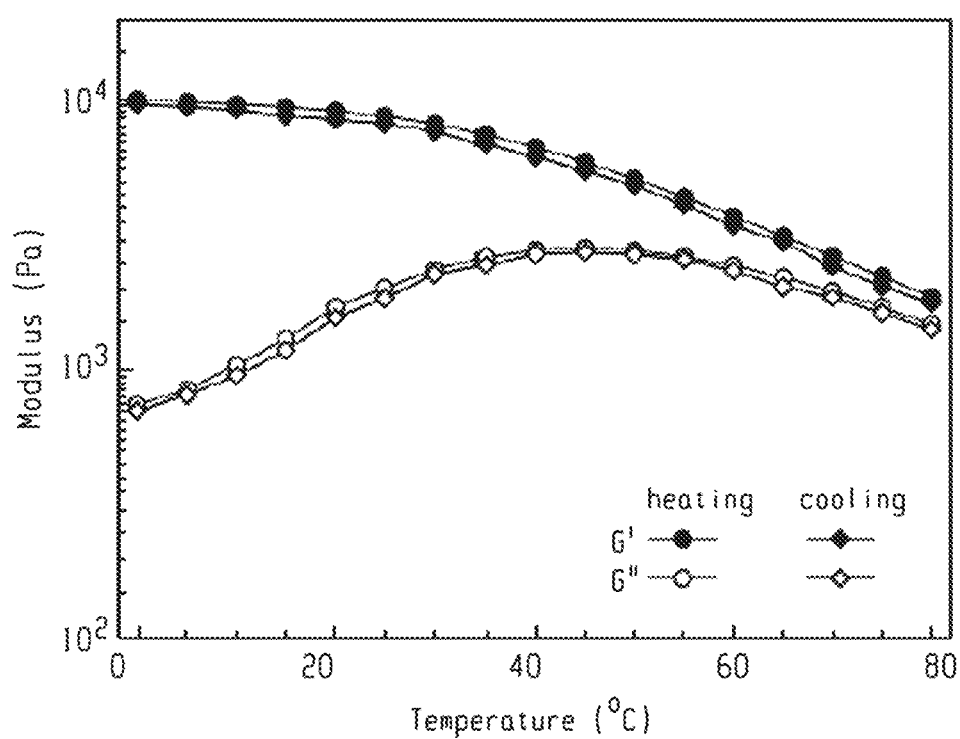
FIG. 23a shows the change in G' and G" (Modulus, Pa) for a HEAM-based CB[8]hydrogel in a thermal stability test with heating and cooling processing between 0 and 80° C.

The temperature-dependent rheological behaviour of the HEAm-based hydrogel network was recorded up to 80° C. (FIG. 23(a)), above which evaporation of water from the CB[8]hydrogel networks in the parallel plate geometry may become problematic. Throughout the whole temperature range, G' was stable before 40° C., after which the network sample started to lose its mechanical properties. A decrease in the mechanical properties with increasing temperature can be intuitively attributed to the concomitant increase in the dissociation dynamics of the host-guest complexes at elevated temperature. This observation further proves that the ternary complexes are responsible for the 3D networks and their corresponding viscoelastic properties. In the subsequent cooling process, the network samples gradually recovered their initial mechanical strength, which was not observed in previous hydrogel systems (see Tan et al.)), indicating a high thermo-stability and reversibility.

The capability of natural systems to heal cracks always involves an energy dissipative mechanism via sacrificial bonds, which can dynamically break and reform before fracturing the entire transient scaffold. Incorporation of dynamic interactions, as sacrificial bonds, can effectively increase the overall viscoelastic dissipation, but also impart the capability of recovering their initial strength after failure (see van Gemert et al.; de Greef et al.; and Liu et al.).

Figure 23B:
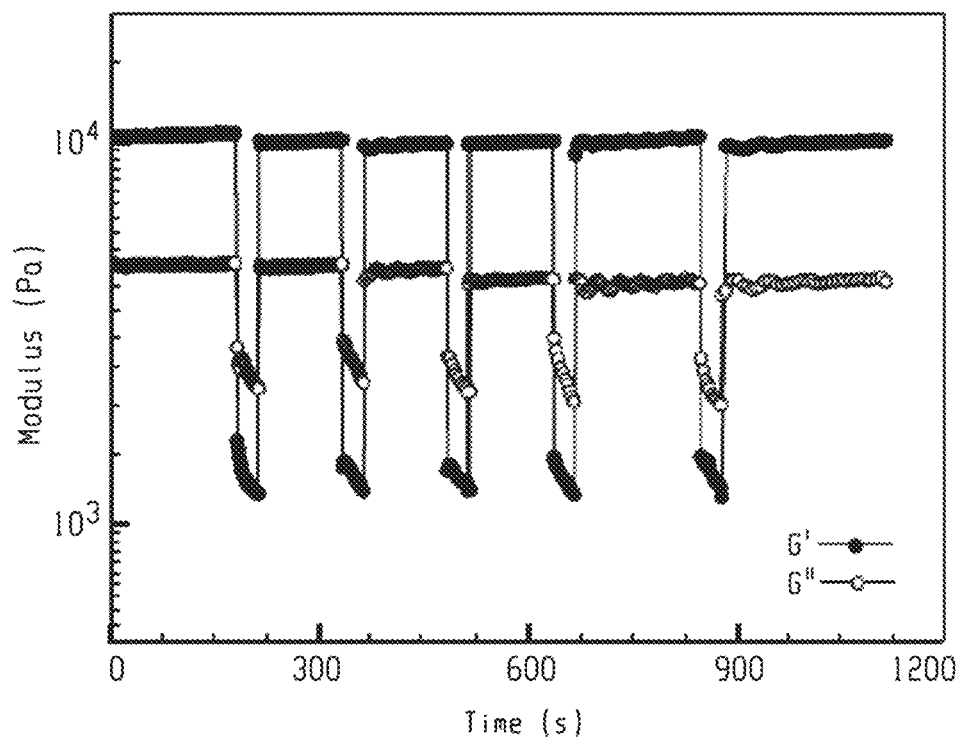
FIG. 23b in a continuous step-strain measurements of the network sample at 20° C. (high-amplitude oscillatory parameters: strain $\gamma$=500%, angular frequency $\omega$=10 rad $s^{-1}$, low-amplitude oscillatory parameters: $\gamma$=0.5%, $\omega$=10 rad $s^{-1}$).

Microscopic self-healing behaviour of the HEAm-based hydrogel network was investigated by rheological step-strain measurements, where mesoscale ruptures were induced at high strain, a critical parameter for processing and injection of soft materials. As shown in FIG. 23(b), a high strain oscillatory sweep ($\gamma$=500%) results in a quasi-liquid structure (G"/G' approx. 2.0), where the hydrogel sample readily flows. However, when the network was subjected to a subsequent low magnitude strain sweep ($\gamma$=0.5%), G' immediately recovered to its initial value at a quasi-solid state (tan $\delta$ approx. 0.5) in a few seconds following the stress-induced flow. Interestingly, the rate and extent of recovery were nearly similar over several cycles of simultaneous breaking and reforming, highlighting the reversible and robust essence of such dynamically-cross-linked networks. Therefore, the reversible dissociation/association of the host-guest complexes can effectively retard network failure, and ensure an astounding toughness.

Similar macroscopic self-healing of the hydrogel network was also observed in tensile tests of acrylamide based CB[8] networks, as described in the worked examples above.

CB[8] hydrogel networks exhibited a toughness up to 2,000 J m$^{-2}$ (from Rivlin-Thomas pure shear tests), which is comparable to that of cartilage (1,000 J m$^{-2}$). As such, these tough hydrogel networks exhibit great potential as structural biomaterials for regenerative tissue engineering, similar to double networks reported by Gong and co-workers (see Nonoyama et al.) and graphene-based hydrogels by Li and co-workers (see Lu et al.).

Moreover, this synthetic strategy allows for the flexible preparation of hydrogel networks over a wide range of mechanical strength, due to the applicability to monomer precursor solutions with a range of monomer concentrations, which are not limited by solution viscosity. For example, hydrogel networks with intermediate strength (1-1,000 Pa) can be obtained by tuning the overall solid fraction and crosslinking degree.

Such control gives rise to their potential use as moldable and injectable hydrogels for in vivo drug delivery platforms, similar to the polymer/particle hydrogel reported by Langer and co-workers (see Appel et al. 2015).

In addition to applications inspired by these networks' remarkable mechanical performance, mobile ions within the selected hydrogel networks enable the percolation of conductive pathways, thus extending their potential as highly-stretchable ionic conductors and pressure sensors. Inherent ionic conductivity of these flexible yet tough transparent materials opens the possibility to construct robust interfaces between ionic/biological and ionic/electronic systems, similar to the aliginate-based networks demonstrated by Suo, Zhao and co-workers (see Keplinger et al.; Yuk et al.).

The incorporation of positively-charged monomers such as ViEt, negatively-charged monomers such as AA, zwitterionic monomers (e.g. MPC), and other pH-sensitive monomers (e.g. DMAEMA and AA) or thermo-sensitive monomers (e.g. NIPAm, DMAEMA and PEGMA) can also enrich these supramolecular hydrogel networks with additional characteristics.

REFERENCES

All documents mentioned in this specification are incorporated herein by reference in their entirety.
Aida et al. *Science* 2012, 335, 813
Appel et al. *J. Am. Chem. Soc.* 2010, 132, 14251
Appel et al. *J. Am. Chem. Soc.* 2012, 134, 11767
Appel et al. *Nat. Commun.* 2015, 6, 6295
Burnworth et al. *Nature* 2011, 472, 334.
Chen et al. *Nat. Chem.* 2012, 4, 467
CN 104086691
CN 105061783
Cordier et al. *Nature* 2008, 451, 977
de Greef et al. *Nature* 2008, 453, 171
Fong et al. *J. Mol. Biol.* 1996, 264, 624
Haque et al. *Macromolecules* 2011, 44, 8916
Keplinger et al. *Science* 2013, 341, 984
Kim et al. *J. Am. Chem. Soc.* 2000, 122, 540
Liu et al. *Macromol. Chem. Phys.* 2016, 217, 319
Lu et al. *Adv. Mater.* 2016, 28, 4025
Luo et al. *ACS Macro Lett.* 2015, 4, 961
Luo et al. *Adv. Mater.* 2015, 27, 2722
Luo et al. *Macromolecules* 2014, 47, 6037
Luo et al. *Macromolecules* 2016, 49, 2750-2760
Nakahata et al. *Nat. Commun.* 2011, 2, 511
Nonoyama et al. *Adv. Mater.* 2016, 28, 6740
Rief et al. *Biophys. J.* 1998, 75, 3008
Rief et al. *Phys. Rev. Lett.* 1998, 81, 4764
Scherman et al. *Chem. Commun.* 2010, 46, 2007
Song et al. *ACS Macro Lett.* 2016, 5, 1084
Sun et al. *Nat. Mater.* 2013, 12, 932
Sun et al. *Nature* 2012, 489, 133
Tan et al. *Polym. Chem.* 2015, 6, 7652
Tanaka et al. *J. Phys. Chem. B* 2005, 109, 11559
Tee et al. *Nature Nanotechnology* 2012, 7, 825
US 2012/0103615
van Gemert et al. *Macromol. Chem. Phys.* 2012, 213, 234
Wang et al. *Nat. Chem.* 2013, 5, 1042
White et al. *Nature* 2001, 409, 794

WO 2013/124654
WO 2015/103125
Xu et al. *ACS Appl. Mater. Interfaces* 2017, 9, 11368
Yan et al. *Chem. Soc. Rev.* 2012, 41, 6042
Yuk et al. *Nat. Mater.* 2016, 15, 190

The invention claimed is:

1. A hydrogel comprising a network of non-covalently linked polymers formed by at least partially polymerizing an aqueous polymerizable composition comprising cucurbituril and a first monomer having a guest for the cucurbituril, wherein the total monomer concentration, $C_{mon}$, within the polymerizable composition is from 0.05 M to 2.0 M, and wherein the guest and cucurbituril have an association constant of at least $10^3$ M$^{-1}$.

2. The hydrogel of claim 1, wherein the total amount of polymer in the hydrogel is at most 2.5 wt %.

3. The hydrogel of claim 1, wherein the hydrogel has at least one of:
a viscosity in the range 100 to 15,000 Pa s measured at a shear rate in the range 0.1 to 0.5 1/s, at 25° C. in a steady shear measurement;
a storage modulus, G', of 100 to 30,000 Pa as measured at 25° C. from a strain amplitude sweep measurement and the value is taken at a strain value in the range 0.01 to 100%;
a storage modulus, G', of 10 to 10,000 Pa, as measured at 25° C. from a frequency sweep measurement and is the value taken at a frequency value in the range 0.1 to 100 rad/s;
a loss modulus, G", of 100 to 10,000 Pa, measured at 25° C. from a strain amplitude sweep measurement and the value is taken at a strain value in the range 0.01 to 100%;
a loss modulus, G", of 1 to 5,000 Pa, measured at 25° C. from a frequency sweep measurement and is the value taken at a frequency value in the range 0.1 to 100 rad/s; or
a tan (δ) value in the range 0.1 to 0.5, and is the value recorded at 25° C. from a strain amplitude sweep measurement and taken at a strain value in the range 0.1 to 10%.

4. The hydrogel of claim 1, wherein the hydrogel is holding a component.

5. A biomaterial comprising the hydrogel of claim 1.

6. An adhesive comprising the hydrogel of claim 1.

* * * * *